United States Patent
Houser et al.

(10) Patent No.: US 7,229,431 B2
(45) Date of Patent: Jun. 12, 2007

(54) RAPID EXCHANGE CATHETER WITH STENT DEPLOYMENT, THERAPEUTIC INFUSION, AND LESION SAMPLING FEATURES

(75) Inventors: Russell A. Houser, 1787 Verdite St., Livermore, CA (US) 94550; William D. Hare, Bethesda, MD (US)

(73) Assignee: Russell A. Houser, Livermore, CA (US)

( * ) Notice: Subject to any disclaimer, the term of this patent is extended or adjusted under 35 U.S.C. 154(b) by 407 days.

(21) Appl. No.: 10/290,534

(22) Filed: Nov. 8, 2002

(65) Prior Publication Data

US 2003/0120208 A1 Jun. 26, 2003

Related U.S. Application Data

(60) Provisional application No. 60/331,125, filed on Nov. 8, 2001, provisional application No. 60/347,291, filed on Jan. 14, 2002.

(51) Int. Cl.
| | |
|---|---|
| *A61M 29/00* | (2006.01) |
| *A61M 31/00* | (2006.01) |
| *A61M 37/00* | (2006.01) |
| *A61M 25/01* | (2006.01) |

(52) U.S. Cl. ................... 604/103.04; 604/528
(58) Field of Classification Search ............. 604/96.01, 604/103.03, 103.04, 523, 528, 915; 606/191, 606/192, 194; 623/1.11
See application file for complete search history.

(56) References Cited

U.S. PATENT DOCUMENTS

| | | | |
|---|---|---|---|
| 4,748,982 A | 6/1988 | Horzewski et al. | |
| 4,762,129 A | 8/1988 | Bonzel | |
| 4,988,356 A | 1/1991 | Crittenden et al. | |
| 5,002,531 A | 3/1991 | Bonzel | |
| 5,034,001 A | 7/1991 | Garrison et al. | |
| 5,040,548 A | 8/1991 | Yock | |
| 5,195,978 A | 3/1993 | Schiffer | |
| 5,232,445 A | 8/1993 | Bonzel | |
| 5,263,963 A | 11/1993 | Garrison et al. | |
| 5,267,958 A | 12/1993 | Buchbinder et al. | |

(Continued)

FOREIGN PATENT DOCUMENTS

WO    WO 98/10820    3/1998

(Continued)

*Primary Examiner*—Loan H. Thanh

(57) ABSTRACT

A catheter is insertable into a vessel within a mammalian body. The catheter includes a tubular body, at least one channel extending along the tubular body, and a central lumen. The tubular body includes an exterior surface, a first end and a second end, and defines a length between the first end and the second end. The channel passes between a first opening and a second opening and includes a slot in the tubular body between the channel and the exterior surface of the tubular body such that a tubular member can be passed between the channel and the exterior surface. The slot extends from the first opening to the second opening and includes a pair of edges. The central lumen extends along the tubular body at least for a portion of the length of the tubular body. The catheter can be used as a rapid exchange catheter, for stent deployment, for drug delivery or therapeutic infusion with or without electroporation, to provide localized heat, to provide ultrasonic visualization and ablation, and to examine for vulnerable plaque. The catheter may have multiple balloons.

12 Claims, 52 Drawing Sheets

U.S. PATENT DOCUMENTS

| | | | |
|---|---|---|---|
| 5,290,247 A | 3/1994 | Crittenden et al. | |
| 5,300,025 A | 4/1994 | Wantink | |
| 5,334,147 A | 8/1994 | Johnson | |
| 5,336,184 A | 8/1994 | Teirstein | |
| 5,350,395 A | 9/1994 | Yock | |
| 5,378,236 A | 1/1995 | Seifert | |
| 5,380,283 A | 1/1995 | Johnson | |
| 5,383,853 A | 1/1995 | Jung et al. | |
| 5,389,087 A * | 2/1995 | Miraki | 604/247 |
| 5,409,458 A | 4/1995 | Khairkhahan et al. | |
| 5,413,557 A | 5/1995 | Solar | |
| 5,413,559 A | 5/1995 | Sirhan et al. | |
| 5,413,560 A | 5/1995 | Solar | |
| 5,451,233 A | 9/1995 | Yock | |
| 5,458,613 A * | 10/1995 | Gharibadeh et al. | 606/194 |
| 5,468,225 A | 11/1995 | Teirstein | |
| 5,472,425 A | 12/1995 | Teirstein | |
| 5,474,537 A | 12/1995 | Solar | |
| 5,489,271 A | 2/1996 | Andersen | |
| 5,496,346 A | 3/1996 | Horzewski et al. | |
| 5,501,227 A | 3/1996 | Yock | |
| 5,516,336 A | 5/1996 | McInnes et al. | |
| 5,520,647 A | 5/1996 | Solar | |
| 5,531,690 A | 7/1996 | Solar | |
| 5,531,700 A | 7/1996 | Moore et al. | |
| 5,533,968 A | 7/1996 | Muni et al. | |
| 5,545,134 A | 8/1996 | Hilaire et al. | |
| 5,549,556 A | 8/1996 | Ndondo-Lay et al. | |
| 5,569,199 A | 10/1996 | Solar | |
| 5,626,600 A | 5/1997 | Horzewski et al. | |
| 5,667,521 A | 9/1997 | Keown | |
| 5,669,880 A | 9/1997 | Solar | |
| 5,685,312 A | 11/1997 | Yock | |
| 5,690,642 A | 11/1997 | Osborne et al. | |
| 5,709,658 A | 1/1998 | Sirhan et al. | |
| 5,738,667 A | 4/1998 | Solar | |
| 5,743,875 A | 4/1998 | Sirhan et al. | |
| 5,755,685 A | 5/1998 | Andersen | |
| 5,769,868 A | 6/1998 | Yock | |
| 5,772,669 A | 6/1998 | Vrba | |
| 5,788,707 A | 8/1998 | Del Toro et al. | |
| 5,807,331 A | 9/1998 | den Heijer et al. | |
| 5,807,355 A | 9/1998 | Ramzipoor et al. | |
| 5,814,061 A | 9/1998 | Osborne et al. | |
| 5,833,659 A | 11/1998 | Kranys | |
| RE36,104 E | 2/1999 | Solar | |
| 5,919,164 A | 7/1999 | Andersen | |
| 5,921,971 A | 7/1999 | Agro et al. | |
| 5,976,155 A | 11/1999 | Foreman et al. | |
| 5,980,533 A | 11/1999 | Holman | |
| 5,993,460 A | 11/1999 | Beitelia et al. | |
| 6,004,328 A | 12/1999 | Solar | |
| 6,007,517 A * | 12/1999 | Anderson | 604/103.04 |
| 6,007,522 A | 12/1999 | Agro et al. | |
| 6,013,069 A | 1/2000 | Sirhan et al. | |
| 6,019,777 A | 2/2000 | Mackenzie | |
| 6,027,475 A | 2/2000 | Sirhan et al. | |
| 6,036,715 A | 3/2000 | Yock | |
| 6,042,588 A | 3/2000 | Munsinger et al. | |
| 6,056,722 A | 5/2000 | Jayaraman | |
| 6,059,813 A | 5/2000 | Vrba et al. | |
| 6,071,285 A | 6/2000 | Lashinski et al. | |
| 6,077,295 A | 6/2000 | Limon et al. | |
| 6,096,045 A | 8/2000 | Del Toro et al. | |
| 6,113,607 A | 9/2000 | Lau et al. | |
| 6,113,608 A | 9/2000 | Monroe et al. | |
| 6,117,140 A | 9/2000 | Munsinger | |
| 6,120,522 A | 9/2000 | Vrba et al. | |
| 6,136,011 A | 10/2000 | Stambaugh | |
| 6,139,524 A | 10/2000 | Killion | |
| 6,143,016 A | 11/2000 | Bleam et al. | |
| 6,152,910 A | 11/2000 | Agro et al. | |
| 6,165,167 A | 12/2000 | Delaloye | |
| 6,165,195 A | 12/2000 | Wilson et al. | |
| 6,165,197 A | 12/2000 | Yock | |
| 6,165,200 A | 12/2000 | Tsugita et al. | |
| 6,190,358 B1 | 2/2001 | Fitzmaurice et al. | |
| 6,193,727 B1 | 2/2001 | Foreman et al. | |
| 6,217,586 B1 | 4/2001 | Mackenzie | |
| 6,221,090 B1 | 4/2001 | Wilson et al. | |
| 6,221,098 B1 | 4/2001 | Wilson et al. | |
| 6,228,110 B1 | 5/2001 | Munsinger | |
| 6,254,608 B1 | 7/2001 | Solar | |
| 6,254,609 B1 | 7/2001 | Vrba et al. | |
| 6,264,682 B1 | 7/2001 | Wilson et al. | |
| 6,299,595 B1 | 10/2001 | Dutta et al. | |
| 6,302,893 B1 | 10/2001 | Limon et al. | |
| 6,312,404 B1 | 11/2001 | Agro et al. | |
| 6,312,406 B1 | 11/2001 | Jayaraman | |
| 6,371,961 B1 | 4/2002 | Osborne et al. | |
| 6,394,995 B1 | 5/2002 | Solar et al. | |
| 6,447,501 B1 | 9/2002 | Solar et al. | |
| 6,451,043 B1 | 9/2002 | McInnes et al. | |
| 6,458,099 B2 | 10/2002 | Dutta et al. | |
| 6,569,180 B1 | 5/2003 | Sirhan et al. | |
| 6,575,993 B1 | 6/2003 | Yock | |
| 6,585,657 B2 | 7/2003 | Yock | |
| 6,589,207 B1 | 7/2003 | El-Nounou | |
| 6,592,548 B2 | 7/2003 | Jayaraman | |
| 6,592,549 B2 | 7/2003 | Gerdts et al. | |
| 6,849,077 B2 * | 2/2005 | Ricci | 606/108 |
| 2001/0011180 A1 | 8/2001 | Fitzmaurice et al. | |
| 2001/0012927 A1 | 8/2001 | Mauch | |
| 2001/0016767 A1 | 8/2001 | Wilson et al. | |
| 2001/0016768 A1 | 8/2001 | Wilson et al. | |
| 2001/0029362 A1 | 10/2001 | Sirhan et al. | |
| 2001/0029396 A1 | 10/2001 | Wilson et al. | |
| 2001/0031979 A1 | 10/2001 | Ricci | |
| 2001/0037116 A1 | 11/2001 | Wilson et al. | |
| 2001/0037138 A1 | 11/2001 | Wilson et al. | |
| 2001/0041905 A1 | 11/2001 | Yock | |
| 2001/0044648 A1 | 11/2001 | Wolinsky et al. | |
| 2001/0047176 A1 | 11/2001 | Lee et al. | |
| 2001/0056285 A1 | 12/2001 | Dutta et al. | |
| 2002/0004635 A1 | 1/2002 | Yock | |
| 2002/0026149 A1 | 2/2002 | Agro et al. | |
| 2002/0032457 A1 | 3/2002 | Sirhan et al. | |
| 2002/0082525 A1 | 6/2002 | Oslund et al. | |
| 2002/0133118 A1 | 9/2002 | Gerdts et al. | |
| 2002/0133217 A1 | 9/2002 | Sirhan et al. | |
| 2002/0143251 A1 | 10/2002 | Richardson et al. | |
| 2002/0177841 A1 | 11/2002 | Moloney et al. | |
| 2003/0018376 A1 | 1/2003 | Solar et al. | |
| 2003/0028143 A1 | 2/2003 | Dutta et al. | |
| 2003/0040769 A1 | 2/2003 | Kelley et al. | |
| 2003/0055377 A1 | 3/2003 | Sirhan et al. | |
| 2003/0083691 A1 | 5/2003 | Wantink | |
| 2003/0097095 A1 | 5/2003 | Brady et al. | |
| 2003/0109886 A1 | 6/2003 | Keegan et al. | |

FOREIGN PATENT DOCUMENTS

| | | |
|---|---|---|
| WO | WO 98/10821 | 3/1998 |
| WO | WO 99/49808 | 10/1999 |
| WO | WO 99/49929 | 10/1999 |
| WO | WO 01/45788 | 6/2001 |
| WO | WO 01/58383 | 8/2001 |
| WO | WO 01/64261 | 9/2001 |

* cited by examiner

OD1>OD2>OD3>OD4

ID1>ID2>ID3>ID4

OD1>OD2>OD3>OD4

ID1=ID2=ID3=ID4

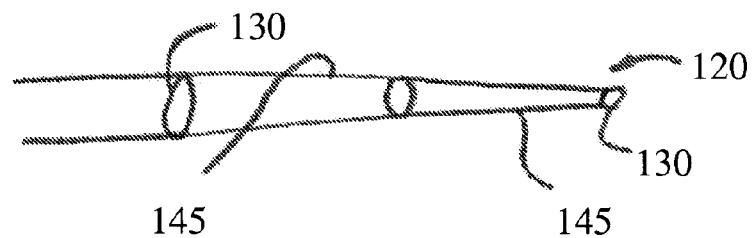
Fig. 10
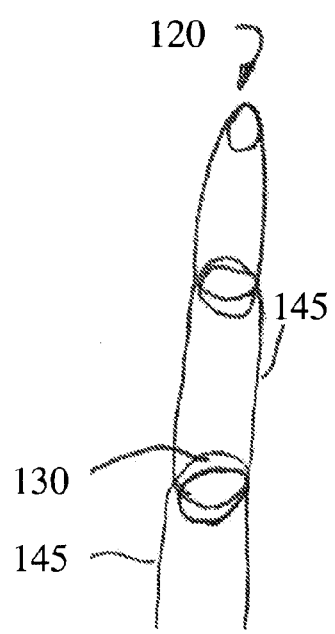 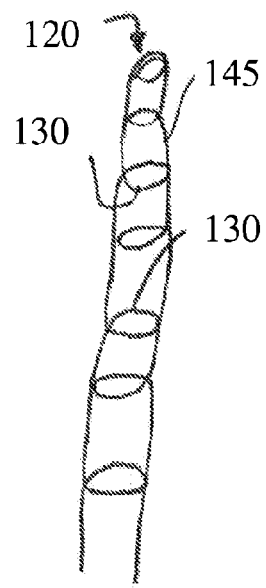
Fig. 11          Fig. 12

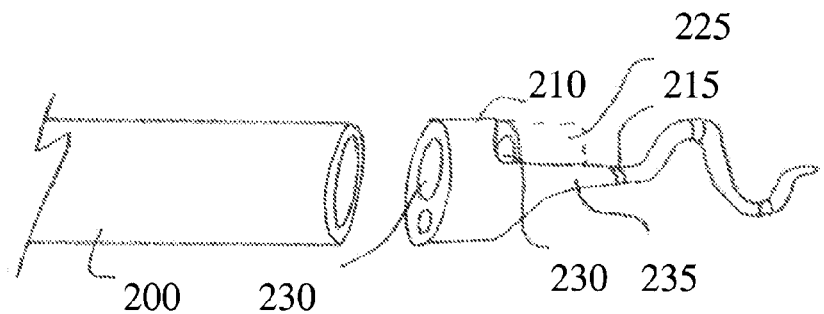
Fig. 26
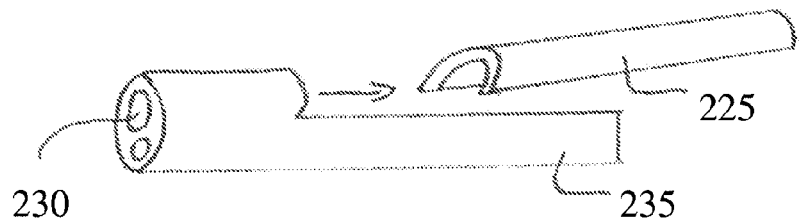
Fig. 27
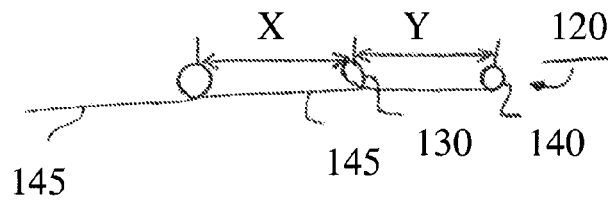
Fig. 28
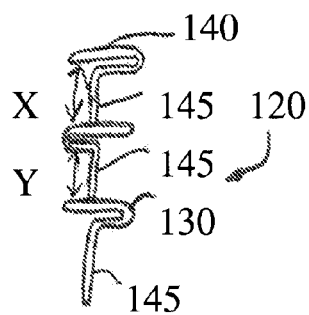 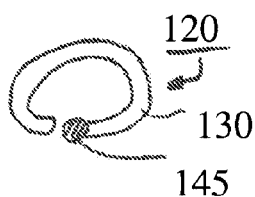
Fig. 29        Fig. 30

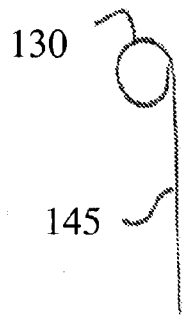
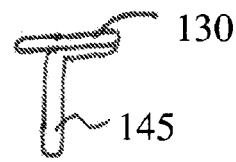
Fig. 31　　　　　Fig. 32
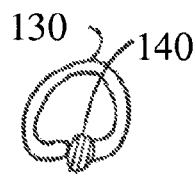
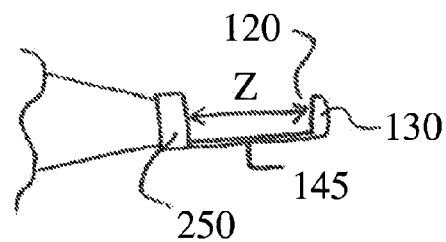
Fig. 33　　　　　Fig. 34
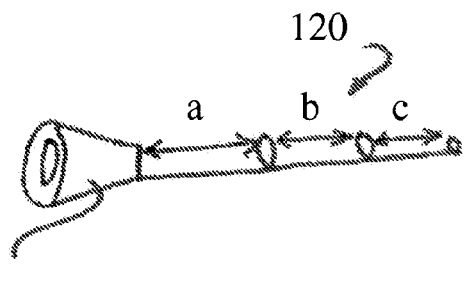
Fig. 35

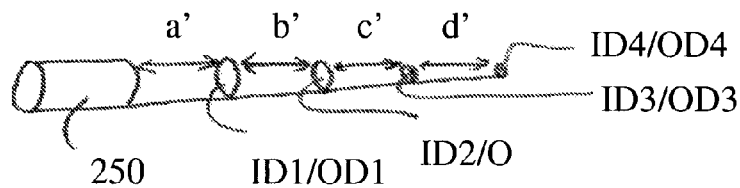
Fig. 36
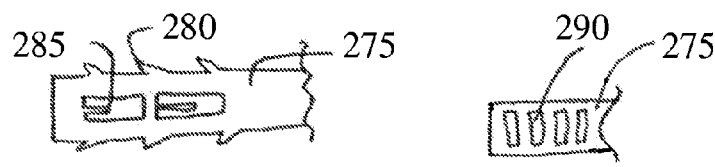
Fig. 37
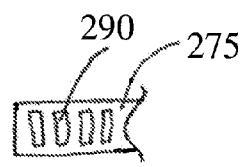
Fig. 38
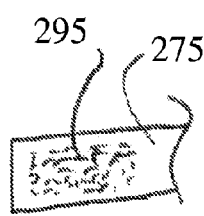
Fig. 39
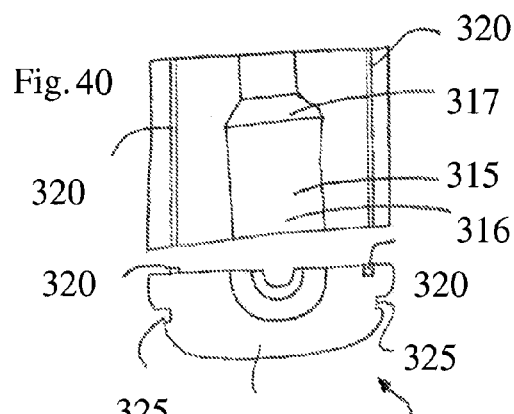
Fig. 40
Fig. 41

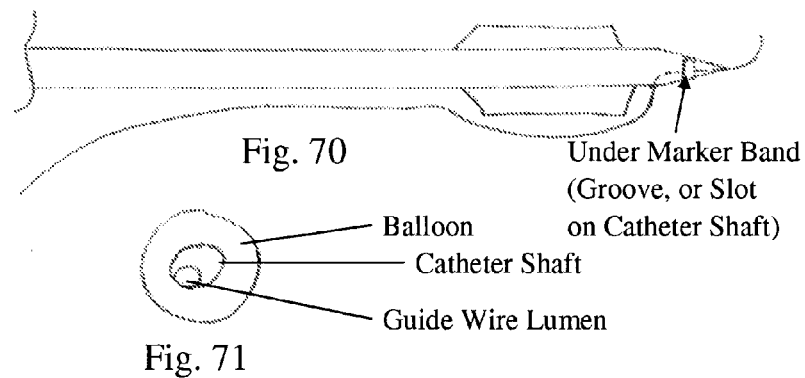
Fig. 70
Under Marker Band (Groove, or Slot on Catheter Shaft)
Balloon
Catheter Shaft
Guide Wire Lumen
Fig. 71
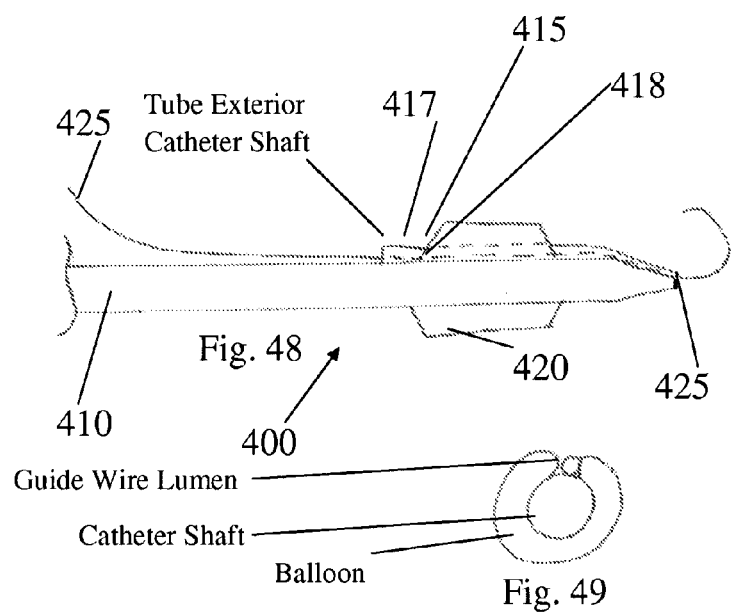
Fig. 48
Guide Wire Lumen
Catheter Shaft
Balloon
Fig. 49

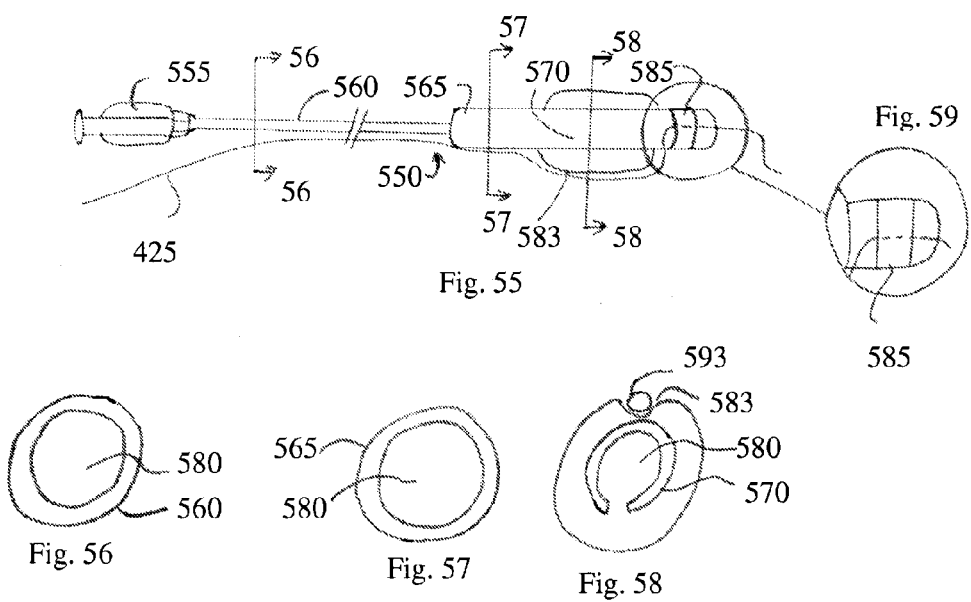

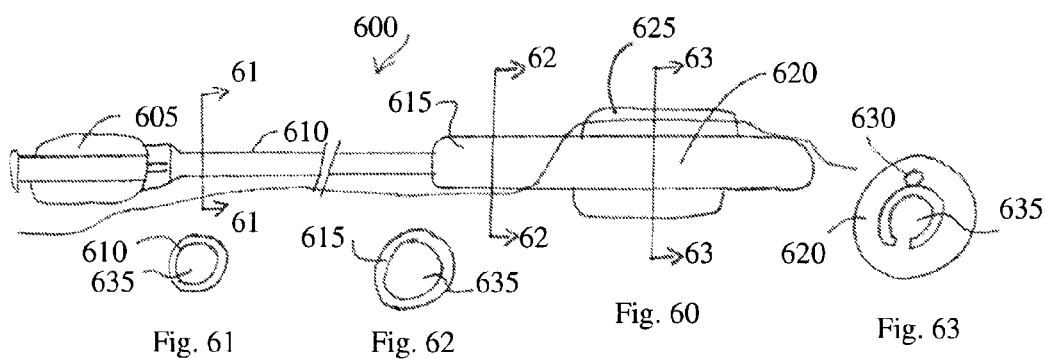
Fig. 61  Fig. 62  Fig. 60  Fig. 63
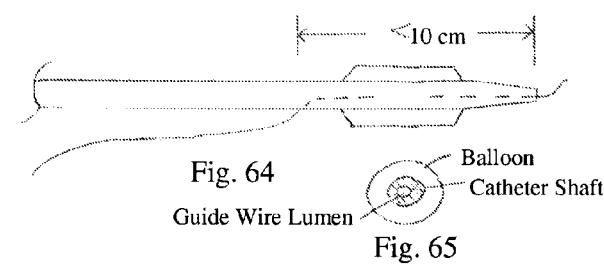
Fig. 64
Fig. 65
Guide Wire Lumen — Balloon — Catheter Shaft

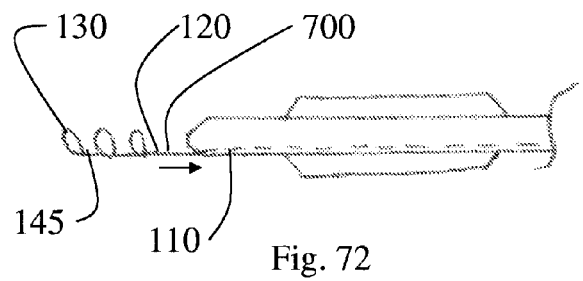
Fig. 72
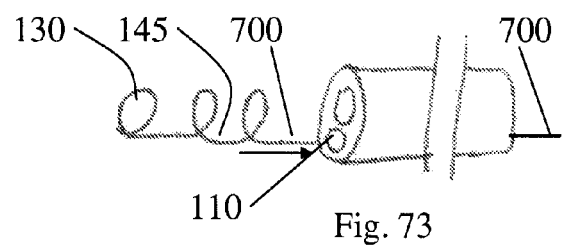
Fig. 73
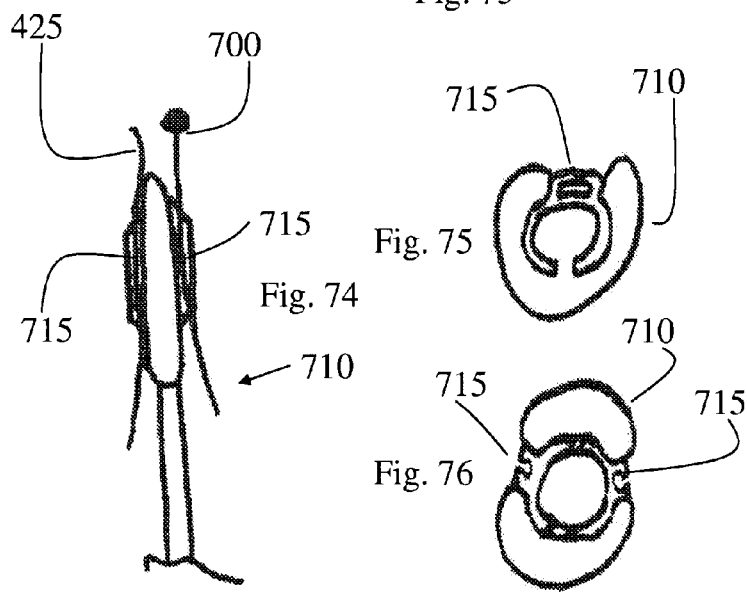
Fig. 74
Fig. 75
Fig. 76

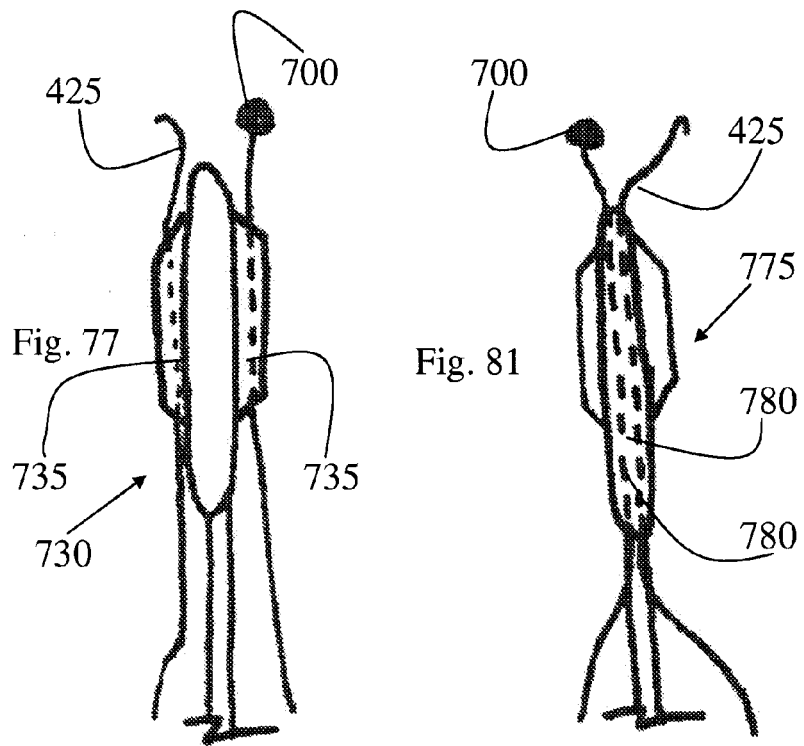
Fig. 77
Fig. 81
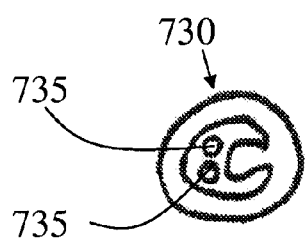
Fig. 78
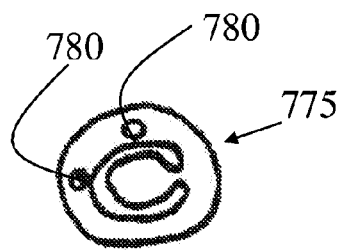
Fig. 80

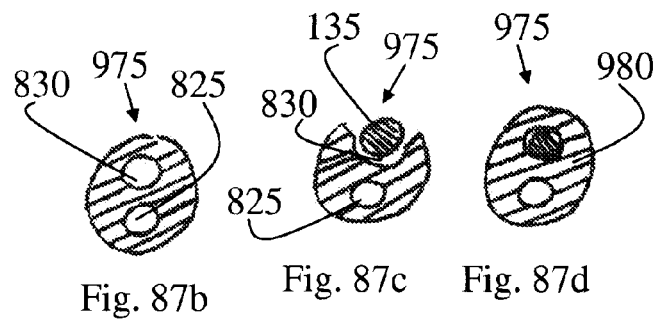
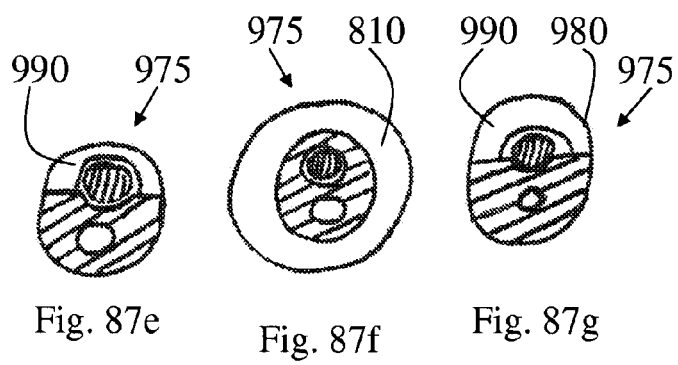
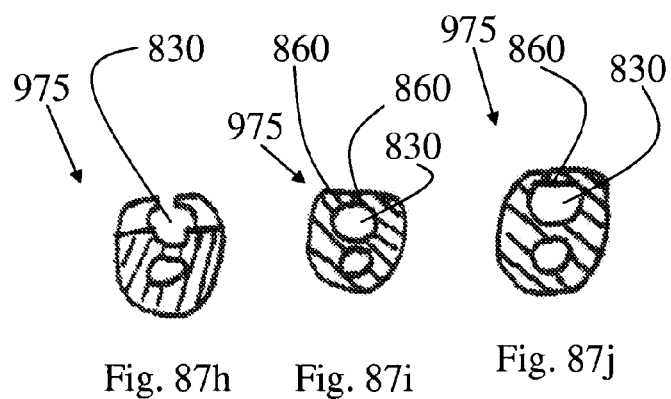
Fig. 87b  Fig. 87c  Fig. 87d
Fig. 87e  Fig. 87f  Fig. 87g
Fig. 87h  Fig. 87i  Fig. 87j

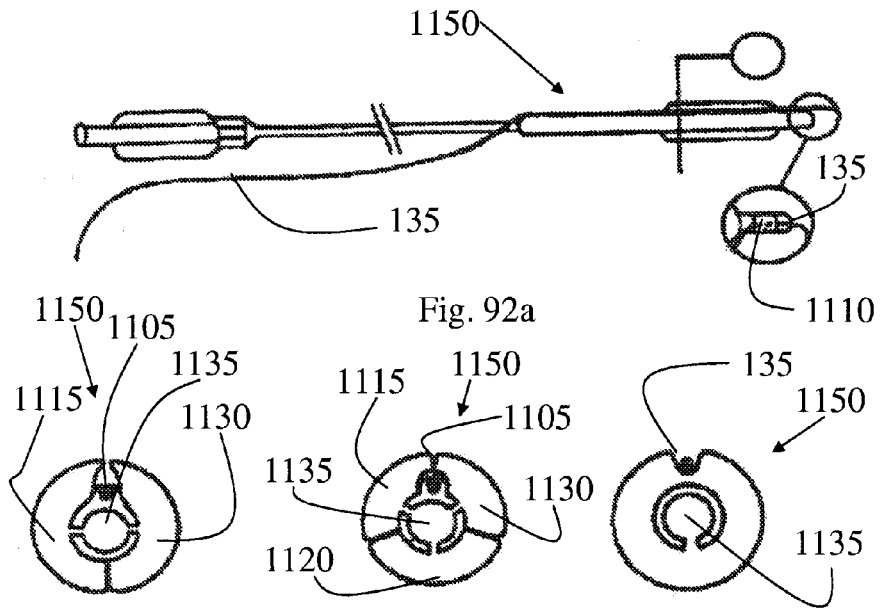
Fig. 92a
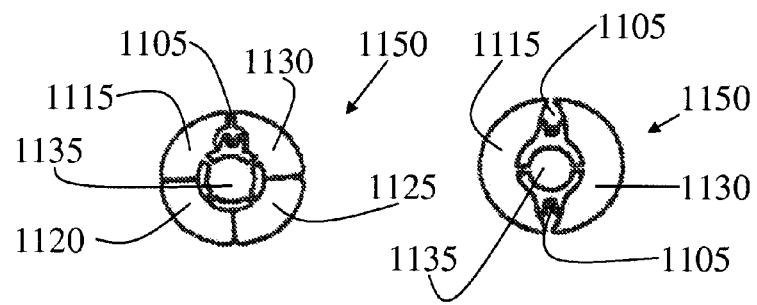
Fig. 92b    Fig. 92c    Fig. 92d
Fig. 92e    Fig. 92f

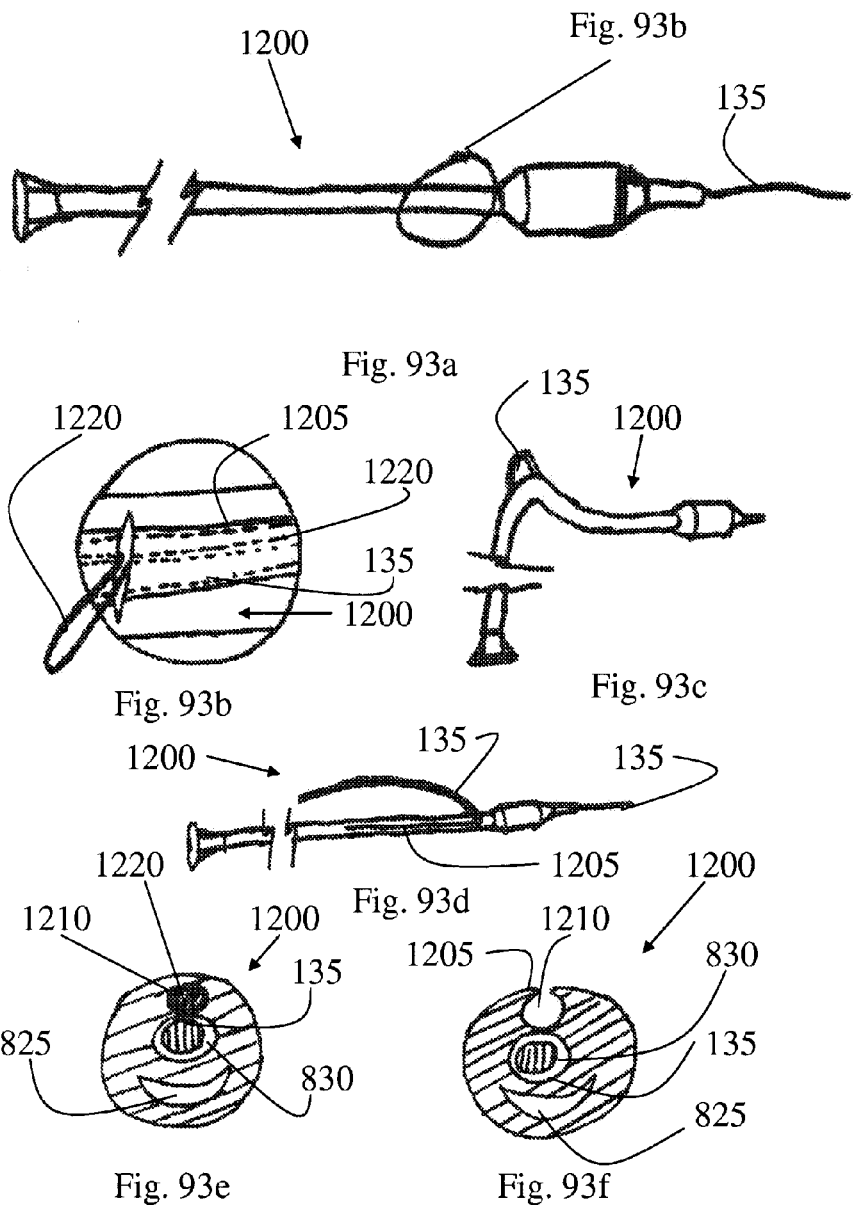

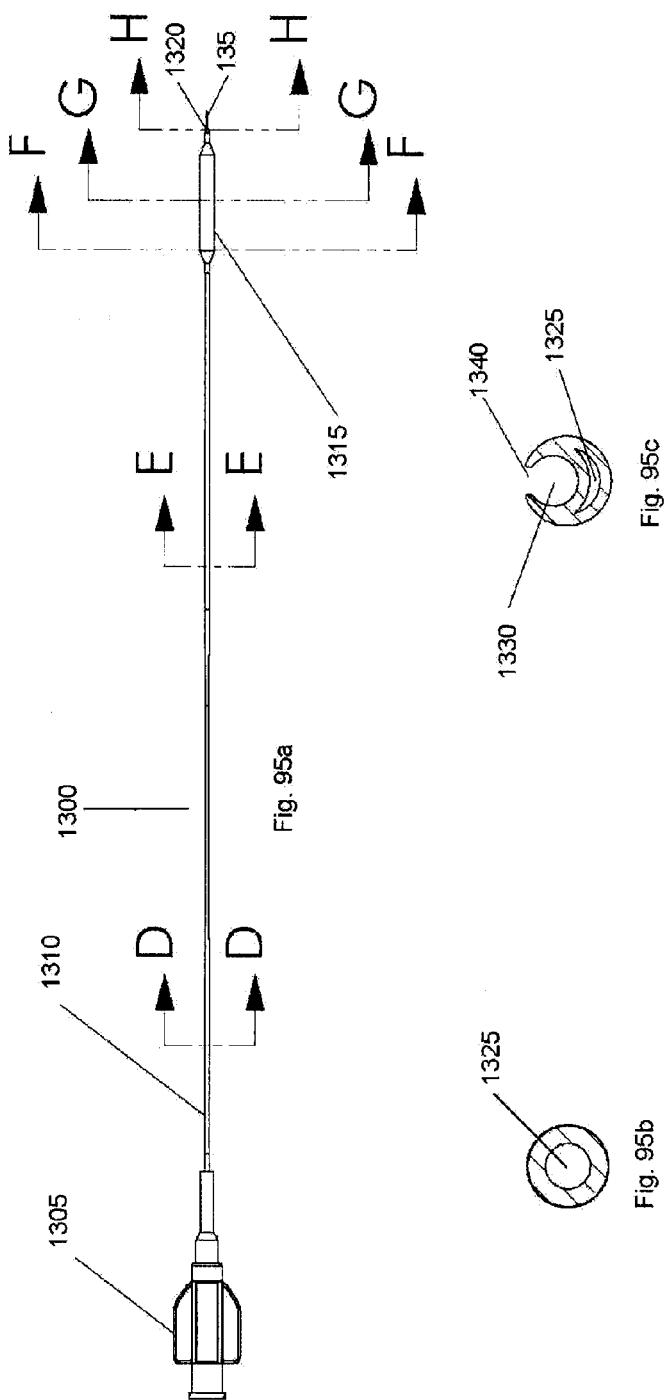

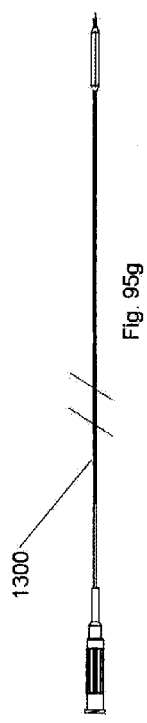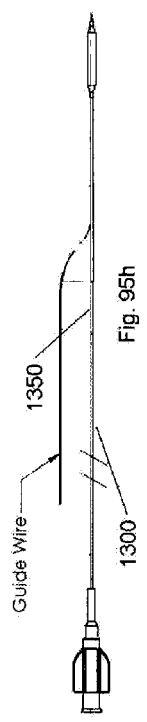

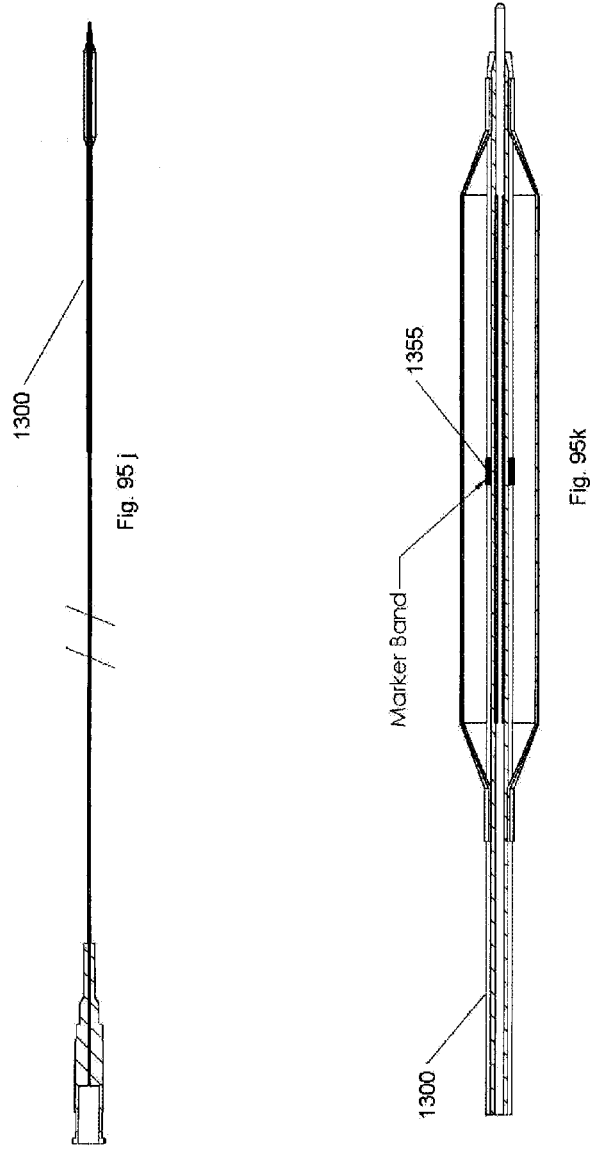

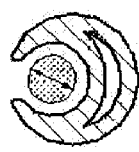
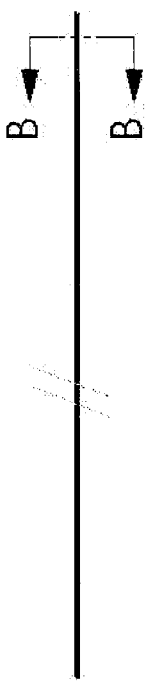
Fig. 95p
Fig. 95s
Fig. 95q
Fig. 95r

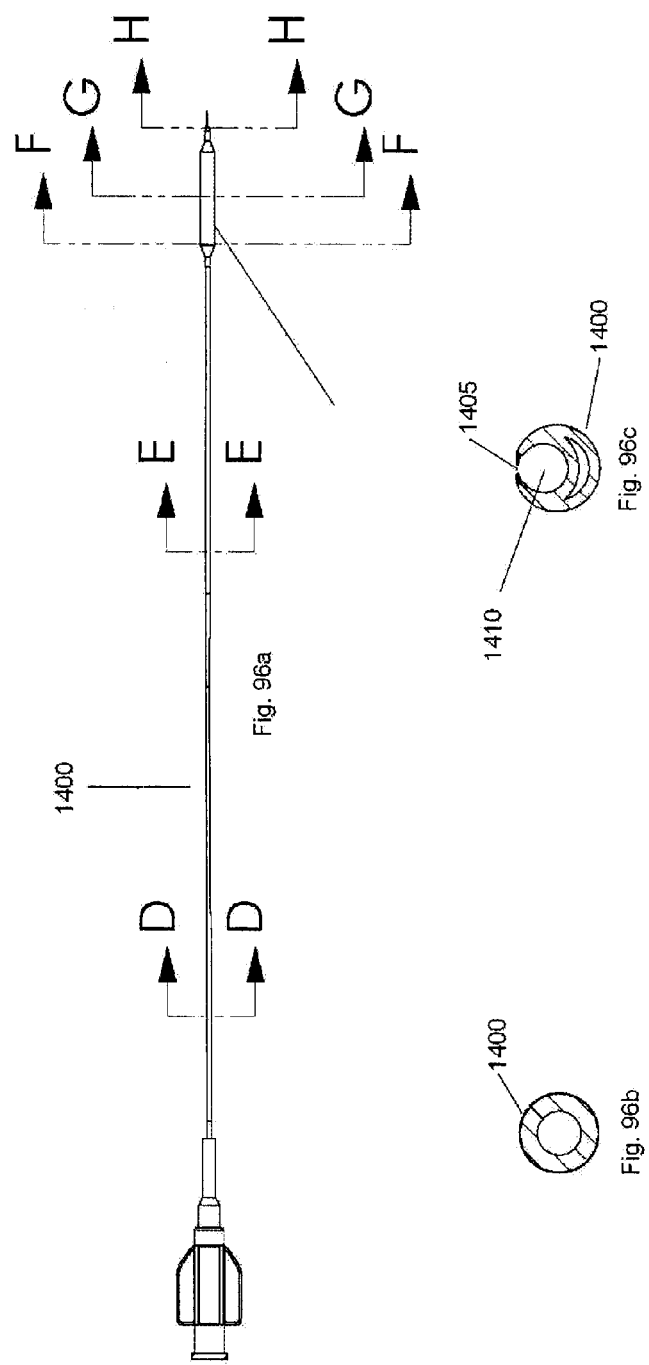

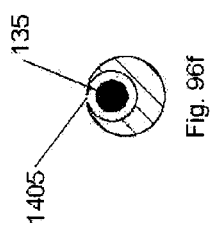
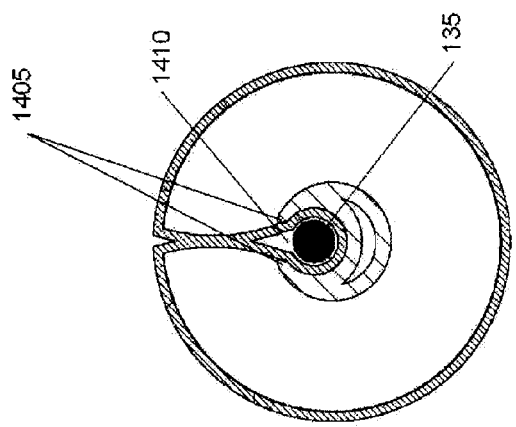
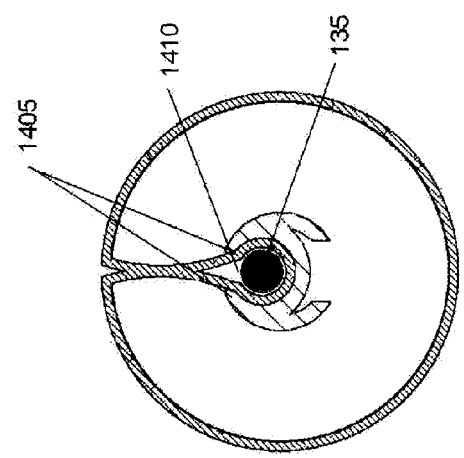

Guide Wire

Marker Band

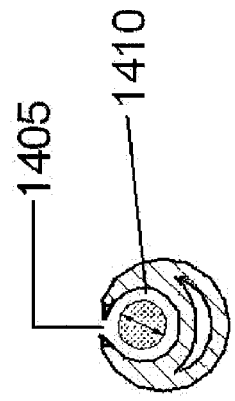
Fig. 96p
Fig. 96s
1405
1410
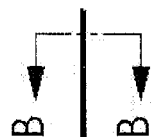
Fig. 96q
Fig. 96r

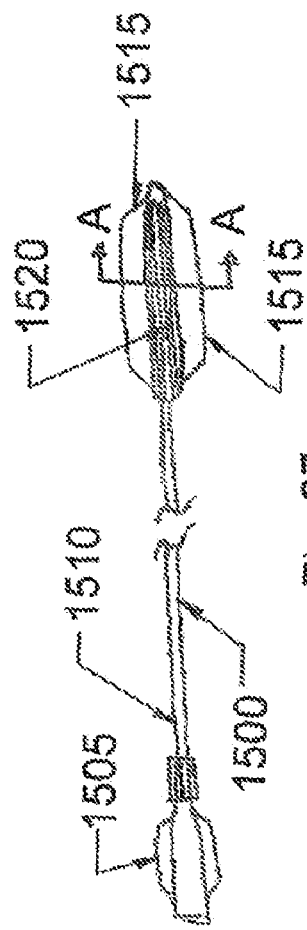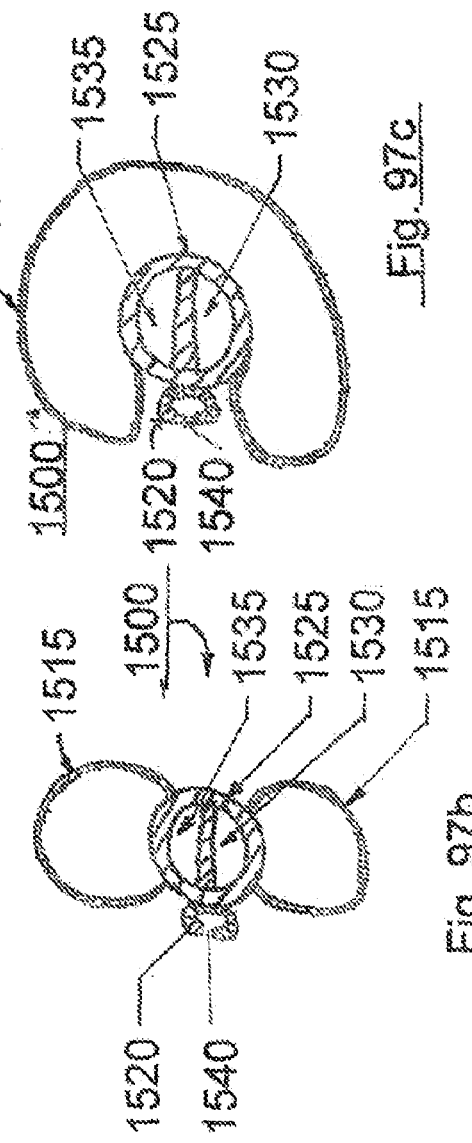
Fig. 97a
Fig. 97b
Fig. 97c

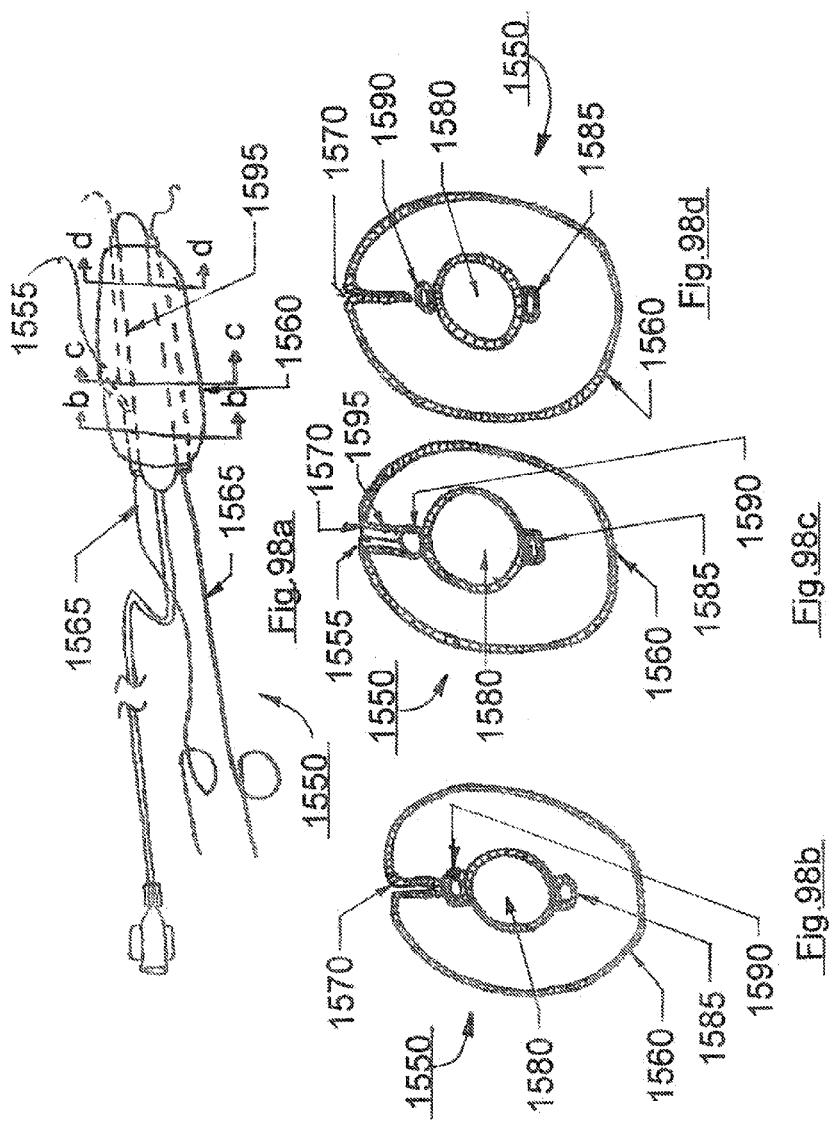

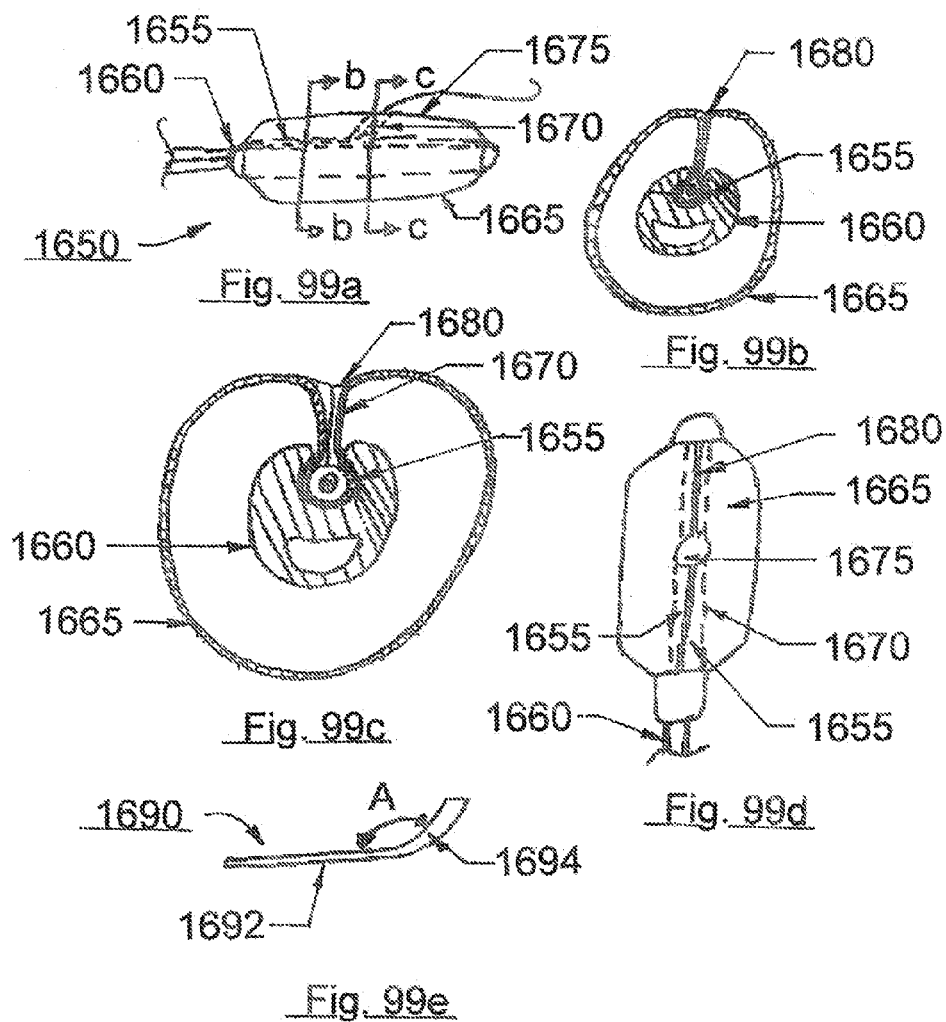

RAPID EXCHANGE CATHETER WITH STENT DEPLOYMENT, THERAPEUTIC INFUSION, AND LESION SAMPLING FEATURES

RELATED APPLICATIONS

This application claims priority from U.S. Provisional Patent Application No. 60/331,125, filed on Nov. 8, 2001, and titled Marker Catheter with Optional Rapid Exchange Capabilities, and U.S. Provisional Patent Application No. 60/347,291, filed on Jan. 14, 2002 and titled Slot for Directing a Wire along a Portion of a Tubular Vessel.

TECHNICAL FIELD

This invention relates to a rapid exchange catheter with multiple utilities for use inside mammalian tubular vessels or structures, and more particularly allows the catheter to be removed from around a guide wire by using a slot or channel to hold the guide wire.

BACKGROUND

During catheter-based procedures, the physician often visualizes the area being treated under fluoroscopy and visualizes the catheter and/or treatment area using radiopaque materials. One method of visualizing is to fabricate the catheter from a polymer that has been compounded with any of the radiopaque materials that are known in the art, such as barium sulfate, bismuth trioxide, bismuth subcarbonate, tantalum and/or other known combination of radiopaque additives. Another known method is to put one or more marker bands around the outer diameter of the catheter at various positions at the distal end of the catheter. The marker bands can be spaced at known distances along the length of the catheter such that a fluoroscopic procedure can be used to determine distances of, for example, a lesion. Contrast dyes also are used to visualize the treated area by injecting a contrast dye through the catheter while the fluoroscope is being operated. The physician then can see the vessel in which the catheter is positioned, as well as any lesion past which the contrast dye flows.

In the procedure, the physician may use a guiding device, such as a guide wire, to controllably reach the lesion or area to be treated. Once the guide wire is in position, the physician may need to pass one or more catheters, tubular devices, and/or medical devices along the guide wire to the lesion or treatment area The physician may pull the catheter or tubular device back along the guide wire and finally off of the guide wire. A difficulty of this, however, is that the guide wire must be very long (i.e., longer than the catheter) in order to pull the catheter off the guide wire without needing to first or also pull the guide wire out of the patient. A known solution to this problem is the use of a rapid exchange configuration in which the distal end of the catheter has a pair of opening into a lumen and through which the guide wire may be passed by inserting the proximal end of the guide wire through the distal most opening and then passing the proximal end of the guide wire out of the proximal opening of the lumen. For example, such a configuration is described by Yock (U.S. Pat. No. 5,451,233), which is incorporated by reference herein in its entirety.

One common application of rapid exchange and marker catheters is during coronary angioplasty, which refers to the use of an inflatable balloon to increase the blood flow through a stenosis (i.e., a partially blocked section of a blood vessel feeding the heart). A typical coronary angioplasty consists of three steps. First, a physician inserts a guiding catheter into a patient's blood vessel, typically through the femoral artery at the top of the patient's leg. The guiding catheter is advanced toward the heart through the patient's blood vessel, stopping short of the coronary arteries, and is then fixed in place. Next, the physician inserts a guide wire into the guiding catheter until the distal end of the guide wire exits the guiding catheter and enters the coronary artery. The physician then positions the guide wire across the stenosis to be treated in the coronary artery, and the guide wire is fixed in place. Finally, the physician advances a balloon catheter along the guide wire until the balloon exits the guiding catheter and is positioned across the stenosis. The physician then inflates the balloon to treat the stenosis, deflates the balloon, and removes the balloon catheter without disturbing the placement of either the guide wire or the guiding catheter.

Physicians frequently need to exchange balloon catheters during a single coronary angioplasty procedure. For example, if a stenosis blocks most of the blood flow through a vessel, the physician may first need to use a small balloon to increase the size of the opening through the stenosis, and then use a larger balloon to further increase the opening. Another example of a catheter exchange is when a physician uses a first balloon catheter to open a lumen and a second catheter to deploy a stent

SUMMARY

In one general aspect, a catheter is configured to be inserted into a vessel within a mammalian body. The catheter includes a tubular body, at least one channel extending along the tubular body; and a central lumen. The tubular body includes an exterior surface, a first end and a second end, and defines a length between the first end and the second end. The channel passes between a first opening and a second opening and includes a slot in the tubular body between the channel and the exterior surface of the tubular body such that a tubular member can be passed between the channel and the exterior surface. The slot extends from the first opening to the second opening and includes a pair of edges. The central lumen extends along the tubular body at least for a portion of the length of the tubular body.

Embodiments of the catheter may include one or more of the following features. For example, the catheter may further include a balloon extending around the tubular body proximal of the second end of the tubular body, at least a portion of the balloon being in contact with the exterior surface of the tubular body. The balloon may extend into the channel for at least a portion of the length of the channel. The balloon may further include a first surface extending from the channel and a second surface extending from the channel. Each of the first surface and the second surface may include a radially extending channel passing between the channel in the tubular body and an opening on an outer surface of the balloon. The catheter may further include a band encircling at least a portion of a circumference of the tubular body under the balloon.

The edges of the slot may overlap, be aligned and in contact along at least a portion of the length of the edges without being connected, or be aligned and spaced apart from one another.

The balloon may include at least two discrete diameters. The balloon may include a diameter that is tapered along a length of the balloon.

The catheter may further include a band encircling at least a portion of a circumference of the tubular body proximal of the second end of the tubular body. The channel may pass below the band.

In another general aspect, a catheter is configured to be inserted into a vessel within a mammalian body. The catheter includes a tubular body and at least one tube. The tubular body includes an exterior surface, a first end and a second end that define a length between the first end and the second end, and a central lumen extending along the tubular body at least for a portion of the length of the tubular body. The tube has an exterior surface and extends along the exterior surface of the tubular body at least for a portion of the length of the tubular body. The tube includes a first opening, a second opening, and a passage way passing between the first opening and the second opening.

Embodiments of the catheter may include one or more of the following features. For example, the catheter may further include a balloon extending around the tube and the tubular body proximal of the second end of the tubular body, at least a portion of the balloon being in contact with the exterior surface of the tubular body and the exterior surface of the t tube. The tube may include a channel that includes a slot opening into the passage way such that a tubular member can be passed between the channel and the exterior surface of the tube. The slot extends from the first opening to the second opening and includes a pair of edges.

The catheter may further include a band encircling at least a portion of a circumference of the tube proximal of the second opening of the tube.

The balloon may extend into the channel for at least a portion of the length of the channel. The balloon may further include a first surface extending from the channel and a second surface extending from the channel. Each of the first surface and the second surface may include a radially extending channel passing between the channel in the tube and an opening on an outer surface of the balloon. The catheter may further include a band encircling at least a portion of a circumference of the tube under the balloon.

The edges of the slot may overlap, be aligned and in contact along at least a portion of the length of the edges without being connected, or be aligned and spaced apart from one another.

The balloon may include at least two discrete diameters. The balloon may include a diameter that is tapered along a length of the balloon.

In another general aspect, a catheter is configured to be inserted into a vessel within a mammalian body and track a guide wire. The catheter includes a tubular body and at least one coiled member extending from the tubular body. The tubular body has an exterior surface, a first end and a second end, a length defined between the first end and the second end, and a central lumen extending along the tubular body at least for a portion of the length of the tubular body. The coiled member extends from the second end of the tubular body and includes one or more extension members and one or more loop members configured to receive a guide wire and defining an inner diameter of each loop. The loop members are connected to the extension members and define a first opening and a second opening Embodiments of the catheter may include one or more of the following features. For example, the catheter may further include a balloon extending around the tubular body proximal of the second end of the tubular body and being in contact with the exterior surface of the tubular body. The loop member may have a closed circumference. The closed circumference may be openable. The loop member may have an open circumference.

In another general aspect, a guide wire can be removed from a catheter. The method of removing a guide wire from a catheter includes providing a catheter that includes a tubular body, at least one channel extending along the tubular body, and a central lumen. The tubular body includes an exterior surface, a first end and a second end, and defines a length between the first end and the second end. The channel extends along the tubular body at least for a portion of the length of the tubular body. The channel passes between a first opening and a second opening and has a slot in the tubular body between the channel and the exterior surface of the tubular body. The slot extends from the first opening to the second opening and includes a pair of edges. The central lumen extends along the tubular body at least for a portion of the length of the tubular body. The method also includes inserting a guide wire into the channel, advancing the catheter along the guide wire, and removing the guide wire from the channel. Removing the guide wire includes passing the guide wire from the channel to the exterior surface of the tubular body through the slot in the tubular body. Embodiments of the method may include one or more of the features described above.

In another general aspect, a guide wire can be removed from a catheter. The method of removing a guide wire from a catheter includes providing a catheter that includes a tubular body and a tube. The tubular body includes an exterior surface, a first end and a second end, a length defined between the first end and the second end, and a central lumen extending along the tubular body at least for a portion of the length of the tubular body. The tube includes an exterior surface and extends along the exterior surface of tubular body at least for a portion of the length of the tubular body. The tube includes a first opening, a second opening, and a passage way passing between the first opening and the second opening. The method also includes inserting a guide wire into passage way in the tube through either of the first opening and the second opening in the tube, advancing the catheter along the guide wire through the tube; and removing the guide wire from the passage way. Removing the guide wire includes withdrawing the guide wire from the passage way through either of the first opening and the second opening in the tube. Embodiments of the method may include one or more of the features described above.

In another general aspect, a guide wire can be removed from a catheter. The method of removing a guide wire from a catheter includes providing a catheter that includes a tubular body and at least one coiled member. The a tubular body includes an exterior surface, a first end and a second end, a length defined between the first end and the second end, and a central lumen extending along the tubular body at least for a portion of the length of the tubular body. The coiled member extends from the second end of the tubular body and includes one or more extension members and one or more loop members configured to receive a guide wire and define an inner diameter of each loop. The loop members are connected to the extension members and define a first opening and a second opening. The method also includes inserting a guide wire into the loop member through either of the first opening or the second opening, advancing the catheter along the guide wire through the loop member, and removing the guide wire from the loop member. Removing the guide wire includes withdrawing the guide wire from the loop member through either of the first opening or the second opening. Embodiments of the method may include one or more of the features described above.

The catheters, marker attachment, band, and/or coil devices and techniques described herein can advantageously enable the physician to more accurately determine the length and diameter of a lesion. In this manner, the physician can properly size a subsequent step, secondary operation, or therapy, such as the placement and inflation of a balloon and/or stent to open and maintain the patency of a vessel. The catheters, marker attachment, band, and/or coil devices and techniques can advantageously facilitate rapid exchange over a guide wire, reduce or eliminate the need for a long guide wire, provide improved visualization of the device and/or lesion, and provide accurate measurement of, for example, the length and diameter of a lesion, such as in a coronary artery. In particular, they allow a physician to remove a catheter from around a guide wire. The catheters, marker attachment, band, and/or coil devices and techniques can advantageously provide accurate sizing of a secondary therapeutic device, such as a stent or balloon, to the lesion, is easy to use, provides rapid exchange between guide and diagnostic catheters, between diagnostic and therapeutic catheters or device, and between therapeutic devices of different sizes. The marker attachment, band, and/or coil devices and techniques can advantageously be fabricated as a separate stand-alone device that can be attached to commercially available catheters and devices at the time of use or during manufacture of the catheter Thus, the physician can decide at the time of a procedure to take a measurement and mount a marker attachment, band, or coil to, for example, an inexpensive off-the-shelf diagnostic, guide, infusion, or angioplasty catheter or device and take the measurement.

The rapid exchange catheter designs herein advantageously do not require an internal guide wire lumen, can allow complete removal of a catheter from around the side of a guide wire, can provide vessel access through an inflated balloon for several purposes including lesion sample access and retrieval, and can provide non-complete circumferential inflated balloon geometry. Non-complete circumferential geometry can advantageously provide alignment of the balloon void area with a calcified lesion so that the remainder of the vessel cross section can be safely dilated. This avoids putting excessive force on the hardened lesion, which in turn puts focused pressure on the wall of the artery at that site. A nonconcentric stent also may be loaded onto such a device to avoid a hardened lesion, while still supporting or reinforcing the remainder of the cross section of the vessel.

The catheter designs also may advantageously allow multiple guide wires to be used with the device for several purposes, including guiding a second catheter to a branched, or bifurcated section of an artery. Additional advantageous features include perfusion without the requirement of an internal catheter lumen as well as being compatible with devices such as those used for embolic protection. The designs also advantageously provide a device that can be produced as a separate component that can be used with other commercially available catheters, e.g., converting an Over-the-Wire (OTW) catheter to a Rapid Exchange (RX) catheter. The catheter designs can utilize a standard 0.014" guide wire as well as a hollow tipped-guide wire for tissue and lesion sampling and retrieval.

The details of one or more embodiments of the invention are set forth in the accompanying drawings and the description below. Other features, objects, and advantages of the invention will be apparent from the description and drawings, and from the claims

DESCRIPTION OF DRAWINGS

FIGS. 10–12 are perspective side views of a marker attachment with parallel extensions connecting the coils.

FIG. 26 is a perspective side view of a dual lumen, integrally formed marker attachment tip.

FIG. 27 is a perspective side view of the dual lumen attachment tip prior to formation of the coil.

FIGS. 28–30 are perspective side, top, and end views of an embodiment of a marker attachment with multiple marker coils configured to track a guide wire.

FIGS. 31–33 are perspective side, top, and end views of an embodiment of a marker attachment with a single marker coil configured to track a guide wire.

FIGS. 34–36 are perspective side views of an embodiment of a marker attachment with a mounting band or tip.

FIGS. 37–39 are top views of a mounting end of marker attachments.

FIGS. 40 and 41 are top and end views, respectively, of one side of a heated compression die for mounting a marker attachment to a catheter.

FIG. 48 is a side view of the catheter of FIG. 44 with an optionally closed guide wire channel.

FIG. 49 is a cross-sectional side view of the shaft of the catheter of FIG. 48 taken that at the distal end of the catheter and shown at the point where the balloon and the guide wire slot are adjacent to each other.

FIG. 55 is side view of a rapid exchange catheter having a detent or groove with an option guide passage tube.

FIGS. 56–59 are cross-sectional side views of the catheter shaft taken at points A, B, C, and distal tip, respectively, of the catheter of FIG. 55.

FIG. 60 is a side view of a catheter having an embedded guide wire passage between an inflatable balloon and the catheter shaft.

FIGS. 61–63 are cross-sectional side views of the catheter shaft taken at points A, B, and C, respectively, of the catheter of FIG. 60.

FIGS. 64–71 are various side and cross-sectional shaft views of rapid exchange and marker catheters FIGS. 72 and 73 are side and perspective side view, respectively, of a marker catheter formed using a reinforcing wire as a shaft component for pushability, as a radiopaque marker, and as a rapid exchange member FIGS. 74–76 are a side and two cross-sectional shaft views, respectively, of a catheter having one or more slots for rapid exchange of the guide wire and passage of a therapeutic or protective device.

FIGS. 77 and 78 are side and cross-sectional shaft views, respectively, of a rapid exchange catheter having one or more passages in the catheter shaft wall for passage of a guide wire and passage of a therapeutic or protective device.

FIGS. 80 and 81 are side and cross-sectional shaft views, respectively, of a catheter having one or more passages in the catheter shaft wall for passage of a guide wire and passage of a therapeutic or protective device.

FIGS. 87a–87j are side and cross-section side views of a catheter having one or more guide sections

FIGS. 92a–92f are side and cross-sectional views of a second balloon catheter having a second implementation of a slotted guide wire/perfusion channel, a marker band, and a balloon with one or more compartments.

FIGS. 93a–93f are side and cross-section views of a catheter that includes a peelable guide wire opening.

FIGS. 97a–97e are side and cross-sectional views of a catheter that includes one or more guide wire channels and one or more balloons.

FIGS. 98a–98d are side and cross-sectional views of a catheter that includes a radially extending channel formed in a fold in a balloon and extending from a guide wire channel to a side port in the balloon

FIG. 99a is a side view of the balloon portion of a catheter showing hidden views and a radially extending channel formed in balloon folds FIGS. 99b and 99c are cross-sectional side views of the balloon portion of the catheter of FIG. 99a taken along section lines b—b and c—c.

FIG. 99d is a top view of the balloon portion of the catheter of FIG. 99a.

FIG. 99e is a side view of a cylindrical member used to form the radially extending channel of FIG. 99a.

Like reference symbols in the various drawings indicate like elements.

DETAILED DESCRIPTION

Figure 1:
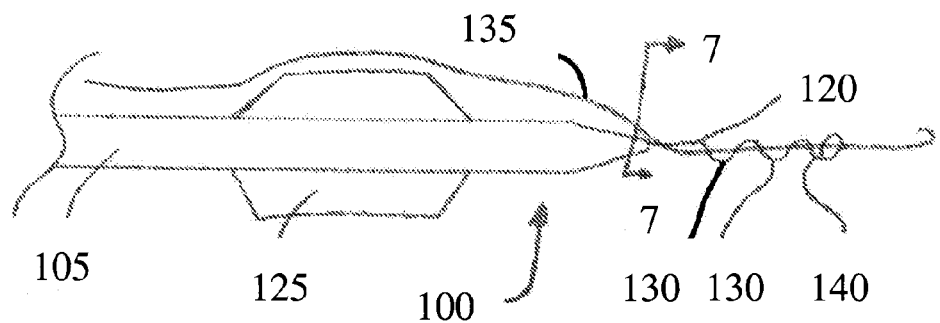
FIG. 1 is a perspective side view of a first embodiment of a marker catheter.
Figure 2:
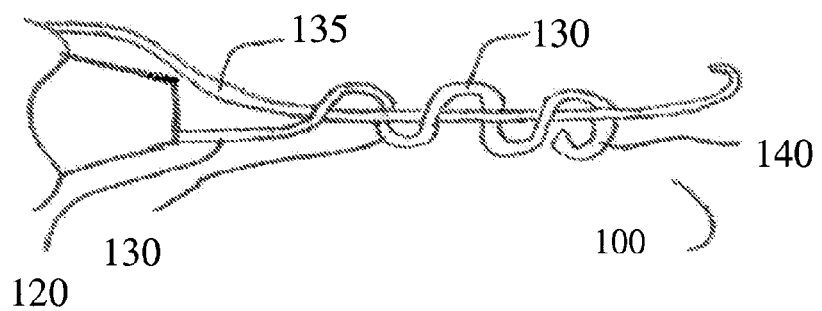
FIG. 2 is a perspective side view of an open coil marker attachment.
Figure 3:
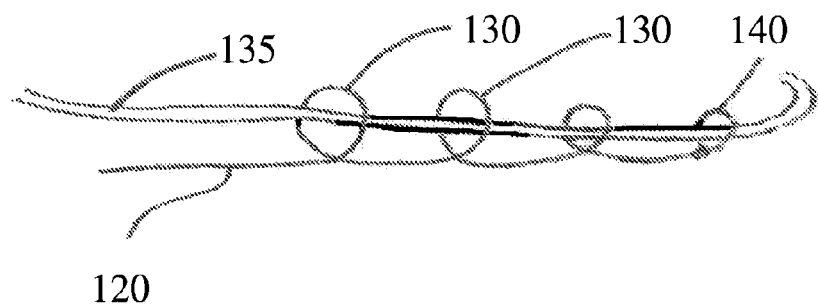
FIG. 3 is a perspective side view of a closed coil marker attachment.

FIGS. 1–7 illustrate an example of a rapid exchange catheter 100 that also can be easily installed over a guide wire or other tubular guiding device, or any other catheter that utilizes a guide wire. The rapid exchange catheter can be used in a variety of procedures, including orthopedic, gastrointestinal, cardiovascular, and radiological. Specific cardiovascular uses include percutaneous coronary transluminal angioplasty ("PTCA"), stent placement, graft deployment (e.g., aortic replacement or reinforcement), and/or therapeutic infusion The marker catheter 100 is configured as a balloon catheter and includes a tubular body 105, a mounting lumen 110, a central lumen 115, a marker attachment 120, and an inflatable balloon 125. The tubular body 105 can be fabricated from any medical grade polymer, including any well known polymer, such as nylon, polyethylene, Pebax™, polyimide, polyamide, polyester, polypropylene, and/or any combination of these or other suitable materials. The shaft of the tubular body optionally can be reinforced using a polymer, a metal, a metal alloy (e.g., nitinol, stainless steel, Elgiloy™, inconel, 17-7 PH™), and/or any combination of these or other suitable materials. The shaft also can be reinforced, or separately reinforced, using a reinforcing component or technique, such as one or more wires having a shape that is round, flat or of another geometry; multiple tubing layers, with or without a tie, or bonding layer, a mandrel; a hypotube; by irradiation, using variable wall thickness; and/or any combination of these or by another suitable reinforcing components and techniques. Reinforcing shaft components can include a mandrel, a hypotube, or any other article that can be used inside the shaft, outside the shaft, or be used as the catheter shaft itself, or other configuration. The reinforcing shaft components can be movable, removable, or fixed. The reinforcement can be along the entire length, or a partial length at selected locations, and can be used to improve catheter trackability, pushability, and provide a strain relief transition between bonded catheter segments. The tubular body 105 can be formed using any of the known methods of fabricating tubular bodies, including extrusion (single or multiple layer), casting, injection molding, dip coating, and/or any combination of these methods or other known, suitable fabrication processes or methods. The tubular body 105 also can be reinforced by using a coil, braid, wrap, combination of these reinforcement configurations, or any other suitable process, configuration, or method.

The marker attachment 120 extends from the mounting lumen 110 from the distal end of the marker catheter 100 (FIGS. 6 and 7) and includes a coil or loop configuration with one or more coils or loops 130. The coils or loops 130 are placed apart from each other at a known distance or distances. For example, if there are more than two coils 130 the first two coils can be a first distance apart and the distance between the second and third coils can be a second distance apart. If there are additional coils, the marker attachment can be configured to have additional known distances.

Figure 4:
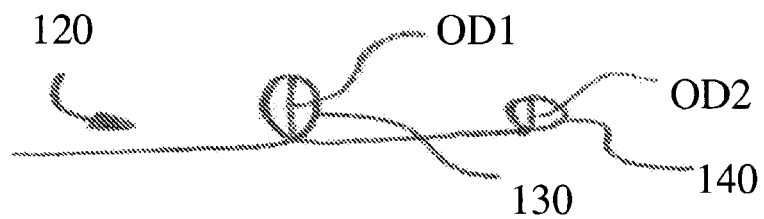
FIG. 4 is a perspective side view of a closable coil marker attachment.
Figures 5, 6:
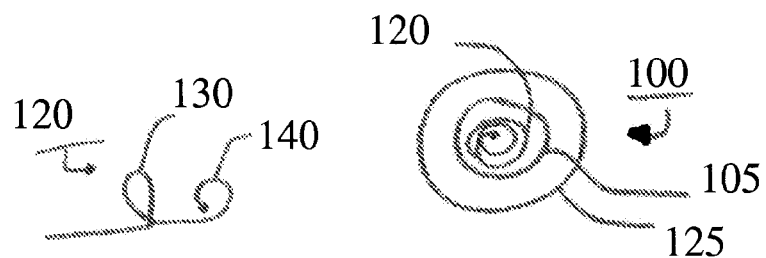
FIG. 5 is a perspective side view of the closable coil marker attachment of FIG. 4 with the closable coil being partially opened.
FIG. 6 is an end view of the marker catheter of FIG. 1.
Figure 7:
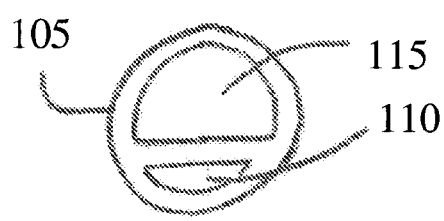
FIG. 7 is a cross-sectional end view of the tubular body/catheter shaft of the marker catheter of FIG. 1.

The coils 130 also are open such that a physician can easily place the marker attachment 120 over, and remove from, a guide wire 135 without having to slide the catheter 100 all the way to the proximal end of the guide wire 135 or slide the catheter from the proximal end of the guide wire. The distal-most coil 140 can be open (FIG. 2), closed (FIG. 3), or closable (FIG. 4). For example, the open coil configuration (FIG. 2) is formed without any closed loop so that the guide wire can be inserted into the coils. The distal end of the coil can be configured as a blunt end or an end that is turned back towards the distal end of the catheter so that it does not puncture a vessel while sliding along a guide wire. Of course, the distal end and the coil itself can be configured to advance through a lesion or vessel occlusion based on an advancing force and a simultaneous rotational or twisting force. The closed coil configuration (FIG. 3) may have open coils along its length and a closed distal coil or closed coils along its length and a closed or open distal coil. The coil is closed, by, for example, soldering the end of the coil to itself, using an adhesive to adhere the end of the coil to itself, or by forming a micro loop at the end such that it can be positioned around the coil. If the coils 130 are closed, the guide wire is inserted through the coils by inserting the proximal end of the guide wire through the coils. This configuration ensures that the marker attachment 120 will not release from the guide wire The closable coil (FIG. 4) is formed by bending the coil such that it contacts itself but can be flexibly bent to open the coil (FIG. 5). In this manner, the physician can easily mount the marker attachment or remove the marker attachment from a guide wire at any position along the guide wire's length. The marker attachment can be fabricated from a flexible metal, polymer, or combination. To visualize the marker attachment under fluoroscopy, the metal or polymer must be radiopaque. For example, the polymer can be compounded with any known radiopaque additive or material, as described above, and as is well known in the art of catheter design and fabrication. A radiopaque material may be deposited, or applied to the coil using ion deposition, sputter coating, spraying, dipping, or any combination of these or other suitable methods. The outer diameter of the coils 130 also can vary along the length such that each coil has a different outer diameter and can be used to gauge the diameter of, for example, a lesion. As illustrated in FIG. 4, the proximal most coil can have a first outer diameter and the distal most coil can have a second, smaller outer diameter. The marker catheter can be advanced into the lesion until it cannot be advanced further because one of the two or more coils reaches a diameter of the lesion that is narrower than the outer diameter of one of the coils.

Figure 8:
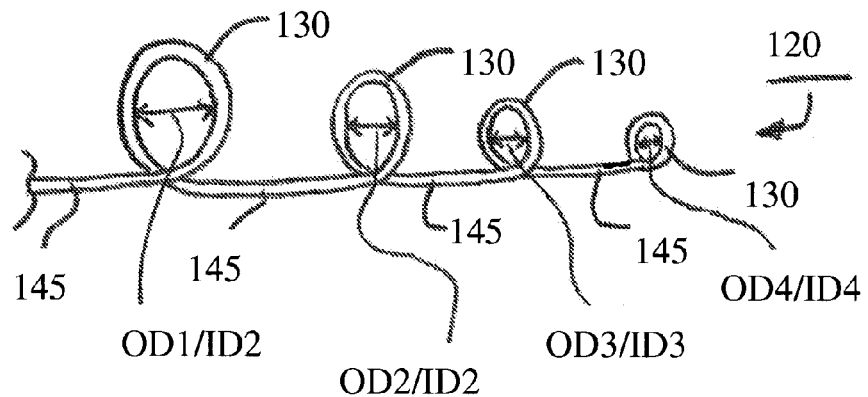
FIG. 8 is a perspective side view of a marker attachment with a staggered profile.

Referring to FIG. 8, in another embodiment of the marker attachment, the coils 130 can be arranged such that each marker attachment is formed from one or more extensions 145 connecting one or more coils The coils can be of decreasing inner and outer diameter such that consecutive extensions 145 are staggered inwardly or outwardly in a step-wise manner. If the outer diameter of the individual coils 130 is known, advancing the marker attachment into the lesion will permit the physician to size the inner diameter of the lesion based on which coil is unable to proceed further into the lesion. Moreover, because the coils 130 are spaced apart known distances, the physician will be able to gauge the length of the lesion, as well as the inner diameter of the lesion.

Of course, the coils 130 all can be of the same outer and inner diameter with an inner diameter that is slightly larger than the outer diameter of the guide wire, and the marker attachment material being made of a thin diameter metal or polymer wire or tube. In this manner, the marker attachment has a minimized profile, optionally less than the outer diameter of the catheter to which it is attached.

Figure 9:
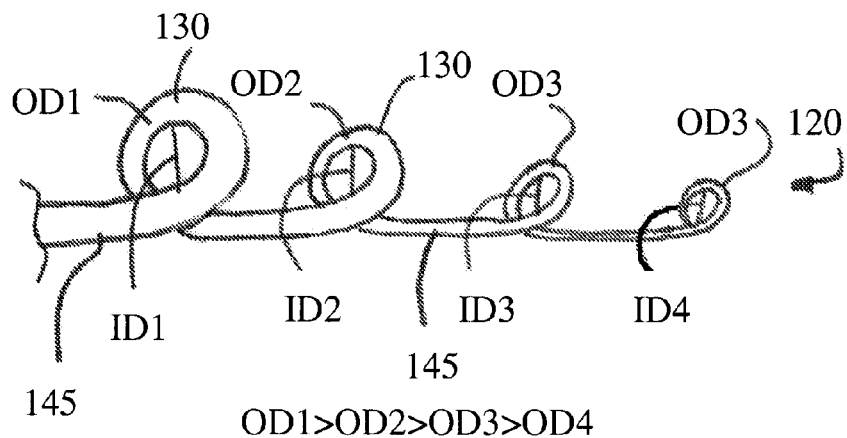
FIG. 9 is a perspective side view of a marker attachment having a reduced diameter wire and constant inner diameters of the coils.

Referring to FIG. 9, in another embodiment, the marker attachment 120 can be fabricated from a wire or tube that has been drawn to have a decreasing diameter along its length. The marker attachment can be formed, for example, by using a nitinol or other shape memory or superelastic wire or tube that can be wrapped around a constant diameter mandrel and heat formed into that configuration using techniques that are well known in the art for fabricating articles from shape memory or superelastic metals such as nitinol The marker attachment embodiment of FIG. 9 will have coils 130 having a constant inner diameter but a changing outer diameter along its length, for example, an outer diameter that is decreasing from the proximal end to the distal end of the marker attachment 120.

Other configurations and embodiments of the marker attachment 120 are illustrated in FIGS. 10–14. FIGS. 10–12 illustrate embodiments of marker attachments with parallel extensions 145 connecting the coils 130. The marker attachment 120 can be formed by taking a single wire or tube, such as a nitinol wire or tube, and wrapping coils 130 separated by extensions 145 along the mandrel's length. At the distal most coil 130, the wire or tube can be reversed in direction to form extensions 145 that are parallel to the already formed extensions and coils 130 that are adjacent to the already formed coils (FIG. 9). Alternatively, the wire or tube can be reversed in direction to form coils 130 that are adjacent to the already formed extensions and extensions that are adjacent to the already formed coils. These techniques can be selected to adjust the flexibility of the marker attachment to track a guide wire or guiding device. The marker attachment then can be heat formed into that configuration using techniques that are well known in the art for fabricating articles from shape memory or superelastic metals such as nitinol.

Figure 13:
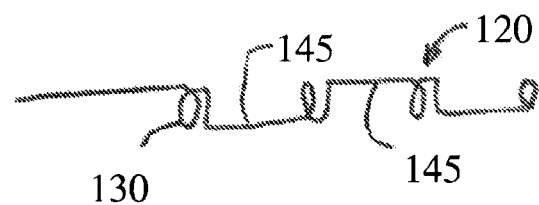
FIGS. 13 and 14 are perspective side views of increased flexibility marker attachments with alternatively placed extensions connecting the coils.
Figure 14:
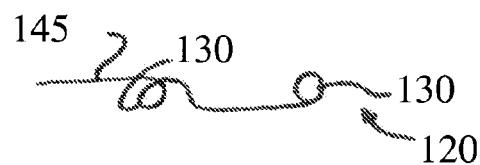
Figure 15:
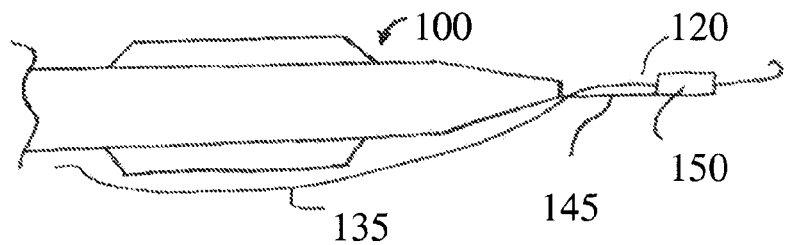
FIG. 15 is a perspective side view of a catheter with a radiopaque tube marker attachment.

FIGS. 13 and 14 illustrate embodiments of marker attachments 120 that have alternatively placed extensions 145. The marker attachments of FIGS. 13 and 14 can be formed, for example, by wrapping a wire or tube one and one-half times around a mandrel and then forming an extension 145, wrapping the wire or tube one and one-half times around the mandrel, and so on until the desired number of coils 130 and extensions 145 are formed. This configuration provides increased flexibility of the marker attachment. Although FIGS. 13 and 14 are shown with the inner diameter and the outer diameter of the coils 130 being the same, the can be varied to use any of the configurations described above for providing a gauge of the inner diameter and the length of the lesion into which the marker attachment is inserted or passed.

Referring to FIGS. 15–22, the catheter 100 can be implemented with a marker attachment 120 that includes a radiopaque tube 150 mounted to the extension 145. The radiopaque tube 150 can be a metal or polymer tube having an inner diameter, an outer diameter, and a channel passing between a pair of openings. This marker attachment tracks a guide wire smoothly and also provides rapid exchange for the physician. The inner diameter, the outer diameter, and the length of the radiopaque tube 150 can be sized according to any of the configurations described above. For example, the inner diameter of the radiopaque tube can be slightly larger than the inner diameter of the guide wire over which it will be tracked. The outer diameter of the radiopaque tube can be constant or varied. For example, the outer diameter of the tube can gradually transition or use step transitions to go from a first known, smaller diameter at the distal end to a second known, larger diameter at the proximal end. This will help to gauge the length and inner diameter of a lesion. The tube also can be of a known length to provide a gauge to size the length of a lesion.

One end of the extension 145 can be mounted on the outer surface of the tube 150, the inner diameter of the tube, or to the wall surface formed between the inner and outer diameters. Of course, the extension 145 and the tube 150 can be formed as a single piece, for example by casting, machining, or other material removing operation, such as etching or electron discharge machining. The extension 145 and/or tube 150 also can be fabricated from a radiopaque polymer that has been loaded with a radiopaque additive or material.

Figure 16:
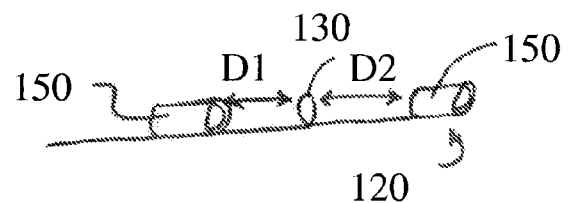
FIGS. 16 and 17 are perspective side views of marker attachments with radiopaque tubes and coils.
Figure 17:
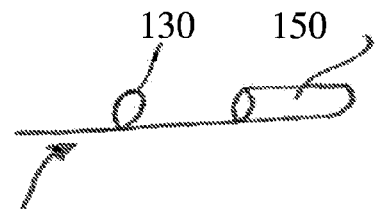
Figures 20, 21:
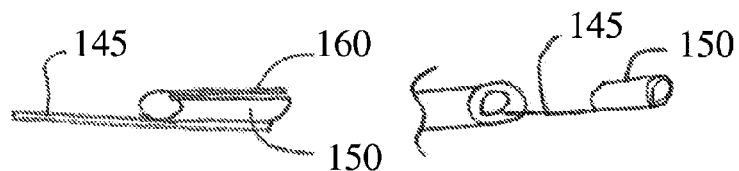
FIG. 20 is a perspective side view of a marker attachment with a slotted radiopaque tube.
FIG. 21 is a perspective side view of a catheter with a marker attachment mounted to the distal end of the catheter.

Various configurations of the radiopaque tube 150 and the coils 130 described above are possible. For example, the marker attachment can be formed with a single coil 130 and a pair of radiopaque tubes 150 (FIG. 16). The coil can be positioned between or on either side of the tubes. The marker attachment also can be formed with a single coil (FIG. 16) and a single radiopaque tube 150 (FIG. 17). The radiopaque tube also can be fabricated without a complete circumference, for example, as a slotted radiopaque tube. For example, a percentage of the circumference of the tube can be open with a slot 160 so that, for example, a guide wire can be pressed through the slot 160 into the channel in the tube. This facilitates rapid exchange of the guide wire (FIG. 20). Although the term channel is used throughout this application to refer to a passage way with an opening along at least one portion of the passage way, the term channel also encompasses a slot, groove, opening, detent, cross-sectional voids, or other configurations that have do not have a complete circumferential closure at least at one potion along the length of the passage way.

Figure 18:
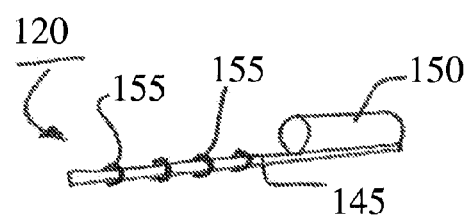
FIGS. 18 and 19 are perspective side views of marker attachments with radiopaque bands.
Figure 19:
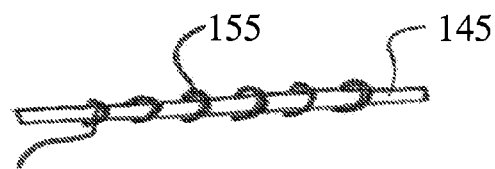

If the extension 145 and the tube 150 are formed from a non-radiopaque material, such as a polymer without radiopaque additives, radiopaque gauge or marker bands 155 can be placed along the length of the extension 145 at known distances so that they can be visualized under fluoroscopy (FIG. 18). The extension also can be formed without the tube 150 and use just the marker bands 155 mounted on the flexible extension 145 (FIG. 19).

Figure 22:
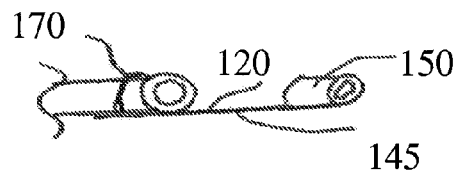
FIG. 22 is a perspective side view of a catheter with a marker attachment mounted to the distal end of the catheter with an attachment band.

The marker attachment using a radiopaque tube, as well as the other marker attachments described herein, can be used on any tubular device. In the cardiovascular field, the marker attachments can be used, for example, on guide catheters, diagnostic catheters, infusion catheters, etc. As illustrated in FIGS. 21 and 22, the marker attachment with the radiopaque tube 150 is mounted to a catheter that does not have an inflatable balloon. The marker attachment can be mounted to the inner surface, the outer surface, the edge wall, or into the wall or between layers of the catheter (FIG. 21). For example, the marker attachment can be formed as part of a tip in a first operation and that tip is fused to the distal end of the catheter in a subsequent operation. The marker attachment also can be mounted to the catheter by using an attachment band 170 to hold the extension 145 to the catheter 100

Figure 23:
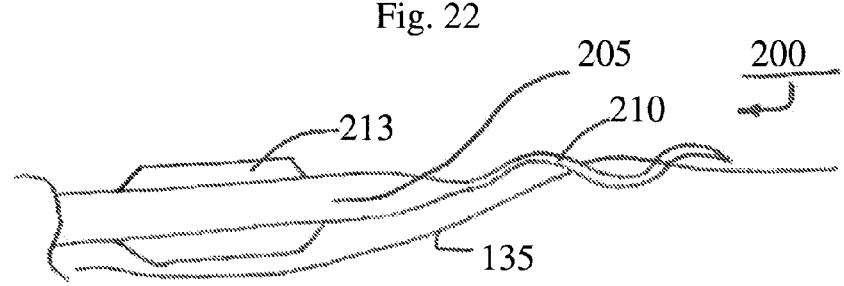
FIG. 23 is a perspective side view of a catheter with an integrally formed marker attachment.
Figure 24:
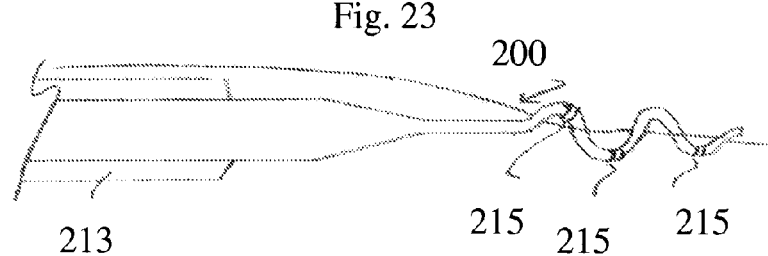
FIG. 24 is a perspective side view of a catheter with an integrally formed marker attachment with marker bands.

Referring to FIGS. 23 and 24, a catheter 200, which may be implemented as an inflatable balloon catheter, a guiding catheter, a diagnostic catheter, an infusion catheter, etc., includes a shaft 205 and a coiled tip 210 The tip is coiled to track a guide wire with the capability of being rapidly exchanged because of the coil shape. The coiled tip 210 is formed separately and subsequently attached to the shaft or formed integrally with the shaft 205. For example, to form the tip integrally, the distal end of the shaft is inserted into a hot die to compress and shape the tip into a coiled shape. The heat and compression impart a usable balance between flexibility and stiffness on the coiled tip so that the coiled tip will track a guide wire but not be so flexible that it falls off and not be so stiff that it damages the tubular vessel in which it is inserted. The coiled tip also can be formed by drawing down the shaft over a mandrel to impart the coiled shape. The coiled tip also can be formed by placing a shaped thin wire or tube within the distal end of the shaft and heating the distal length of the shaft to shrink it over the thin wire or tube so that the distal end of the shaft is imparted the shape of the wire or tube. The wire or tube can be made from, for example, a shape memory or superelastic metal, such as nitinol. The wire or tube can be straight at the first cooler temperature in which it is inserted into the shaft and then when the shaft is heated, for example, by reaching body temperature, the wire or tube will regain its initially formed coiled-shape, which will be imparted to the shaft. An inflatable balloon 213 optionally can be mounted to the shaft. Optionally, marker bands 215 can be placed around the coiled tip 210 after it is formed (FIG. 24). The distance between the bands 215 can be known and calibrated so that it can be used to gauge lengths and positions within the tubular vessel in which the catheter 200 is inserted.

Figure 25:
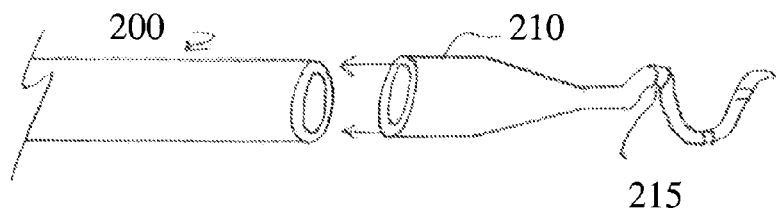
FIG. 25 is a perspective side view of an integrally formed marker attachment tip.
Figure 42:
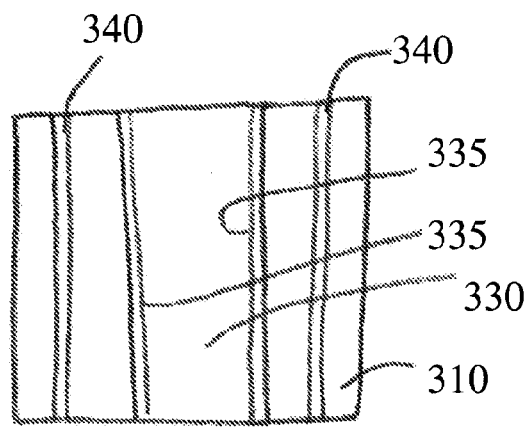
FIGS. 42 and 43 are top and end views, respectively, of one side of a heating element to contain and heat the compression die of FIGS. 40 and 41.
Figure 43:
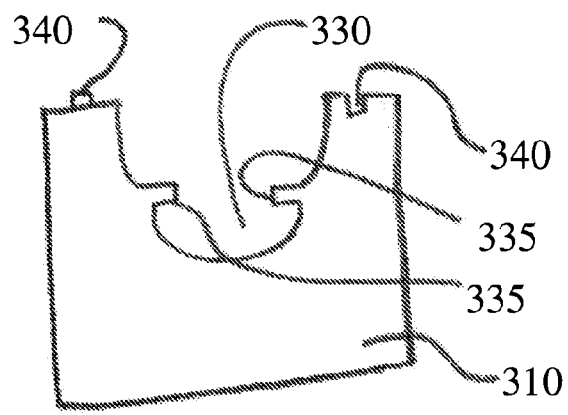
Figure 44:
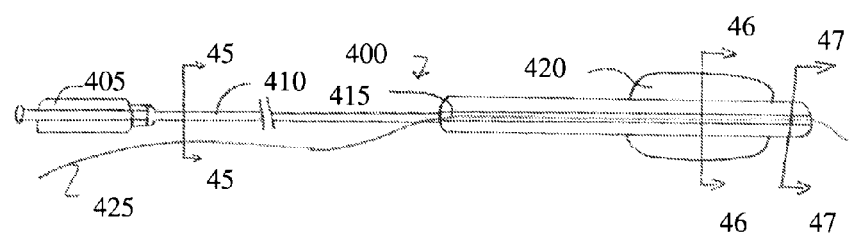
FIG. 44 is a side view of a catheter having a guide wire slot for rapid exchange of the guide wire.

As illustrated in FIGS. 25–27, the coiled tip 210 can be formed as a separate tip that is formed to be coiled using any of the methods described above, and then fused to the catheter using any of the well-known fusing techniques, such as hot die fusing, thermal fusing, laser fusing, and/or RF-induction fusing or heating. The tip can be formed with a dual lumen and the upper lumen 225 cut away so that an opening 230 of that lumen remains (FIG. 27). The lower lumen 235 then is formed as a coil and then fused to the catheter. In this manner, the catheter lumen remains open along its entire length, including through the tip.

Referring to FIGS. 28–39, various embodiments, configurations, and further details of the marker attachments described above are shown. For example, FIGS. 28–30 show a marker attachment 120 with coils 130 that are open such that a guide wire can easily be inserted into each coil. The coils 130 are separated from each other by known distances. This embodiment of the marker attachment has a common, minimized outer diameter and an inner diameter configured to smoothly and tightly track a guide wire.

Referring to FIGS. 31–33, a marker attachment 120 can be formed with a single extension 145 and a single coil 130. The coil can be flexibly closed so that a guide wire can be inserted through the inner diameter of the coil or the coil can be flexibly opened so that the guide wire can be inserted and removed through the slot formed in that manner.

Referring to FIGS. 34–36, the marker attachment 120 can be formed with a mounting tip or mounting band 250 that is integral with the extension 145 and used to mount the marker attachment to the catheter. The tip or band 250 can be flared down or of a constant outer diameter. The coils can be formed such that a guide wire can be inserted into an opening in the coils so that the marker attachment and catheter will track the guide wire. The tip or band 250 can be adhered to the catheter tip by an adhesive or by compression of the band. For example, the band can be formed with an opening or slot to that it can be compressed together to be retained in place on the catheter.

Referring to FIGS. 37–39, the marker attachments described above can be configured to have mounting ends 275 that enhance attachment to a catheter. For example, referring to FIG. 37, the mounting end 275 includes extensions 280 on the edges and projections 285 on the sides. When the mounting end is mounted with the catheter, for example, in the mounting lumen, the extensions and projections further secure the end within the mounting lumen. Referring to FIG. 38, the mounting end 275 includes openings 290 through which an adhesive can flow or polymer in the mounting lumen can be compressed to further secure the end within the mounting lumen. Finally, referring to FIG. 39, the mounting end 275 can have a roughened or dimpled surface 295 that enhances adhesion. The extensions 280, projections 285, openings 290, and surface 295 can be formed using any known technique, including stamping, cutting, machining, etching, electron discharge machining ("EDM"), laser cutting, etc.

Referring also to FIGS. 40–43, the mounting ends 275 of the marker attachments 120 can be mounted in the mounting lumen 110 (FIG. 7) by using a split die system 300. Of course, many other conventional systems are known and this is merely one exemplary method. The split die system 300 includes a heated half die 305 and a heating half die retaining element 310. The die and element can be formed as an integral unit. However, as illustrated in FIGS. 40–43, which shows one half of the system 300, the die and element also can be separated formed and mounted together. The half die 305 includes a tapered channel 315 that includes a first length 316 and a second tapered length 317. The die 305 receives the shaft 105 with the mounting attachment 120 inserted. The half die 305 also includes male and female mating sections 320 for mating with opposite mating sections of the other half die 305, and mating sections 325 for mating with opposite mating sections in the die element 310. These can be configured as channels that slide over rails. The half die can be made of, for example, a heatable material with a nonstick surface, such as Teflon™ (i.e., polytetrafluoroethylene ("PTFE")). The die element 310 includes a channel 330 configured to retain the half die 305 and rails 335 configured to keep the die in position. The element also includes male and female mating sections 340 for mating with the other half of the element during compression. The element can be heated using any conventional means. In use, the catheter with marker attachment inserted is placed in the first length 316 and the two die halves 305 are closed together to compress and heat the catheter. The catheter is then manually or automatically advanced such that the distal tip is advanced into the tapered length 317. This forces the plastic of the catheter to be compressed around the marker attachment's mounting end 275 (FIGS. 37–39), which secure the marker attachment to the catheter. The die halves then are separated and the catheter removed. An inflatable balloon can be attached to the catheter before or after this operation, if desired Referring to FIGS. 44–48, although the catheter 100 described above can be configured with a marker attachment to track a guide wire and be easily and rapidly exchanged, a catheter 400 also can be configured to track a guide wire, and be easily and rapidly exchanged without the use of a marker attachment or marker system at all. For example, the catheter 400 includes a hub 405, a shaft 410, a slotted, open channel 415, an inflatable balloon 420, and an inflation lumen 425 for inflating the balloon 420 A guide wire 425 can be inserted and passed through the slotted, open channel 415.

In general, the catheter 400 has a non-concentric balloon cross-sectional profile, with the slotted channel 415 (including and being formed to include a guide wire channel 417 and a guide wire slot 418) located on the outside of the main shaft 410, at the longitudinal balloon seam, or generally in the area where the balloon is in contact with the outer surface of catheter shaft 410, even when the balloon is inflated. The guide wire slot or groove 415 can have an internal, concave profile. The open groove or slot 415 is smaller than the diameter of the guide wire, allowing the wire to move freely within the channel, but without coming out of the slot or groove unless it is pulled out by the physician. The wall of the slot 415 can be somewhat flexible so that the guide wire can be easily inserted through and removed from the channel 415 to easy exchange of the catheter over the guide wire.

Moreover, in a modification of the catheter 400, a conventional marker band can be optionally placed around the slot 415 at its distal most end to provide a highly visible radiopaque indicator and give a sense assurance that the guide wire is less likely to come out of the slot unless the physician slidably removes the guide wire through the marker. Of course, the marker band is optional in this configuration and the catheter 400 will be extremely functional and usable for easy and rapid exchange of guide wires without the marker band. In another modification, the guide wire channel or slot (415, 417, and 418) may be positioned along a detented longitudinal area of the balloon 420.

The guide wire 425 also may be inserted into the proximal end of the guide wire slot 418, or, through the top opening of the slot or grove, and then snapped or positioned into place. In this manner, the concave geometry and size of the interior of the groove or slot prevents the guide wire from falling out.

The catheter 400 is formed using conventional techniques as are known in the art of catheter fabrication. For example, the shaft can be fabricated by pressure extrusion or tubing extrusion such that the tube has a cross-sectional profile of the inflation lumen 425 and the channel 415. The proximal end of the channel 415 then is removed such that only the distal end of the catheter has the channel 415. The inflation lumen 425 then is closed to have a taper (FIG. 47) and a balloon next is formed on the shaft, as illustrated in cross-section in FIG. 46.

Figure 45:
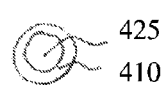
FIG. 45 is a cross-sectional side view of the shaft of the catheter of FIG. 44 taken at section mark A.
Figure 46:
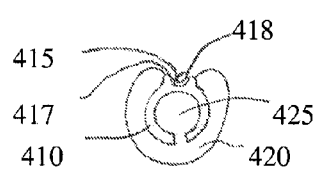
FIG. 46 is a cross-sectional side view of the shaft of the catheter of FIG. 44 taken at section mark B showing the guide wire slot.
Figure 47:
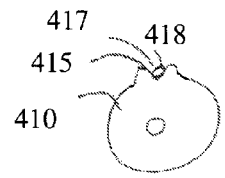
FIG. 47 is a cross-sectional side view of the shaft of the catheter of FIG. 44 taken at section mark C.
Figure 50:
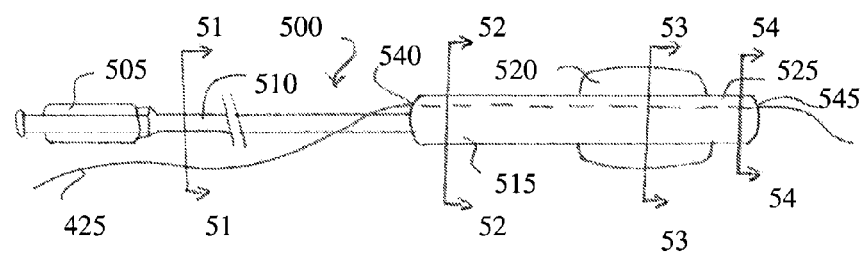
FIG. 50 is a side view of a rapid exchange catheter having a guide wire passage in the catheter shaft wall.
Figure 51:
FIGS. 51–54 are cross-sectional side views of the catheter shaft taken at points A, B, C, and D, respectively, of the catheter of FIG. 50.
Figure 52:
Figure 53:
Figure 54:
Figure 66:
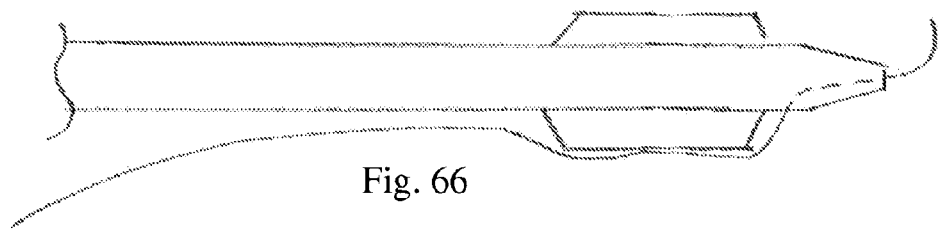
Figure 67:
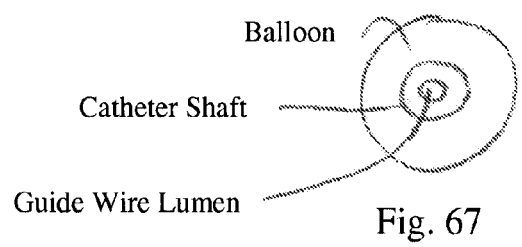
Figure 68:
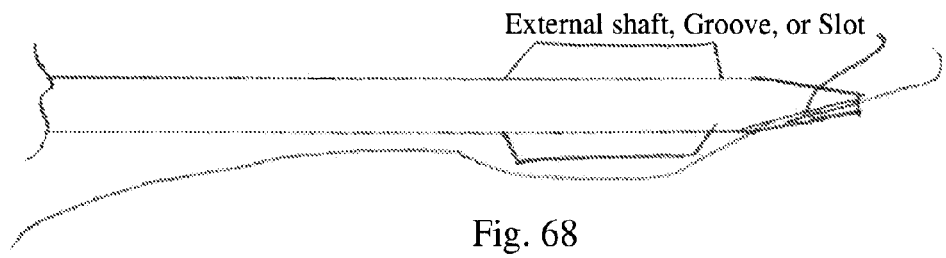
Figure 69:
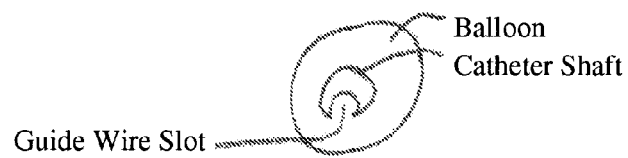

Of course, the catheter can be formed by extruding a single lumen tube having the cross-sectional profile of FIG. 45, extruding a tube having the lumen of FIG. 46 (without the balloon), and then fusing the two tubes together. Such fusing techniques are well known in the art and include hot die compression fusing, directed hot air, and RF-induction fusing.

As illustrated in FIGS. 48 and 49, the slot can be open, or can be open for most of the length and completely closed only for a short portion.

Referring to FIGS. 50–54, a catheter 500 includes a hub 505, a first shaft segment 510, a second shaft segment 515, a third shaft segment 520, and fourth shaft segment 525. The first shaft segment 510 includes an inflation lumen 530. The second shaft segment 515 includes the inflation lumen 530 and guide wire lumen 535. The third shaft segment 520 includes the inflation lumen, the guide wire lumen 535, and an inflatable balloon surrounding its outer circumference. Finally, the fourth shaft segment 525 includes the guide wire lumen 535 opening to the distal end of the catheter offset from the center of the catheter, or centered with the catheter, and the inflation lumen 530 is sealed closed by, for example, heating, compressing, and optionally pulling the tip or distal end in a tapered die and/or with the use of an adhesive to close the distal end of the inflation lumen. In this configuration, the guide wire passes through a first proximal opening 540 in the guide wire lumen and exits through a second distal opening 545 in the guide wire lumen. The length of the guide wire lumen can be less than, for example, 20, 15, or 10 cm. It can be, for example, less than 5 cm, and can even be approximately two cm in length. Moreover, the proximal opening 540 can be less than 20, 15, or 10 cm from the balloon, such as, for example, approximately 0.5 cm from the balloon, or between 0.5 cm and 10 cm from the balloon. The first segment 510 can be formed separately from the other segments (515, 520, 525) and then fused or otherwise attached to the second segment 515 using known methods from the catheter art Referring to FIGS. 55–59, another embodiment of a radiopaque marker catheter 550 that can be rapidly exchanged over a guide wire includes a hub 555, a first shaft segment 560, a second shaft segment 565, a third shaft segment 570, and a fourth shaft segment 575. The first shaft segment, the second shaft segment, and the third shaft segment include an inflation lumen 580. The third shaft segment 570 optionally includes a detent or longitudinal groove 583 in which the guide wire 425 can pass or be received during balloon inflation to prevent excessive force on the wire against the vessel wall. The formation of such longitudinal detents or grooves is disclosed and taught by Houser (U.S. Pat. No. 5,865,801), which is incorporated in its entirety herein by reference. The distal end of the catheter, the region below the balloon, and/or the proximally of the balloon, also could include a conventional marker band 585 that encircles the groove 583 and under which the guide wire could pass to advance the catheter along the guide wire. In this embodiment, a balloon 590 is non-concentrically placed around the catheter shaft segment 570 such that the groove is exposed. A tube 593 optionally can be mounted to the groove to provide a passage for the guide wire. The tube can be configured according to any of the concepts and techniques described above and can be configured as a radiopaque marker or gauge. This tube receives the guide wire during inflation to prevent it from being pressed against the vessel wall under the extreme pressures of balloon inflation.

Referring to FIGS. 60–63, a rapid exchange catheter 600 includes a hub 605, a first shaft segment 610, a second shaft segment 615, a third shaft segment 620, an inflatable balloon 625, and a guide wire lumen tube 630. An inflation lumen 635 passes through the first shaft segment, the second shaft segment, and the third shaft segment. The tube 630 starts proximally of, and ends distally of, the balloon 625. The distal end of the catheter after the balloon also can be formed with a groove through which the guide wire passes. The groove can be slotted, as described above to better retain, remove, and exchange the guide wire. This also provides a centering of the guide wire when it exits the catheter.

In other embodiments of the rapid exchange catheter, a guide wire lumen can be formed inside the catheter tubing wall rather than as a separate lumen. The guide wire lumen can be, for example, 0.5 cm long or less, and pass under a distal-most marker band. Where the catheter includes the guide wire being compressed between the balloon tubing and the vessel wall, longitudinal grooves, detents, valleys, cross-sectional voids, or other similar configurations in the balloon that would allow the wire to lay in a channel or groove-like region, and not be forced into the vessel wall under the pressures of balloon inflation. Additionally, the guide wire lumen-can be formed separately as a separate piece that then is bonded under the balloon, and may or may not optionally continue or extend to the tip of the catheter. Finally, the catheter may be formed from multi-lumen tubing with one or more lumens removed at specific areas along the catheter length.

The catheter shafts described above can be formed from any biocompatible medical grade polymer, such as nylon, polyethylene, Pebax®, polyimide, polyamide, polyester, polypropylene or any other combination of these or other suitable materials. The shaft can be reinforced to provide, for example, increased pushability, with a polymer or polymers, metals, metal alloys (such as nitinol, stainless steel, Elgiloy®, inconel, 17-7 PH™), or any combination of these or other suitable materials. Reinforcing shaft components can include a mandrel, a hypotube, or any other article that can be used inside the shaft, outside the shaft, or be used as the catheter shaft itself, or other configuration. The reinforcing shaft components can be movable, removable, or fixed. The reinforcement can be along the entire length, or a partial length at selected locations, and can be used to improve catheter trackability, pushability, and provide a strain relief transition between bonded catheter segments. Other shaft reinforcing components include wire or tube (shaped to be round, flat, or any other geometry); multiple tubing layer(s), with or without a tie or bonding layer; a mandrel; a hypotube; by irradiation; by using a variable wall thickness; and/or any combination of these or other suitable component(s). The balloon material can be compliant or non-compliant. Examples of compliant balloon materials include but are not limited to polyethylene; polyurethane; Tecoflex®; or any combination of these or other suitable materials Examples of non-compliant balloon materials include nylon; polyester (PET—polyethylene terephthalate, or other), Pebax®; polyimide; polyamide; or any combination of these or other suitable materials.

Radiopaque marker bands or marker attachments can be formed form gold, platinum/iridium, tantalum, or any combination of these or other suitable materials.

The proximal adapter, adapters, or hub can be configured as a Luer or other type fitting to enable connection to an inflation source and be fabricated from, for example, polycarbonate, polyurethane, polyester, or any combination of these or other suitable materials.

The catheter shaft can be fabricated by extrusion (e.g., single or multiple layer extrusion, tubing extrusion, pressure extrusion), casting, injection molding, dip coating, or any combination of these or other suitable methods or processes. The catheter shaft can be formed as multiple shaft pieces with tubing bonding, balloon to shaft bonding, and shaft to proximal adapter bonding. The bonding can include thermal (including RF-induction, forced heated air, laser, etc.), adhesive, ultrasonic welding, molding, or any combination of these or other suitable methods and processes.

To reinforce the shaft, the methods and materials usable include coils and coiling, braids and braiding, wraps and wrapping, or any combination of these or other suitable methods and materials. These reinforcements can be positioned or located inside, outside, within the shaft, in between, or any combination of these on the catheter.

The balloon fabrication process includes heat forming, cold forming, or any combination of these or other suitable methods and processes.

The catheter or the various parts of the catheter can be coated (static or active eluding) to be lubricious, anti-thrombogenic, therapeutic, or any combination of these or other suitable coating types, materials, and objectives. For example, the marker attachments and coils can be coated with a low durometer polymer to increase the softness of the attachment for less trauma during interaction with lesions.

Alternative applications for the rapid exchange feature include percutaneous transluminal angioplasty ("PTA"), stent and graft deployment catheters, therapeutic infusion, and any other catheter or medical device that utilizes a guide wire or guiding member.

The catheter size ranges for the catheters described above may include a catheter shaft having different proximal and distal diameters in the range of approximately 2 to 5 French, or greater. The balloon may have an inflated diameter that is between approximately 1.5 and 4.5 mm, or greater or less, and may be tapered. The length of the balloon may be approximately 10 to 40 mm, or greater or less. The guide wire may be approximately 0.014" diameter, although larger and smaller guide wire diameters are envisioned depending upon the application.

Additional views and embodiments of rapid exchange and marker catheters are illustrated in FIGS. 64–71. These provide rapid exchange of a guide wire and optional marker bands for sizing and gauging dimensions of a lesion. Moreover, referring to FIGS. 72 and 73, the marker attachment 120 can be formed from a long wire or tube 700 that is removably or permanently fixed in the mounting lumen of the catheter. If the wire or tube is formed from a rigid material, it will improve the pushability of the catheter in which it is installed. The wire or tube can be hollow and have a distal opening and a proximal opening, and can be used to tailor the stiffness and/or to inject a diagnostic and/or therapeutic agent or fluid, such as a radioactive agent, a gene therapy agent, or other biological or pharmacological agent. Moreover, a rigidity-imparting member, such as a mandrel, can be inserted in the hollow wire or tube to cause a change in stiffness of the wire or tube and, consequently the stiffness of the catheter. In addition, this configuration will reduce the manufacturing steps because it will be easier to mount the long wire or tube rather than the short mounting end 275 (FIGS. 37–39).

Referring to FIGS. 74–87, the catheters illustrated in FIGS. 44–63 also can be configured to provide perfusion of distal tissue during balloon inflation because these catheters include a slot or channel (415, 593) or lumen (535, 630) that provides an inlet for the blood flow proximal to the balloon and an outlet for the blood flow distal to the balloon. Moreover, these catheters can be used to deploy, position, and/or guide, in addition to a first guide wire, a second guide wire or other device, such as an embolic trap or embolic catching device 700 for deployment in the vessel distal to the balloon during angioplasty. In this manner, when the balloon is in place, the embolic trap 700 can be deployed through the channel or lumen, opened, and then the balloon can be inflated. Any embolic material created during the balloon inflation will be captured by the embolic trap 700 and will be removed from the vessel when the balloon catheter and embolic trap are removed. For example, referring specifically to FIGS. 74–76, a catheter 710 is configured similarly to the catheter 400 of FIGS. 44–47 and includes a slotted, open channel 715 (FIG. 75) or a pair of. slotted open channels 715 (FIG. 76). The slots provide a passage way from the proximal end to the distal end of the balloon. The channel(s) 715 provide a passage way for distal perfusion during balloon inflation, a first and/or second guide wire 425, a therapeutic or diagnostic device, such as an embolic trap 700. Optionally, one or more tubes can be positioned within the slot or slots 715 to more further define the passage way. Referring specifically to FIGS. 77 and 78, a catheter 730 is configured similarly to the catheter 500 of FIGS. 50–54 and includes a pair of passage ways 535 passing longitudinally through the wall of the catheter shaft. One passage way can be used to deploy or track a guide wire and the other to carry, deploy, or position a therapeutic or protective device, such as the embolic trap 700. The other passage way also can be used to deploy or track a second guide wire, or a therapeutic or diagnostic device. The channels or passage ways 715 can be, for example, grooves, slots, detents, distal coils, or combination of these or other suitable channel. The channels or passage way may be interrupted, full catheter length, placed distal only, or partially along the length of the catheter (e.g., the distal end of one of the channels or passage ways may end before the end of the catheter—under or near the balloon region). As described in greater detail below, a first guide wire may then be able to exit the channel or passage way from a location other than the distal end (e.g., tip) of the catheter—for example, through a void or opening through the balloon—while enabling a second guide wire to exit a second channel or passage way at the distal end of the catheter. The guide wire may be positioned into a side branching vessel, to direct another catheter (e.g., for PTCA, stent deployment, or other) into the side branch. Such a placement can be particularly beneficial when deploying a second stent (e.g., a bifurcated stent segment or other configuration of a stent) or other therapeutic or diagnostic device to or around the treatment site.

Figure 79A:
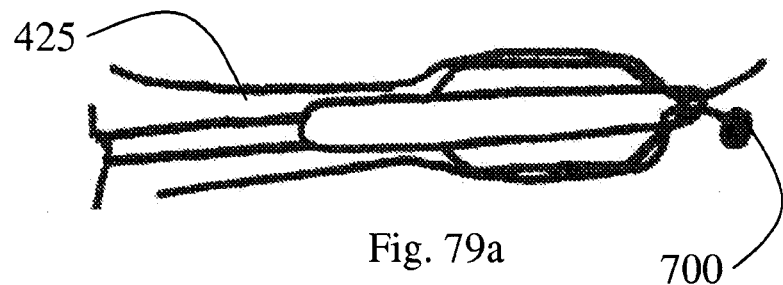
FIGS. 79a, 79b, and 79c are a side and two cross-sectional shaft views, respectively, of a catheter having one or more detents or grooves with an optional guide wire passage tube and a passage tube for a therapeutic or protective device
Figures 79B, 79C:
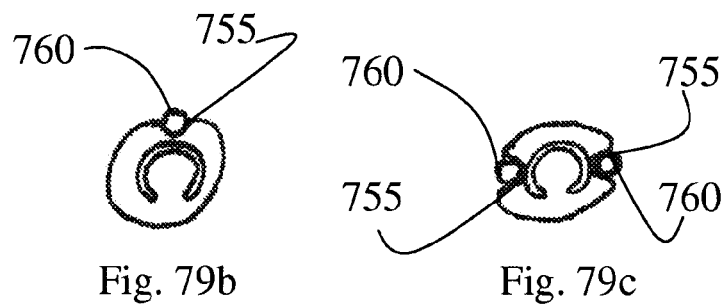

Referring specifically to FIGS. 79a, 79b, and 79c, a catheter 750 is configured similarly to the catheter 550 of FIGS. 55–59 and includes one or more detents or longitudinal grooves 755 in which one or more tubes 760 can be mounted to provide a passage for the guide wire 425, the embolic trap 700 or any other therapeutic, diagnostic, or protective device to be carried, deployed, or positioned For example, one tube 760 can be used to track the guide wire 425 and the other tube 760 can be used to carry, deploy, and position the embolic trap 700. The tubes 760 can be configured according to any of the concepts and techniques described above and can be configured as a radiopaque marker or gauge. These tubes receive the guide wire and a portion of the length of the embolic trap device 700 during inflation to prevent it from being pressed against the vessel wall under the extreme pressures of balloon inflation.

Figures 82A, 83A:
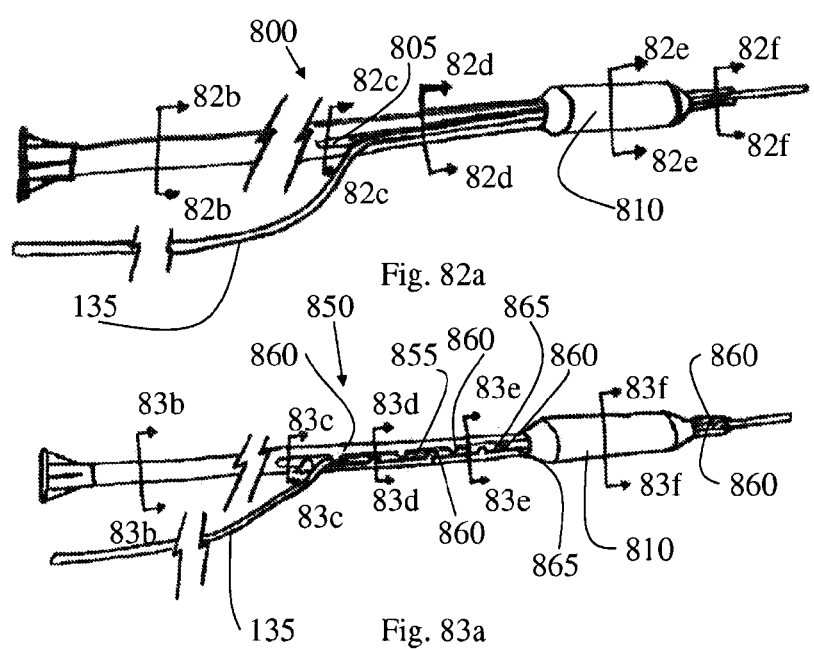
FIGS. 82a–82h are side and cross-sectional side views of a catheter having a slot along its length
FIGS. 83a–83g are side and cross-sectional side view of a catheter having a slot along its length and protrusions in the slot.
Figures 82B, 82C, 82D:
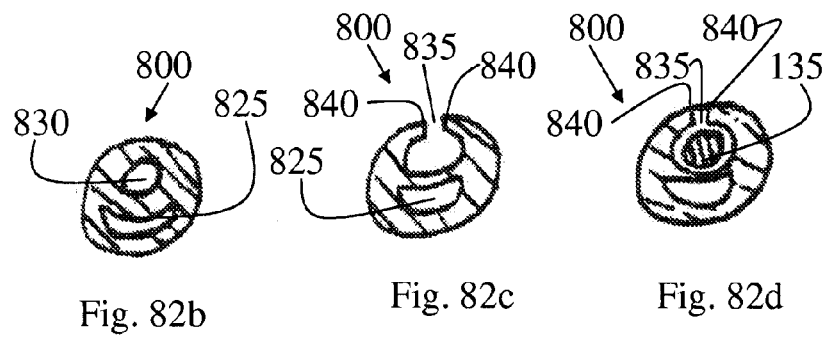
Figures 82E, 82F, 82G:
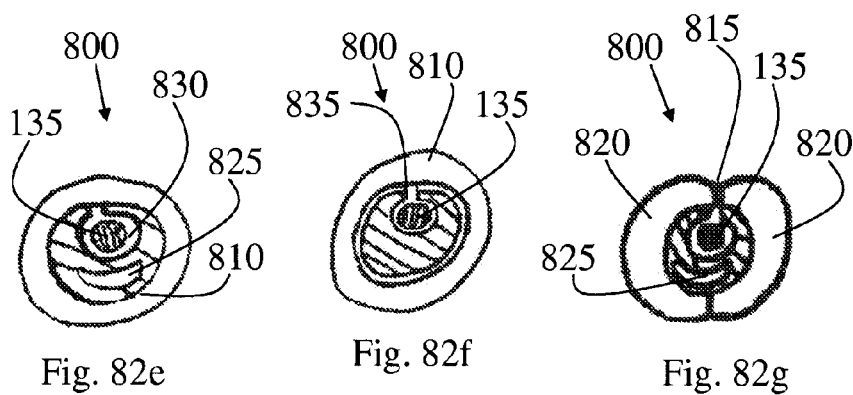
Figures 82H, 83B, 83C:
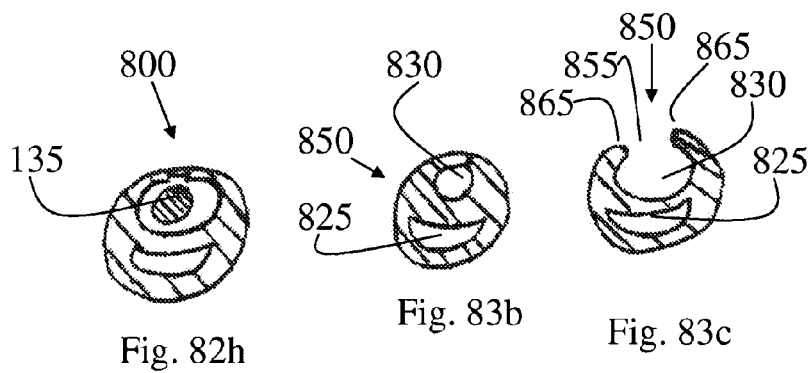

Referring specifically to FIGS. 80 and 81, a catheter 775 is configured similarly to the catheter 600 of FIGS. 60–63 and includes one or more lumen tubes 780. The tubes 780 start proximally of, and end distally of, the balloon. One of the lumen tubes 780 can be used to deploy or track a guide wire and the other to carry, deploy, or position a therapeutic or protective device, such as the embolic trap 700 The distal end of the catheter after the balloon also can be formed with one or more grooves through which the guide wire passes. The groove can be slotted, as described above to better retain, remove, and exchange the guide wire and/or the embolic trap. This also provides a centering of the guide wire and embolic trap where it exits the catheter. The techniques and devices for providing a method of deploying an embolic device or trap 700 can be applied to other types of catheters as well, such as diagnostic, therapeutic, guiding, and other types of catheters Referring to FIGS. 82a–82g, a rapid exchange catheter 800 includes a slot 805 along its length. The slot extends from any position proximal of an inflatable balloon 810 to a position distal of the inflatable balloon, and is configured to accept and removably retain a guide wire 135. The guide wire can pass under the balloon as illustrated in FIG. 82e or in an opening 815 between a pair of non-circumferential balloons 820, as illustrated in FIG. 82g. The catheter 800 can be extruded as a dual lumen shaft having an inflation lumen 825 and a guide wire channel 830 that is modified to be the slot 805 (FIG. 82b). The slot 805 is formed to have an opening 835 that has a width that is narrower than a width of the guide wire channel 830. For example, the slot 805 can be formed from a pair of longitudinal edges 840 which run the length of the slot. The slot can be formed by a cutting operation or other material removal operation. If the catheter 800 is formed from a flexible polymer, the longitudinal edges will be flexible enough to flex to intentionally receive and intentionally remove the guide wire 135 but the combination of the flexibility and the width of the slot will be such that the guide wire will not easily pass through the slot without the physician applying force to pull it through. The distal end of the slot may open to the side of the catheter or to the distal tip of the catheter. In either configuration, the catheter will track the guide wire and can be rapidly exchanged because the guide wire can be pulled through the slot until it exits the slot at a point just proximal of the balloon.

The slot can be formed to start adjacent to the hub, adjacent to the inflatable balloon, or at any position in between. For example, if the slot starts adjacent to the hub, the pushability and the trackability of the catheter 800 may be perceived to be better. Then, to remove the catheter from the guide wire, the guide wire can be pulled out of the slot until it is just proximal to the balloon. If the slot 805 starts in the vicinity of the balloon, that portion of the channel 830 between the hub and the slot can have a mandril inserted within to improve pushability and rigidity, as necessary or desirable. The mandril can be movable, removable, or fixed.

The catheter 800 can be modified to have slot 840 with a narrow width or wider width. For example, the distance between the longitudinal edges 840 can be less than 0.005 inches. If the catheter 800 is made from a flexible polymer, the edges will nonetheless be flexible enough such that the guide wire 135 still can be received or removed through the slot. The slot also can be wider so that the distance between the edges 840 is slightly less than the diameter of the guide wire, for example, 0.005 inches less than the diameter of the guide wire. In this manner the guide wire will still be retained within the slot but will be even more easily received and removed through the slot.

The channel 835 can be formed to have any cross-sectional profile to the extent that a guide wire can be at least partially retained within the channel. Moreover, the cross-sectional area of the channel only needs to be large enough to receive at least a part of the guide wire.

Figures 83D, 83E, 83F:
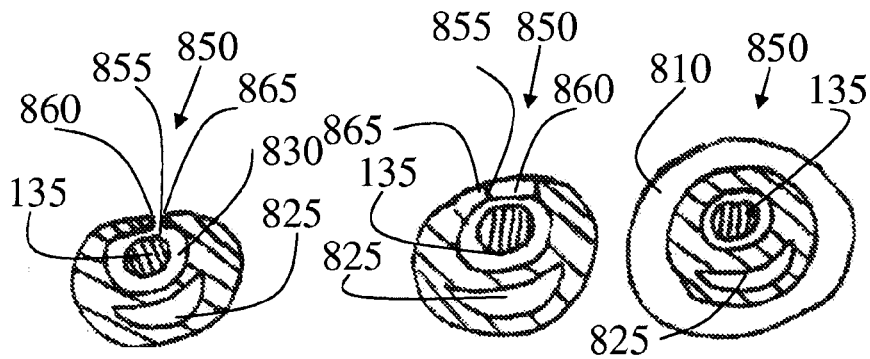
Figure 83G:
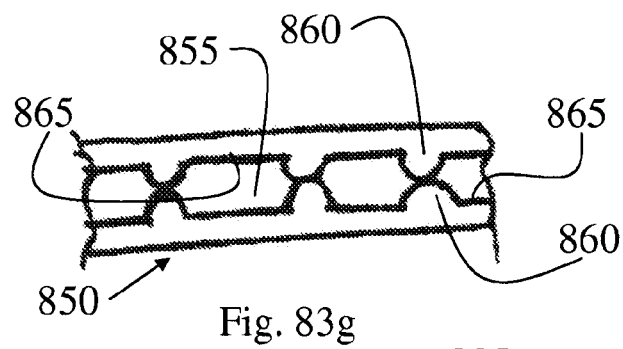

Referring to FIGS. 83a–83g, a rapid exchange catheter 850 includes a slot 855 along at least a portion of its length and protrusions 860 that extend from opposite longitudinal edges 865 of the slot. The protrusions 860 can be offset (FIG. 83a) or aligned (FIG. 83g) and can be continuous along the length of the slot or discontinued under the balloon 810 (FIG. 83F). The catheter is formed by, for example, extrusion and includes a pair of lumens 825 and 830. The lumen 830 is converted to a channel by forming a slot into the lumen. The slot 855 is formed by, for example, removing wall material of the catheter to form an opening into the lumen 830 The material can be removed in short or long segments, depending upon whether the protrusions 860 are to be offset or aligned. The protrusions then can be formed by cutting them in the center between the edges 865 (aligned protrusions) or adjacent to the edges (offset protrusions).

The protrusions 860 are flexible enough to allow the guide wire to be inserted and removed between them (aligned protrusions) or between the protrusion and the longitudinal edge 865 (offset protrusions). In this manner, the guide wire can be easily removed from the catheter in a rapid exchange procedure.

The slot 855 can be formed to start adjacent to the hub, adjacent to the inflatable balloon, or at any position in between. For example, if the slot starts adjacent to the hub, the pushability and the trackability of the catheter 850 may be perceived to be better. Then, to remove the catheter from the guide wire, the guide wire can be pulled out of the slot until it is just proximal to the balloon. If the slot 855 starts in the vicinity of the balloon, that portion of the channel 830 between the hub and the slot can have a mandril inserted within to improve pushability and rigidity, as necessary or desirable The catheter 850 can be modified to have slot 855 with a narrow width or wider width. For example, the distance between the longitudinal edges 865 and the protrusions 860 can be less than approximately 0.005 inches or more than approximately 0.005 inches. If the catheter 850 is made from a flexible polymer, the edges will nonetheless be flexible enough such that the guide wire 135 still can be received or removed through the slot. The slot also can be wider so that the distance between the edges 865 and protrusions 860 is slightly less than the diameter of the guide wire, for example, 0.005 inches less than the diameter of the guide wire. In this manner the guide wire will still be retained within the slot but will be even more easily received and removed through the slot.

The channel 835 can be formed to have any cross-sectional profile to the extent that a guide wire can be at least partially retained within the channel. Moreover, the cross-sectional area of the channel only needs to be large enough to receive at least a part of the guide wire.

Figures 84B, 84C, 84D:
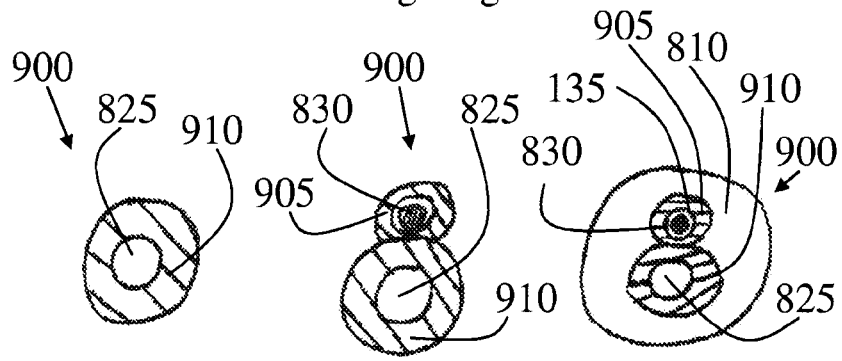
FIGS. 84a–84g are side and cross-sectional side views of a catheter having a guide tube integrally mounted or firmly attached to a catheter shaft.
Figure 84A:
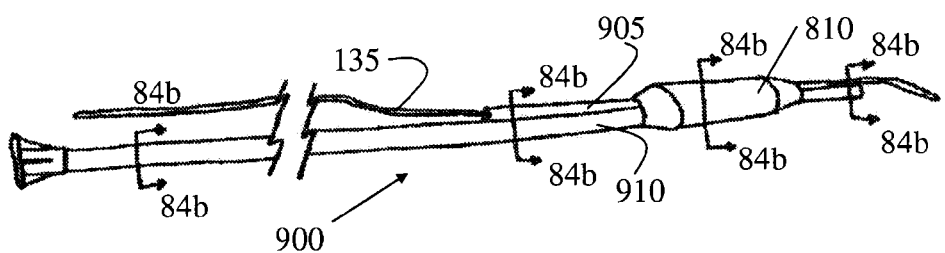
Figure 85A:
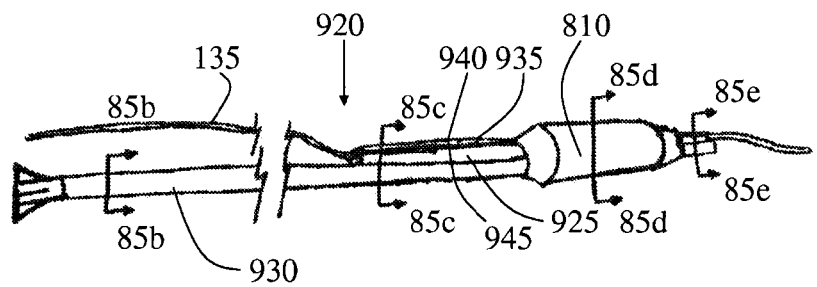
FIGS. 85a–85g are side and cross-sectional side views of a catheter having a slotted guide tube integrally mounted or firmly attached to a catheter shaft.
Figures 84E, 84F, 84G:
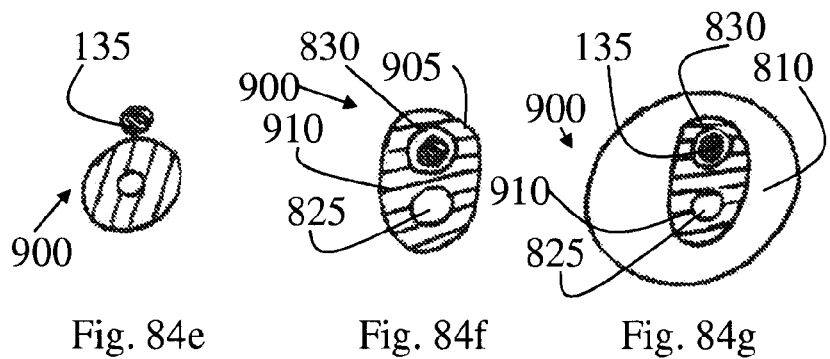

Referring to FIGS. 84*a*–84*g*, a rapid exchange catheter 900 includes a guide tube 905 integrally mounted or firmly attached to a catheter shaft 910 The catheter shaft 910 includes an inflation lumen 825 to inflate an inflatable balloon 810 The guide tube 905 includes a guide wire channel 830 through which a guide wire can pass and/or which can be used as perfusion channel. The guide tube 905 may be separately extruded and then mounted to the catheter shaft (FIGS. 84*c* and 84*d*). The guide tube 905 also may be integrally formed with the catheter shaft, for example by extrusion, and then the proximal most portion of the guide tube removed in a material removal operation, as is well known in the extrusion and plastic fabrication arts (FIGS. 84*f* and 84*g*). The guide tube 905 can pass under the balloon 810 and extend to the distal tip of the catheter, as illustrated in FIG. 84*a*. The guide tube also can end proximally of the balloon 810 and then the guide wire could pass underneath or on top of the balloon. The guide tube also can be mounted to the catheter such that only the proximal end and the distal end of the tube are mounted to the catheter, using an adhesive for example, and the middle section of the tube are not physically attached to the catheter. In this manner, if the proximal end and the distal end of the tube are outside of the ends of the balloon, the balloon can be mounted underneath the tube such that the balloon forms a fold up and around the tube. If the tube additionally includes a side port opening, a guide wire can be passed through that opening to access a side branch of a vessel. Moreover, a radially extending channel can be formed in the folds of the balloon, as described herein, and that channel used to guide the guide wire to the side branch. The guide tube also can extend part way or all the way underneath the balloon but then terminate such that the distal tip of the catheter 900 has a smaller diameter.

By having a short guide tube 905, the catheter 900 can be easily and rapidly removed and exchanged from the guide wire 135. Moreover, the guide tube 905 can be fabricated to have a slotted configuration, as described above with respect to FIGS. 82*a*–82*h* and FIGS. 83*a*–83*g*, or with any of the configuration described below (FIGS. 85*a*–85*g*, FIGS. 86*a*–86*f*, or FIGS. 87*a*–87*g*).

Referring to FIGS. 85*a*–85*g*, a rapid exchange catheter 920 includes a slotted guide tube 925 and a catheter shaft 930 upon which the guide tube is integrally mounted or firmly attached. The slotted guide tube 925 includes a slot 935 that opens into a channel 830 and is formed by an upper edge 940 and a lower edge 945. To insert the guide wire 135 into the channel 830, the guide wire is pressed lengthwise of end first between the two edges 940 and 945. The distance or clearance between the edges may be less than the diameter of the guide wire such that guide wire must be forced between the edges, whether the guide wire is being inserted or removed from the channel 830. Once the guide wire is within the channel 830, the edges must be separated to remove the guide wire.

The slotted guide tube 925 may extend distally from the balloon a short distance, all the way to the distal tip, or not at all. The tube 925 may extend proximally from the balloon 810 a short distance, all the way to a position adjacent to the hub, or a position in between. As such, because the guide wire can be removed from the channel 830 at any point along its length, the length of the guide tube can be any length and not adversely affect the ability of the physician to remove the guide wire. Thus, the length of the guide tube can be tailored to beneficially affect other characteristics of the catheter 920 as needed.

Figures 85B, 85C, 85D:
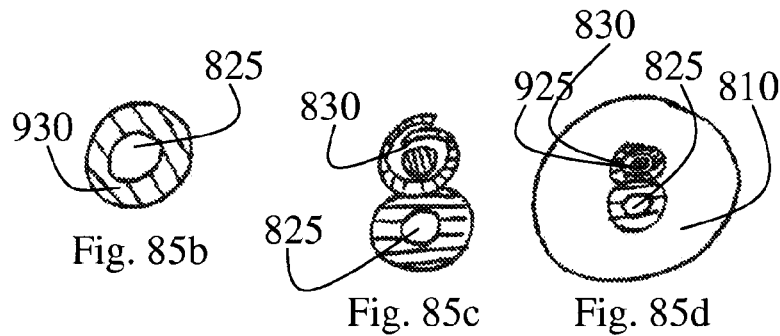
Figures 85E, 85F, 85G:
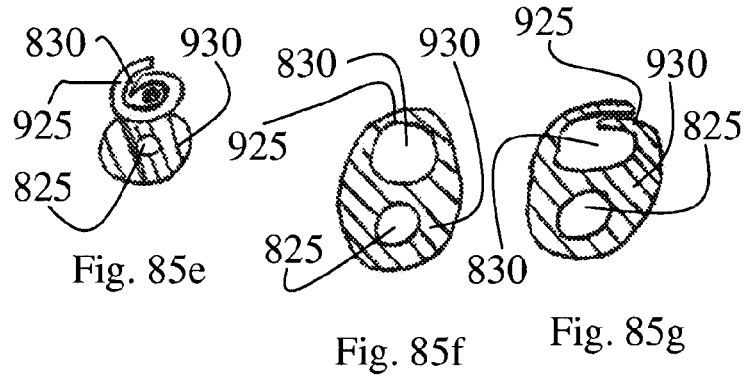
Figure 86A:
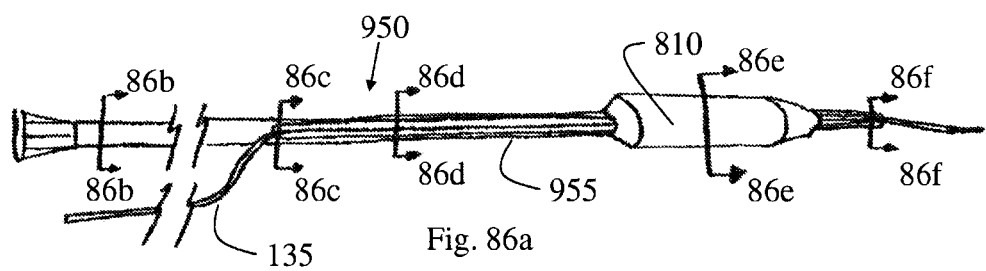
FIGS. 86a–86h are side and cross-section side views of a catheter having a longitudinal slot along its length

The slotted guide tube 925 may be formed as a separated extruded tube that then is firmly attached to a separated extruded catheter shaft 930 (FIGS. 85*c*–85*e*). The slotted guide tube 925 also may be formed by sequentially extruding a dual lumen catheter shaft 930, forming a slot in a slot forming operation, and removing a proximal and/or distal portion of the guide tube 925 in an optional material removing operation to set the length of the guide tube. In the slot forming operation, a longitudinal cut can be formed along at least a portion of the length of the guide tube. The lower edge 945 then is pressed down and inwardly below the upper edge 940. The upper edge 940 can simultaneously or later by pressed downwardly and over the lower edge. The edges then can be set in place relative to each other by, for example, applying heat.

Figures 86B, 86C, 86D:
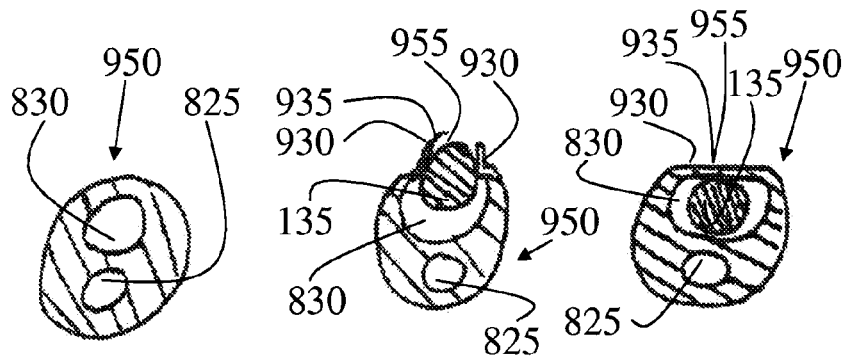
Figures 86E, 86F, 86G:
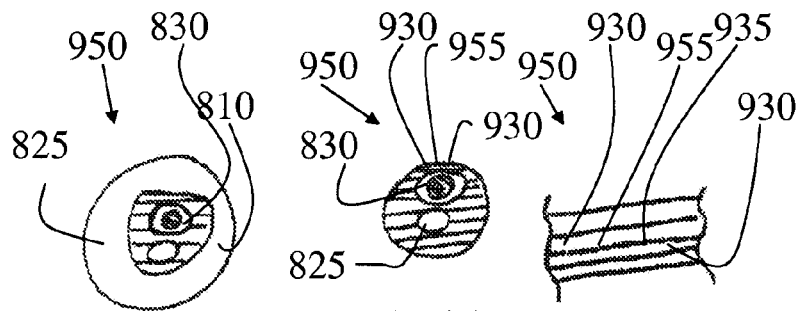
Figure 86H:
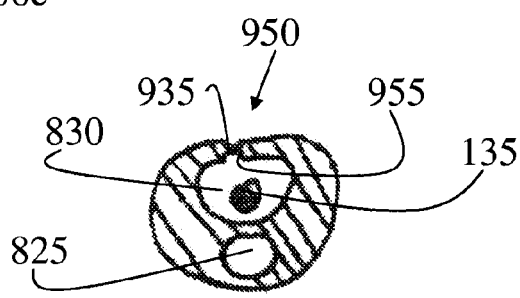

Referring to FIGS. 86*a*–86*h*, a rapid exchange catheter 950 includes a slot 955 along its length. The slot 955 includes one or two flexible edges 930 that meet along a longitudinal perforation or weakened section 935 (FIG. 86*c*, 86*d*, 86*f*). The flexible edges 930 can be joined and the section 935 can be perforated such that a guide wire can be pulled out of a guide wire channel 960 by rupturing the longitudinal perforations 935 (FIG. 86*g*). In another implementation, the flexible edges 930 can be joined and the section 935 can be scored such that the weakened section 935 can be longitudinally torn by pulling the guide wire out of the guide wire channel 830 (FIG. 86*g*). The perforation or weakened section 935 can be formed by merely scoring or perforating along the length, for example, by extruding such that the upper wall of the weakened section is extruded relatively thin. In another implementation, the perforation or weakened section can be formed by initially removing an outer wall thickness and then perforating or scoring the thinned wall. In either manner, the weakened section 935 will be more easily opened such that the guide wire can be removed from the channel 830.

The slot 955 may extend distally from the balloon a short distance, all the way to the distal tip, or not at all. The slot 955 may extend proximally from the balloon 810 a short distance, all the way to a position adjacent to the hub, or a position in between. As such, because the guide wire can be removed from the channel 830 at any point along its length, the length of the slot can be any length and not adversely affect the ability of the physician to remove the guide wire. Thus, the length of the slot 955 relative to the remainder of the channel 830 can be tailored to beneficially affect other characteristics of the catheter 950 as needed by, for example, placing a mandril in the remainder of the channel 830.

The slot 955 may be formed in a separately extruded tube, perforated or weakened, is and then firmly attached to the catheter. In another implementation, the catheter is extruded as a dual lumen catheter and then the perforation or weakening is performed.

Figure 87A:
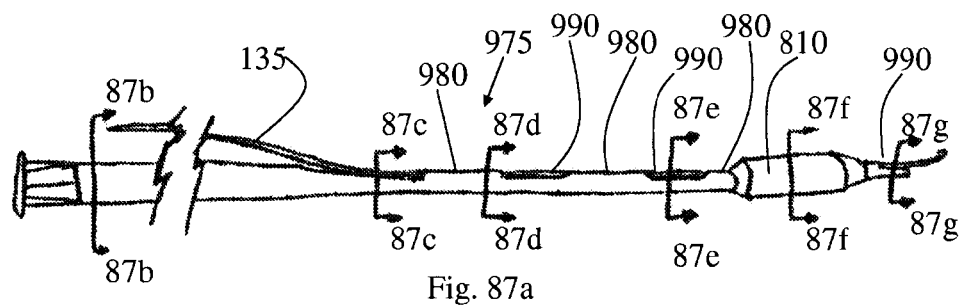

Referring to FIGS. 87*a*–87*j*, a rapid exchange catheter 975 includes one or more guide sections 980. The guide sections 980 include a longitudinal channel 830 sized to receive a guide wire. The guide sections can include a longitudinal slot as described in the various configurations above (FIGS. 87*h*, 87*i*, 87*j*). The guide sections can have tapered leading and trailing edges 990 that provide for atraumatic insertion and removal of the catheter 975. The guide sections 980 can be formed as a separately extruded tube that then is firmly attached to the catheter or extruded integrally with the catheter 975 as a dual lumen catheter shaft with a subsequent material removal operation.

Figure 88:
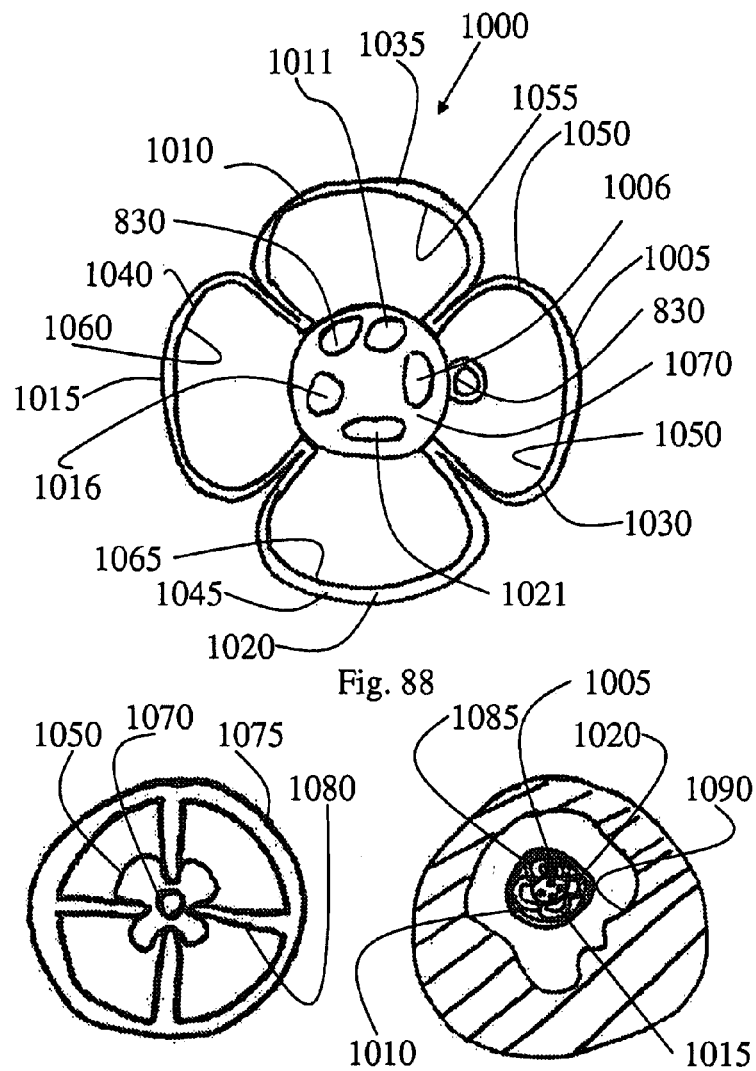
FIG. 88 is a cross-sectional side view of a multi-compartment balloon catheter.
Figures 89A, 90:
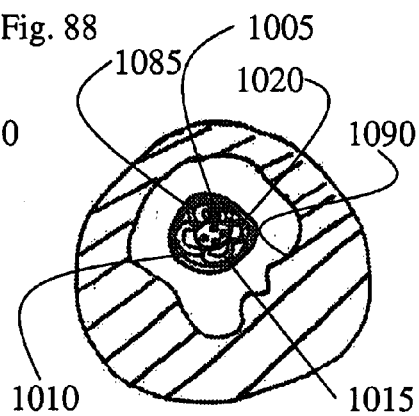
FIG. 89a is a cross-sectional side view indicating the formation of the multi-compartment balloon catheter of FIG. 88.
FIG. 90 is a cross-sectional side view of the multi-compartment balloon catheter of FIG. 88 inserted within an obstructed vessel.
Figure 89B:
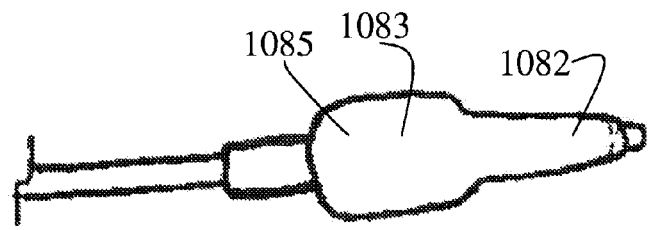
FIGS. 89b–89e are side views of a multi-diameter balloon for placing a stent in the coronary artery at a position distal to the coronary ostium.
Figure 89C:
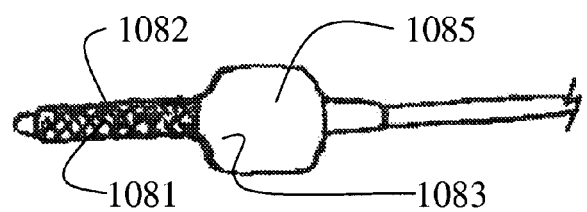
Figure 89D:
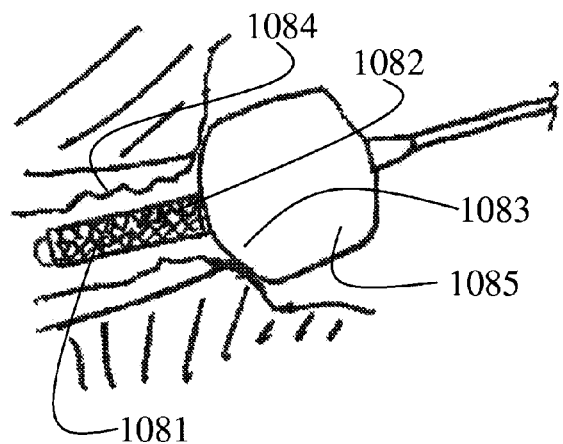
Figure 89E:
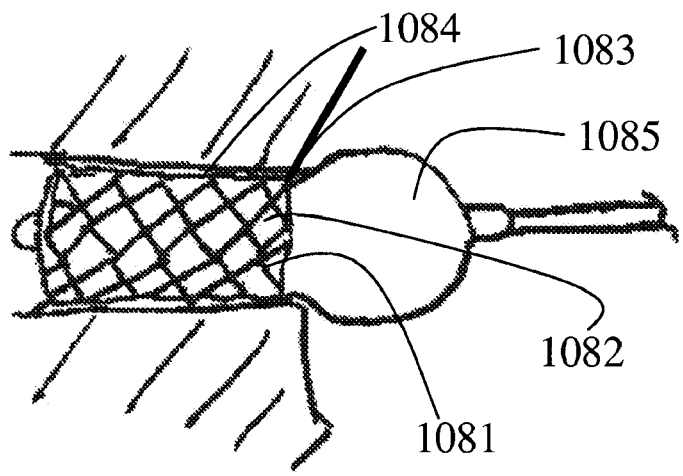
Figures 91A, 91B:
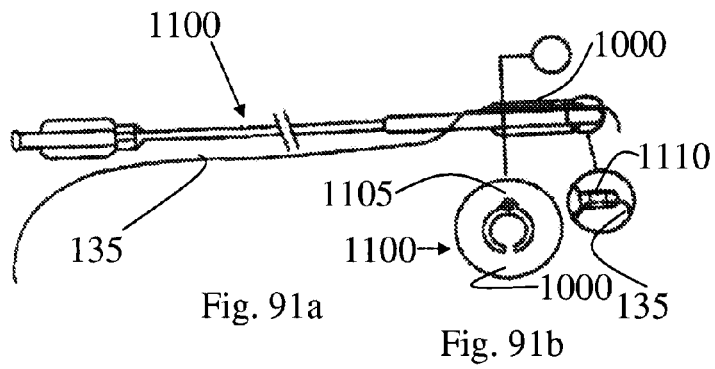
FIGS. 91a–91g are side and cross-sectional views of a balloon catheter having a slotted guide wire/perfusion channel, a marker band, and a balloon with one or more compartments.
Figures 91C, 91D, 91E:
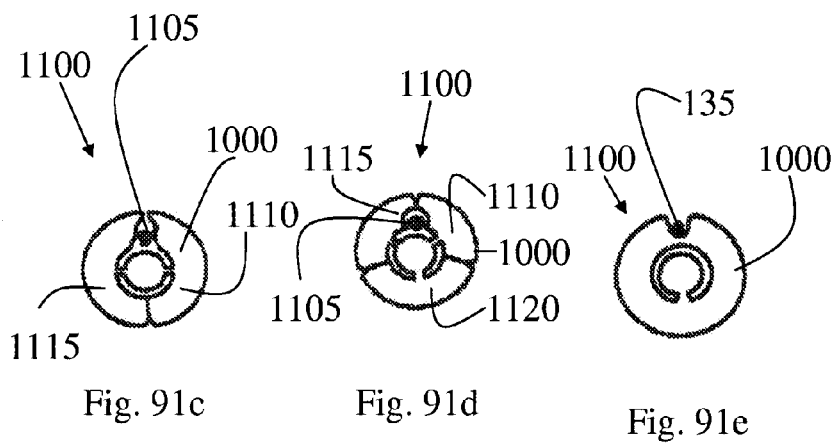
Figures 91F, 91G:
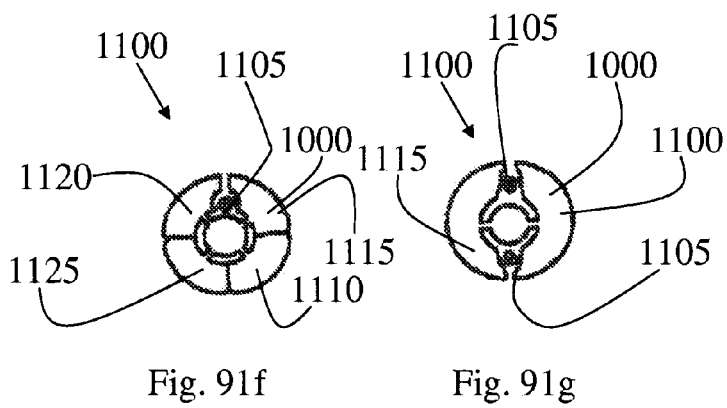
Figures 94A, 94B:
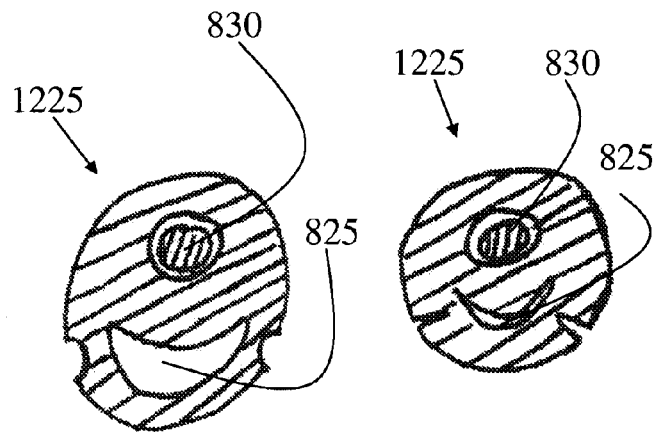
FIGS. 94a–94d are cross-sectional views of a catheter having a collapsible balloon inflation/deflation lumen.
Figures 94C, 94D:
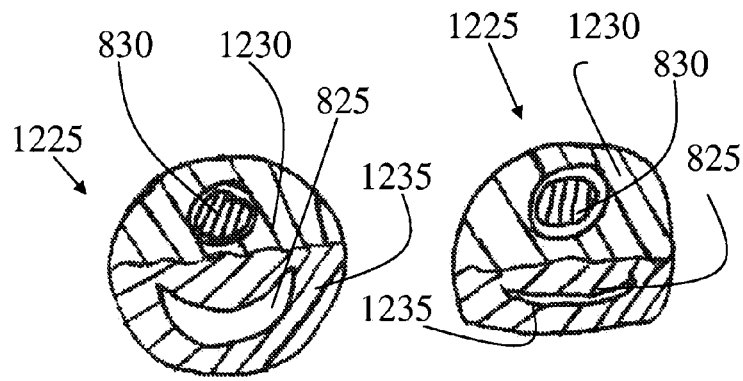

Although the catheters described above are illustrated to have only a single chamber balloon, a multiple chamber balloon (i.e., two balloon chambers, three balloon chamber, four balloon chambers, or more) also can be used. As illustrated in FIGS. 88 and 89*a*, a multi-chamber dilation balloon 1000 is formed to extend axially along a distal end region of a catheter. The balloon 1000 has several longitudinal compartments 1005, 1010, 1020, and 1025 all angularly adjacent to one another and cooperating to surround the catheter as seen in FIG. 88. The compartments 1005, 1010, 1020, and 1025 have radially outward wall segments 1030, 1035, 1040, and 1045, respectively, which cooperate to provide a continuous outer wall 1050 for the balloon 1000 and are adapted to engage a tissue wall segment of a vessel, such as an artery, over substantially the balloon's entire surface area. The balloon also has interior walls 1050, 1055, 1060, and 1065, respectively, which angularly divide the balloon 1000 into the plurality of the dilatation compartments 1005, 1010, 1020, and 1025 adjacent to one another and arranged angularly about the catheter tubing or shaft 1070. As seen in FIG. 88, each compartment extends approximately 90° angularly or circumferentially about the catheter tubing or shaft 1070. Each of the compartments is fluid tight and in fluid isolation from the other compartments. Thus, each compartment can be inflated to a different pressure to provide an eccentric cross-sectional profile. As one skilled in the art can appreciate, the balloon 1000 can be constructed to have any desired number of dilatation compartments and the balloon may have any range of accepted inflated diameters, such as an outer diameter of 3 mm when it is inflated about the catheter shaft. Each compartment 1005, 1010, 1020, and 1025 has a separate inflation lumen 1006, 1011, 1021, and 1026 for individually controlling the inflation of that lumen. The balloon material may be made of a compliant material such as polyethylene or polyurethane or other similar suitable material, etc. Alternatively, it may be an inextensible material such as nylon, PET and polyamide, or other similar suitable material, etc.

The interior balloon walls are formed by overlapping two layers of the balloon material. The four-compartment balloon 1000 is constructed by using a clip 1075 with four prongs 1080 that are used to draw or press portions of an inflated balloon against the outside surface of catheter 1070 as shown in FIG. 89*a*. The configuration then is set using methods known in the art, such as applying heat. Another method of construction is to create one balloon with interior walls of single thickness. For example, the balloon can be blown inside of a glass mold with the desired configuration. Moreover, the balloon 1000 can have any of the guide wire/perfusion configurations describe above. For example, the catheter can have a slotted channel that passes through the shaft and or a slotted channel that passes over the shaft.

The balloon may have a tapered geometry and/or two different diameters. One advantage of a tapered and/or multiple diameter balloon is that a larger section can function as a guide, reference, or stop when deploying a stent in the ostium to treat ostial lesions. Because of its size, it is unlikely that the larger diameter can be inserted into the coronary artery to allow accurate stent placement. A major complication that can occur when stenting the ostium is that of a section of the stent being deployed partially outside of the ostium and partially in the aorta In this manner, the balloon can be partially inflated such that the larger diameter proximal section of the balloon is inflated and when pressed up against the coronary artery, the inflated balloon prevents that portion of the balloon from entering the coronary artery. Referring to FIGS. 89*b*–89*e*, if a stent 1081 is placed on a smaller diameter distal portion 1082 of a balloon 1083, only that portion of the balloon, along with the stent, will be inserted into a coronary artery 1084. A larger diameter portion 1085 of the balloon 1083 will not enter the coronary artery 1084 when the larger diameter portion is at least partially inflated. Then, by inflating the balloon 1083 completely, the smaller diameter distal portion 1082 of the balloon will be inflated sufficiently to deploy the stent 1081 in the coronary artery without any of the stent extending into the aorta. In an alternative method, the balloon can have a constant diameter and the stent again placed on the distal portion of the balloon. Then, by partially inflating the balloon to a pressure sufficient to expand the portion of the balloon around which the stent has not been placed or crimped but not enough to deploy the stent, a larger diameter portion of the balloon will be created. When the catheter is advanced into the coronary artery, the expanded portion of the balloon will be unable to enter the coronary artery if the balloon has been sized properly. Thus, the stent will be entirely within the coronary artery and not extend into the aorta. The balloon can then be completely inflated and the stent deployed. Although described above with respect to one particular anatomical position, this technique can be implemented in other anatomical locations within the body.

The balloon 1000 and rapid exchange catheters described above can be used in balloon angioplasty, stent deployment and other procedures. For example, the inflatable balloon catheter 1000 having four dilatation compartments 1005, 1010, 1020, and 1025 can be inserted in a vessel until it reaches the obstructed area. Radiopaque markers can be placed on the catheter shaft under the balloon 1000 to assist the physician in positioning the balloon adjacent an obstruction. The multiple compartments of the balloon are then inflated to contact the obstruction.

The balloon catheter also may additionally be used in stent deployment. A plastically expandable stent 1085 that substantially surrounds the balloon 1000 of a catheter, in any of the embodiments describe above, may have the four dilatation compartments 1005, 1010, 1020, and 1025. Once the balloon 1000 and the stent are located at the appropriate location within the vessel and adjacent an obstruction 1090, the balloon compartments are inflated to deform the stent into contact with the obstruction. The physician is able to control stent deployment by adjusting the inflation of the balloon dilatation compartments as necessary. Greater inflation may be required for dilatation compartments 1015 and 1020 than compartments 1005 and 1010. Thus, compartments 1015 and 1020 can be monitored so that over inflation (that could cause vessel damage) in the obstructed area 1090 would be avoided. Furthermore, by viewing the pressure between the artery wall and balloon with regard to the balloon inflation pressure, the physician can determine that the stent 1085 is fully deployed.

For multi-balloon versions of the catheter, the individual balloons may be tailored or designed for specific purposes For example, the balloon intended to open an occlusion, may be different than the balloon that is intended to deploy a stent or a balloon with therapeutic infusion features. Examples of different version are found in Houser (U.S. Pat. No. 5,865, 801), which is incorporated herein in its entirety by reference.

FIGS. 91a–91g and FIGS. 92a–92f are examples of implementations of the multi-compartment balloon 1000 mounted on the catheters describe above. For example, FIGS. 91a–91g illustrate a balloon catheter 1100 having one or more slotted guide wire/perfusion channels 1105, a marker band 1110, and a balloon with one or more compartments 1115, 1120, 1125, and 1130.

FIGS. 92a–92f are side and cross-sectional views of a second balloon catheter 1150 having the multi-compartment balloon 1000 mounted on a catheter as described above and includes one or more slotted guide wire/perfusion channels 1105, a marker band 1110, and a balloon with one or more compartments 1115, 1120,1125, and 1130, and a central lumen 1135.

Referring to FIGS. 93a–93f, a catheter 1200 can be fabricated with a peelable guide wire opening 1205. In this configuration, the catheter shaft is extruded with an inflation lumen 825, a guide wire lumen 830, and a peelable lumen 1210 that is accessed by pulling a wire 1215 along a portion of the length of the catheter As best seen in FIG. 93e, the catheter shaft is extruded with the peelable lumen containing a wire or mandril 1220. A thin catheter wall is between the wire 1220 and the outer diameter of the catheter. A thin wall also is between the wire 1220 and the guide wire lumen 830. To remove the guide wire 135, the physician nicks the catheter shaft with, for example, a scalpel or pair of scissors, to expose the wire 1220 and bends the shaft to more easily access the wire. The wire 1220 then can be pulled longitudinally along the length of the catheter shaft or along a portion of the length of the catheter shaft to create the opening 1205 to the lumen 1210 (FIG. 93b). The physician can use, for example, a pair of tweezers or hemostats to pull a loop of wire from the lumen 1210 to initiate the opening. Once the opening 1210 is made, the physician can slightly bend the catheter to manipulate the guide wire 135 through the wall between the guide wire lumen 830 and the lumen 1210, and out the opening 1205 (FIG. 93c)

The peelable configuration has been described with reference to a catheter. However, this configuration also can be applied to a method and design of other medical products, such as a vascular introducer, sheath, or deployment device for deploying a medical device. The wire can be configured as a string, wire, multi-filament wire, polymer cord, polymer strand, multiple polymer strands, or any similar element.

Referring to FIGS. 94a–94d, the catheters described above can be made to have a reduced diameter cross-sectional profile by incorporating those features on a catheter 1225 having a collapsible balloon inflation/deflation lumen 825. For example, the collapsible inflation/deflation lumen 825 can extend the full length of the catheter or be confined to the distal section only. The collapsible lumen is configured to collapse onto itself when a negative pressure or vacuum is applied. During insertion, this is beneficial to further reduce the crossing profile. This characteristic may be accomplished by making the lumen walls thinner at the desired area(s), or other method, while still being able to contain the internal pressure when the balloon is inflated. This also may be accomplished by making the catheter shaft from two materials in a co-extrusion. A first material 1230 surrounds the guide wire lumen and a second material 1235 surrounds the collapsible lumen. The first material is more rigid than the second material and therefore is less likely to collapse upon itself when vacuum is applied. The second material is more flexible and collapses at a lower pressure than does the second material. The configurations of FIGS. 94a and 94b also can be fabricated with the materials 1230 and 1235.

FIGS. 95a–95s and 96a–96s are examples of more specific implementations of the techniques and features described above and include more specific detail to enable one of skill in the art in implementing the techniques and features described above. These implementations are merely representative examples of two implementations and, as such, the specific values provided below are expected to differ significantly and/or insignificantly in other implementations.

Figure 95F:
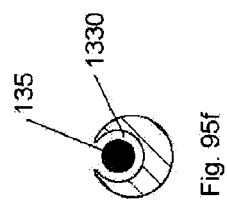
FIGS. 95a–95s and 96a–96s are examples of specific implementations of the techniques and features described herein and include specific details to enable one of skill in the art to implement the techniques and features described herein
Figure 95E:
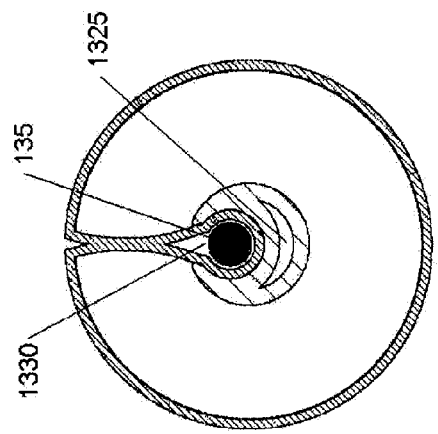
Figure 95D:
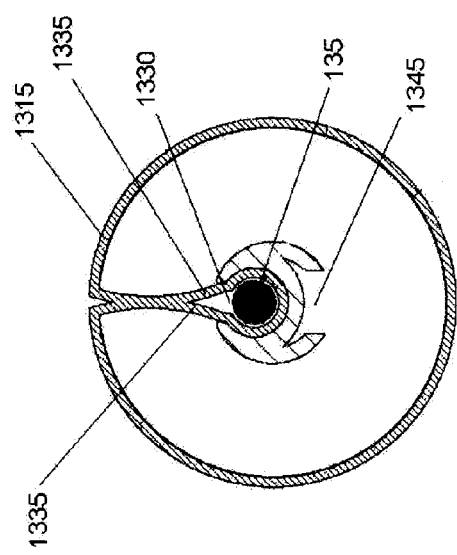
Figure 95M:
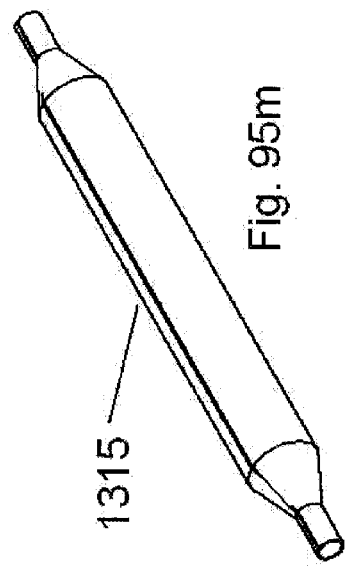
Figure 95N:
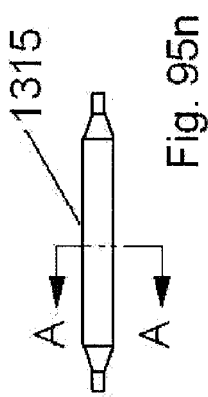
Figure 95L:
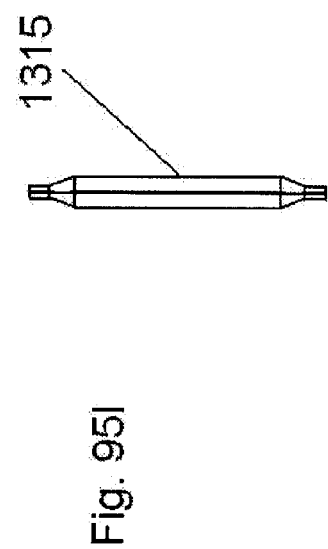
Figure 95O:
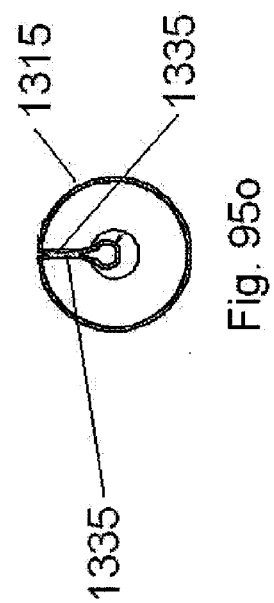

In particular, referring to FIGS. 95a–95s, a catheter 1300 includes a hub 1305, a shaft 1310, an inflatable balloon 1315, and a distal tip 1320. A guide wire extends from the distal tip. As illustrated in FIG. 95b, at section D—D the shaft 1310 has an inner diameter of 0.020 inches and an outer diameter of 0.036 inches and a single lumen 1325. As illustrated at FIG. 95c, at section E—E, the shaft 1310 has an outer diameter of 0.039 inches and includes the lumen 1325, which is used to inflate the balloon 1315, and a channel 1330 that is used to carry or contain a guide wire. FIG. 95d is a cross-sectional view of the guide wire, shaft and balloon at section F—F and illustrates the balloon 1315 having two edges 1335 in contact above an opening 1340 into the channel 1330. A 0.014 inch guide wire 135 is shown being in the channel. The opening 1340 of FIGS. 95c and 95d is wide enough to receive and remove the guide wire 135. The opening also is wide enough to include the walls of the balloon, which is bonded to the catheter inside the channel 1330. An inflation opening 1345 is shown passing between the inflation lumen 1325 and the interior of the balloon 1315. The only openings into the interior of the balloon are the inflation opening(s). The inflation opening is shown as being 0.020 inches wide at section F—F and the catheter shaft passing through the balloon is shown as having a 0.039 inch diameter. FIG. 95e is a cross-section view of the guide wire, shaft and balloon at section G—G and illustrates the guide wire passing through the guide wire channel 1330. FIG. 95f is a cross-sectional view of the guide wire and shaft at the distal tip 1320. Again, the guide wire is within a channel 1330 having an opening 1340 that is configured to receive a guide wire and allow the guide wire to be easily removed from the channel.

The catheter 1300 of FIGS. 95a–95s is fabricated with the balloon 1315 being bonded within the channel 1330 and the ends of the balloon being bonded to the shaft, as best illustrated in FIGS. 95i and 95k The balloon is placed around the shaft (i.e., insert the shaft into the channel through the balloon) and the balloon ends and a longitudinal length of the balloon are bonded to the portions of the shaft and within the guide wire channel, respectively. The edges of the balloon formed at the channel then will meet when the balloon is inflated.

FIG. 95g illustrates the length of the catheter 1300 being approximately 140 cm from the hub to the distal tip of the catheter 1300. FIG. 95i illustrates a close-up view of the balloon and shows how the guide wire is underneath the two joined edges 1335 of the balloon. FIG. 95i also illustrates the tapered end of the distal end of the balloon, which has a taper length of approximately 0.097 inches (2.5 mm). FIG. 95h illustrates that the proximal shaft may have a diameter of approximately 0.036 inches and the distal shaft (although proximal to the balloon) may have a diameter of approximately 0.038–0.039 inches with a transition area 1350 between the distal and proximal shaft. The distal shaft may be approximately 20 cm, and the entry of the guide wire into the guide wire channel may be approximately 15 cm from the distal tip of the catheter.

FIGS. 95*j* and 95*k* illustrate the balloon 1315 and an optional marker band 1355 placed under the balloon around the shaft. The marker band can be used to restrain the guide wire or direct its passage. FIGS. 95*l*, 95*m*, 95*n*, and 95*o* provide additional details about the balloon that are specific to this particular implementation. In this implementation, the balloon has an outer diameter of approximately 0.118 inches (3 mm), a wall thickness of 0.003 inches, a taper width of 0.006 inches between the balloon edges 1335, and a length of approximately 20 cm.

FIGS. 95*p–s* illustrate additional details about the shaft. For example, the inflation lumen is shown as having a width of approximately 0.028 inches, a center height of approximately 0.006 inches, a wall thickness around the inflation lumen of approximately 0.005 inches, an opening 1340 into the guide wire channel of approximately 0.012 inches, edges of approximately 0.005 inches in thickness, and a guide wire channel diameter of approximately 0.020 inches.

Figure 96G:
Figure 96H:
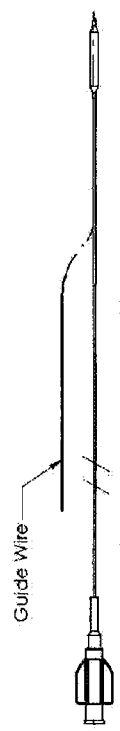
Figure 96I:
Figure 96J:
Figure 96K:
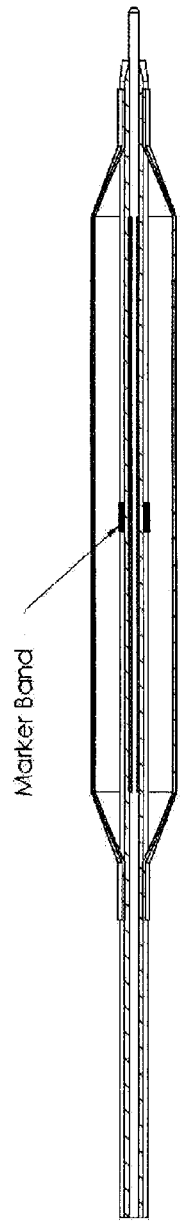
Figure 96M:
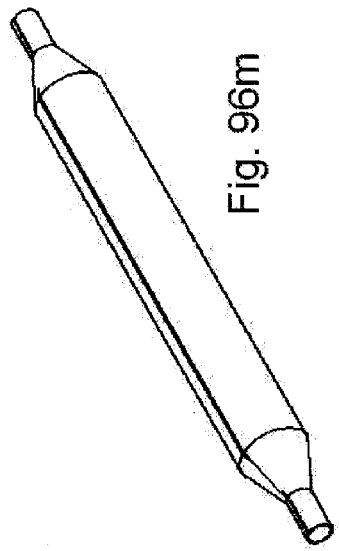
Figure 96N:
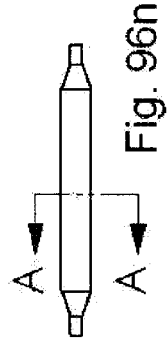
Figure 96L:
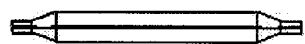
Figure 96O:
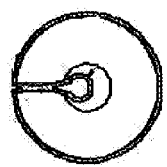

FIGS. 96*a–96s* illustrate a catheter 1400 that is similar in many respect to the catheter 1300 describe above. However, the catheter 1400 includes a narrower opening 1405 into a guide wire channel 1410 For example, the narrower opening 1405 may be approximately 0.006 inches (instead of the approximately 0.012 inches of the catheter 1300) because the catheter has the balloon bonded around the outer circumference of the shaft rather than in the guide wire channel, as is the manner with catheter 1300. The balloon is wrapped around the catheter shaft until the balloon edges are adjacent and then the balloon is bonded to the shaft. As such, the two edges of the balloon will contact each other upon inflation.

In general, the catheters described above have a proximal adapter that can be configured as, for example, a single Luer fitting for a single chamber or compartment balloon inflation, or multiple fittings for multiple balloon chamber, compartment, or segment inflation. The multiple balloon chamber or segment inflation can be individual and/or simultaneous. The multiple balloon chambers or segments may or may not be in fluid communication with each other.

The proximal shaft can be bonded together with the distal shaft using a Teflon coated mandrel that is inserted into the inflation lumen and heated to join both tubing sections together. FEP or PTFE tubing can be placed on the outside of the tubing to maintain the OD size during the joining process and then removed. The proximal shaft also can include a moveable/replaceable reinforcing or shaping member, as described above. The member may or may not continue through the distal section of the catheter and may be inserted into a dedicated lumen, or may use the inflation/deflation lumen during insertion. The distal shaft also may include the same or a different moveable/ replaceable reinforcing member as described above. The member may be inserted into a dedicated lumen, or the inflation/deflation lumen during insertion and removed for the inflation.

The guide wire can be contained as described above along the entire catheter length; in the distal section only; in the proximal section only; through, over, or parallel to the balloon; in the distal tip only; on top of the tip, inside the tip; inside the tip in between or under a marker band; and/or with an eyelet or coil configuration. The containment of the guide wire can also serve as a perfusion lumen and can be a channel having incomplete circumferential coverage with interior geometry matching the radius of the guide wire; a channel with one or more guide wire "hold downs" (i.e., partial coverage in a manner that is similar to catheter packaging trays); a limited length lumen or channel that is under and through the balloon but on top of catheter shaft; constrained in between balloon segments or detent(s), on top of the balloon, or on top of the catheter shaft; and/or on top of, or through the distal tip (i.e., at a position forward of the balloon)

The balloon can be a single chamber balloon with non circumferential geometry (i.e., incomplete circle, cross section void) in which the non circumferential geometry section is partial of the balloon height (i.e., above the shaft) or in contact and bonded together with the top of the shaft. When a grooved balloon is used with incomplete circumferential cross section geometry, the seam where the ends of the balloon come together may be longitudinal, or other, such as spiral, and can have interlocking end geometries ("S" or other profile).

The balloon also can be a multi-chamber or compartment balloon as described in Houser, U.S. Pat. No. 5,865,801, which is incorporated herein by reference in its entirety. When multiple grooved balloons are used (i.e., with an incomplete circumferential cross section geometry), the seam where the ends of the balloon come together may be longitudinal, or other, and can have interlocking end geometries ("S" or other profile).

The balloon inflation can be accomplished in a number of ways. For example, the non-circumferential geometry balloon may have circumferential interior vessel contact when inflated. Inflation of the balloon in a confined space will cause the radial ends of the balloon to come together, in particular when the balloon is made, partially or completely, from a compliant material, such as the materials described in Houser, U.S. Pat. No. 5,865,801.

The balloon is bonded to the catheter shaft by using a variety of methods, as described above, and includes the use of adhesives, solvents, heat, a combination of these, or other any other suitable method as known to those in the art.

The bonding of the balloon to the catheter shaft may further be configured in the traditional method, namely, the balloon shoulders being bonded to the catheter shaft The balloon also may be bonded to the top with the balloon wall bonded inside the guide wire channel (maintaining channel geometry). The outside of the top of balloon may be bonded to the bottom of the shaft, with the balloon shoulders being modified (i.e., sections removed so that there are not two layers of balloon material where the shoulders are bonded to the shaft) The balloon also may have a hole that is positioned and secured to align with the inflation/deflation port on the catheter shaft. The longitudinal edges of the balloon may be designed to expand and come in contact closest to the shaft initially, but with increasing internal balloon pressure, the contact of the balloon edges continues in an outward direction from the shaft to the outer surface of the balloon The balloon may be a single or dual longitudinally spaced balloons that are inflatable independently, or simultaneously. The balloon geometry may be different between balloons and non concentric, non circumferential balloon geometries may be used. The balloon may have openings to bond onto the shaft at the proximal and distal ends. The balloon also may also have a longitudinal edge, seam, opening, or cross-sectional void, to allow longitudinal bonding of the balloon directly to the catheter shaft, and also to create a void for the guide wire channel. The balloon strength may be increased by exposing the balloon material to radiation which causes cross-linking of the polymer chain.

The balloon also can be processed to impart a smaller cross section "memory" profile, after the balloon (and or balloon chambers or segments) has been inflated, deflated, and is ready to be withdrawn from the body (causing the balloon "wings" to be closer to the catheter shaft after deflation making it less likely to dislodge emboli or cause other deleterious effects during withdrawal of the catheter from the body). The process may include irradiation to cross-link, or heating to anneal, the balloon material while in a constrained configuration. Certain balloon materials and or compound additives, such as, for example, ProRad, may be used to impart this characteristic.

The balloon also may be designed to have sections that expand at different rates and/or lengths during inflation. This characteristic may be realized by several methods, such as by thinning the balloon wall in the areas to allow for more expansion, and/or a special extrusion with different materials at different areas around the circumference of the balloon tubing (e.g., extruding more elastic material in the areas that are desired to expand more). This method also may produce a balloon with asymmetric inflation utility.

The balloon also may have a reduced diameter profile in the area just under the stent, such as the sides, to reduce the crossing profile as well as to "nest" the ends of the stent, which reduces the potential for the stent end to abrade the inside of the vessel during stent advancement in the vessel A coil or other mandrel may be inserted into the inflation lumen during the inserting into the vascular system, to provide additional pushability The coil or other mandrel may or may not be removed prior to inflating the balloon The distal tip may be heat formed to taper to seal the inflation/deflation lumen and provide a tapered transition between the guide wire and tip of catheter The catheter can be used in stent deployment, drug delivery, therapeutic infusion, and/or other diagnostic, therapeutic, preventative procedures or any combination of these or other suitable procedure. For example, the catheter can be used for therapeutic infusion by including ports or "weeping" through on the balloon, recessed region in the balloon for pooling of therapeutics for prolonged exposure, as described in greater detail in Houser (U.S. Pat. No. 5,865, 801). The catheter also can be configured to have an infusion port in between a pair of lumens. The infusion port may be in fluid communication with the proximal end of the catheter using a Luer fitting or other suitable fitting. The infusion port also can be implemented using a separate, full catheter length lumen.

The catheter also can be configured to include one or more lumens and port(s) that exit the catheter wall, are located proximal to and/or distal to the balloon, or in the case of multiple balloons, in-between multiple balloons. This feature may be used for therapeutic or diagnostic fluid suction and/or infusion, or may used for other purposes, such as to insert a device or other object.

The balloon may be formed as described, for example, in Anderson (U.S. Pat. No. 6,007,517), which is incorporated herein by reference in its entirety. The balloon may be formed with flow channels for perfusion or guide wire passages passing through it. The channels or passages can be formed by molding and/or extrusion techniques. In one method, a modified modeling process, prior to the molding process, both the proximal and distal ends of the balloon are affixed to the catheter shaft. The balloon has excess material about the sites where one or more channels are to be formed. The excess material corresponds to the surface(s) on the interior to the balloon and therefore will be sufficient to permit formation of inner channels or passages. If the channel or passage material should be thicker than typical, the manufacturer can use thicker material in this region where excess material is desired. This can be accomplished in several ways. In one aspect, prior to bonding to the shaft, the balloon material is extended with thickened walls in the regions where a channel is to be formed. The quantities of excess balloon material and proper thickness can be determined in a given case by routine experimentation. Upon molding, the thicker regions form the channels. Alternatively, one can layer standard longitudinal sections of balloon material in those regions where thickening is required using bonding techniques and then mold the balloon. The bonded layer not only thickens the regions needed to form the channels but functions as a scaffold. Conventional adhesives also can be used to bond the extruded balloon to the shaft. The layers also can be conventionally heat-sealed. The channel walls also can includes materials other than balloon materials that are adjoined to the balloon to form the channels. In addition, the channel walls can be treated to increase strength.

During manufacturing, one or more cylindrical members may be placed within a balloon mold in the position of the one or more desired channel(s). The members may be pre-mounted to the mold. When the balloon is inflated within the mold, the excess balloon material envelopes the cylindrical members. During or after the molding process, the contiguous balloon material is conventionally heat sealed to form the channel(s) or is otherwise sealed using, for example, adhesives. For example, once the balloon molding is completed, the mold is separated, the cylindrical members used to support the flow channels during molding are removed, and the initially excess balloon material is bonded together using the techniques describe above to complete its circumference. That excess material will have formed channel(s) and includes the outermost portion of the channels. It is also possible to use one or more movable cylindrical members that are moved toward each other during the molding process to facilitate achievement of the channels.

In another manufacturing method, the balloon and its one or more channels are extruded using conventional plastic extrusion technology. The one or more interior channels are achieved by extrusion of one or more cylinders or mandrils or wires having walls of a desired thickness within the larger cylinder that is the balloon. The inner channel may be extruded at the same time as the exterior balloon in a single process. The channel(s) also may be separately extruded and then added to the interior of the larger, exterior balloon at the time of assembly by sealing using, for example, adhesives or by heat sealing and cutting away the openings to the channels.

Figure 97D:
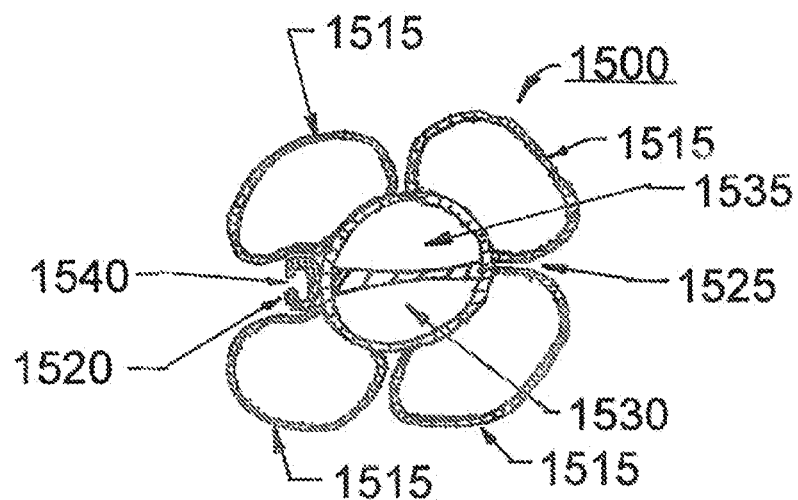
Figure 97E:
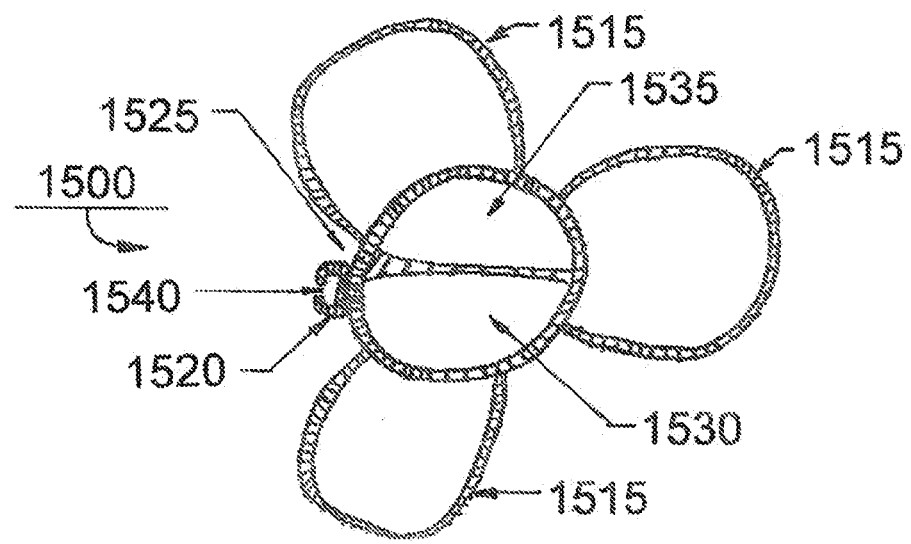

Referring to FIGS. 97a–97e, a catheter 1500 includes a hub 1505, a shaft 1510, one or more balloons 1515, and one or more slotted guide wire tubes 1520 through which guide wires, embolic devices, or other therapeutic or diagnostic devices can be passed. A central lumen 1525 of the shaft 1510 can include a pair of lumens 1530 and 1535 for, e.g., inflating the balloon(s) 1515, passing additional devices, or infusing therapeutic or diagnostic agents. The slotted guide wire tubes 1520 include a channel 1540 into which the guide wire can be slidably inserted and/or press through the slot into the channel 1540. Although a single slotted guide wire tube 1520 is illustrated, additional guide wire tubes 1520 can be placed along the entire length, part of the length, or at any position along the length of the catheter. The balloons 1515 can be separately inflated or simultaneously inflated and can be configured as a pair of balloons (FIG. 97b), a single balloon that encircles a portion of the circumference of the catheter 1500 (FIG. 97c); four balloons (FIG. 97d), or three balloons (FIG. 97d). Although a catheter 1500 is illustrated with one to four balloons, more balloons can be placed around the circumference of the catheter.

The potential benefits of these balloon designs include the ability to position a non-balloon section or a reduced balloon section over a calcified lesion to reduce or eliminate direct pressure at that site, which is believed to be useful in preventing damage to the vessel The dual balloon configuration (FIG. 97b) has a generally hour-glass shaped balloon configuration that allows radial expansion in a single plane or reduced circumferential distance, rather than the completely circumferential expansion as the typical balloon catheter is inflated.

Figure 98E:
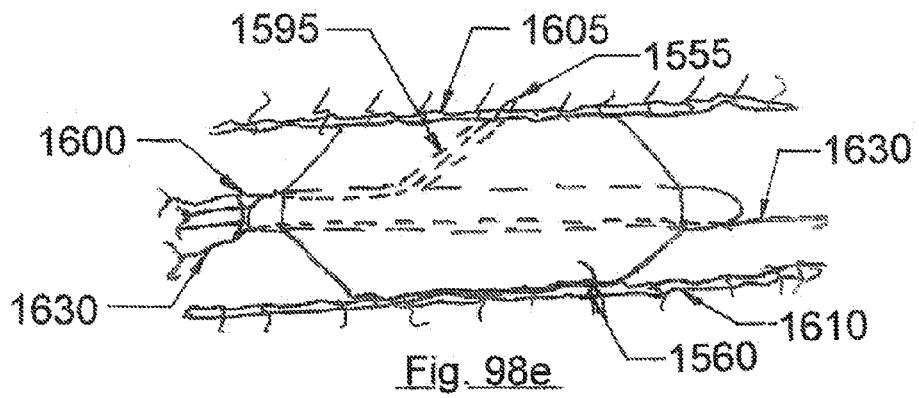
FIG. 98e is a cross-sectional side view of the catheter of FIG. 98a and a hollow-tipped guide wire placed within the lumen of a blood vessel.
Figure 98F:
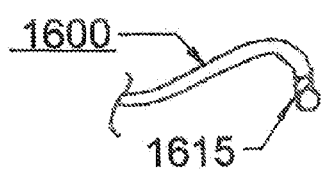
FIGS. 98f and 98g are a perspective view and an end view of the hollow-tipped guide wire of FIG. 98e
Figure 98G:
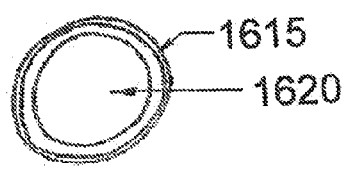
Figure 98H:
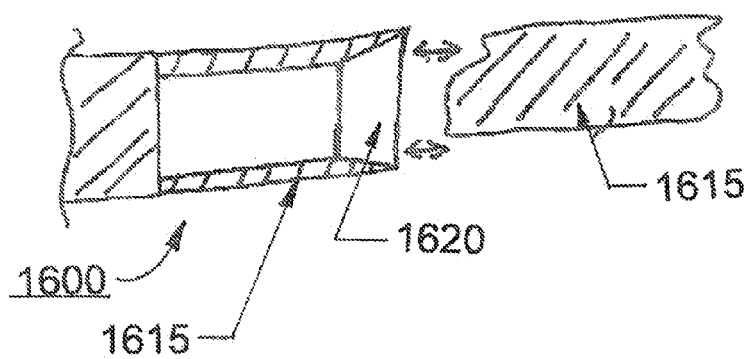
FIG. 98h is a cross sectional side view of the distal end of the hollow-tipped guide wire and a section of plaque.

Referring to FIGS. 98*a*–98*d*, a balloon catheter 1550 is configured to provide a side port 1555 through a balloon 1560 for advancing a device, such as a guide wire 1565. In this manner, guide wires can be placed for advancing a bifurcated stent into a main vessel and a side branch of that main vessel. In contrast to the balloon catheter 1500, the balloon catheter 1550 is formed in the balloon forming process with a fold 1570 along its length. The catheter 1550 includes a shaft 1575 having at least one lumen 1580 and a pair of guide wire channels 1585, 1590 that run along at least a portion of the length of the shaft. For example, either or both of the channels 1585, 1590 can pass along the catheter shaft 1575 below the balloon 1560 for the entire length of the balloon or a portion of the length of the balloon, as illustrated in FIG. 98*a*. The fold 1570 can be positioned above one of the channels 1590 and a radial channel 1595 formed in the fold between the channel 1590 and the side port 1555. As described below, the radial channel 1595 can be formed, for example, during the balloon formation process by inserting a pin between the folds. The radial channel 1595 may be an indention in the balloon material that forms the channel when the opposing sides of the fold are apposed upon inflation. The guide wire channel 1590 can terminate or have an opening that is contiguous with the radial channel 1595. In this manner, a guide wire in the guide wire channel 1590 can be advanced forward into the vessel in which the catheter 1550 is placed by leaving the balloon deflated or by inflating the balloon and advancing the guide wire into the radial channel 1595, through the side port 1555, and into a branch of the vessel from the main vessel. Or, as described below, a diagnostic or therapeutic device can be passed through the radial channel 1595 into the side wall of the vessel surrounding the catheter.

Referring also to FIGS. 98*e*–98*h*, in one implementation, the diagnostic device can be a hollow-tipped guide wire 1600 that can be inserted into tissue and/or plaque 1605 to obtain a biopsy or plaque sample from a vessel 1610. The guide wire tip 1615 is hollow or includes an opening 1620 to received tissue or plaque 1605. The tip 1615 may be sharpened to facilitate insertion into tissue or plaque 1605. The length of a hollow section 1625 is long enough to provide a sufficient quantity of material to analyze. Although the device is described as being a hollow-tipped guide wire, it also may be a tube, probe, or other similar device that can be guided along the catheter, through a portion of an inflated balloon (or, alternatively a catheter without a balloon), and be directed through the vasculature to a desired location along the vessel wall. For example, a diagnostic instrument such as an ultrasonic transducer or device for visualizing or ablating, a tissue density-measuring device, an oxygen-sensing probe, a temperature-sensing probe, or other suitable type of probe may be used to analyze the characteristics of the plaque.

The hollow tipped guide wire or other suitable device is used to access, capture, and retrieve a sample of the lesion (including plaque or other type of occlusion) for better diagnosis and to choose the best mode of treatment. For example, the retrieved tissue, lesion, or plaque may be analyzed to determine its physical and chemical composition before the physician decides the most appropriate treatment method for that particular site. For therapeutic purposes, a special hollow guide wire or infusion device may be used to infuse a therapeutic material, such as a pharmacological or gene-therapy based agent at, in or near the plaque, occlusion or vessel wall. The infused or applied material may include materials that would bind, reinforce, seal or stabilize the occlusion to prevent or make the vulnerable plaque less likely to rupture. Examples of the general classes of these materials include an adhesive and/or a pharmacological material. The infused material may be a liquid that becomes a solid or gel upon placement and/or activation.

The guide wire 1600 can be used in the diagnosis and treatment of vulnerable plaque by obtaining a sample of plaque and identifying characteristics of vulnerable plaque: Some of the diagnostic methods include temperature measurement (by means of one or more of a thermocouple, thermistor, fluorescing means or other temperature sensing means), density measurement, oxygen content measurement, composition analysis, shape or size characteristics, location within the lesion, and/or physical strength.

In this implementation, a first guide wire 1630 may be used to direct the catheter to the desired location and a second guide wire 1600 may be the hollow guide wire for tissue or plaque access and retrieval. When the catheter is used to access and retrieve a lesion sample, the balloon 1560 may be inflated to a lower pressure than would be used for a therapeutic dilatation so that the lesion remains stable during the process of accessing and removing the sample. The balloon can remain inflated, if necessary, to keep it stable during the time required to analyze the sample to determine it composition and the best treatment for the particular lesion. For periods of extended balloon inflation, a perfusion feature (e.g., a perfusion lumen in or on catheter shaft or openings through the tubing wall placed proximal and distal to the balloon) may be included in the catheter design.

Referring to FIGS. 99*a*–99*e*, a catheter 1650 can be configured with a guide wire channel 1655 that is within a catheter shaft 1660, a balloon 1665 that includes a radially extending channel 1670 that terminates at a side port 1675. The radially extending channel 1670 is formed in a fold 1680 in the balloon 1665. In contrast to the balloon catheter 1550 of FIGS. 98*a*–98*d*, the balloon 1665 and the fold 1680 extend into the guide wire channel 1655. The guide wire channel 1655 can extend the entire length of the balloon 1665, as illustrated in FIGS. 99*a*–99*d*, or only a portion of the length of the balloon. For example, the balloon can extend only to the radially extending channel 1670 such that a guide wire or other device that is inserted into the guide wire channel 1655 will pass into the radially extending channel and can be advanced into a branch vessel or into the vessel wall or plaque, as described above.

The fold 1680 and radially extending channel 1670 can be formed by placing a cylindrical member, such as a pin 1690 (FIG. 99*e*) in a mold and forming the balloon around the pin. The pin 1690 include a first section 1692 and a second section 1694. The first section 1692 and the second section 1694 are joined at an angle A. The first section 1692 is placed within the guide wire channel 1655 and the second section 1694 then corresponds to the radially extending channel 1670. The angle A can be set at any angle between slightly greater than 0° and slightly less than 180°, although the most typical angle will be an angle between approximately 90° and approximately 150°.

Although only one cylindrical member or pin can be used in forming the radially extending channel, one or more cylindrical members or pins can placed within the balloon mold in the position of the one or more desired channels. When inflating the balloon within the mold, the balloon material envelopes the one or more cylindrical members to form one or more radially extending channels. The members may be pre-attached to the mold or may be a separate piece or pieces. These and other balloon forming methods known to those of skill in the art are disclosed in Houser (U.S. Pat. No. 5,865,801) and Anderson (U.S. Pat. No. 6,007,517), both of which are incorporated herein by reference.

Another version of the catheter design may be implemented without a balloon. This implementation may be used as a carrier for insertion of multiple guide wires, catheters, and/or other devices, such as leads, at various locations within the cardiovascular system, particularly the main and branching coronary arteries. Once the guide wires have been inserted into the desired vessels (e.g., main vessel and side branch) the guide wire carrier catheter is withdrawn. The proximal ends of the guide wires may be temporarily or permanently marked with the specific anatomic location of each guide wire. Therapeutic, diagnostic or other medical devices (including other catheters) may then be guided to the appropriate anatomic location by the previously inserted guide wires.

The catheters described herein optionally can be configured to provide electroporation during therapeutic infusion. In this mode, the catheters provide the ability to actively stimulate tissue to facilitate intracellular application of the therapeutic solutions. For example, a section of the balloon or catheter body may include a component or coating that can function as an electrode to deliver high voltage electrical pulses into adjacent tissue to cause electroporation of tissue within the desired region, for greater absorption of the therapeutic fluid into the tissue.

The catheters described herein also optionally can be configured to include a piezoelectric film on the balloon for inducement of cavitation (e.g., during therapeutic infusion), an ultrasonic transducer to provide for visualization, ultrasonic ablation, electroporation, and/or pressure sensing devices. The catheters also can optionally include heating capabilities without or without temperature sensing or control using direct resistive element or ohmic tissue methods to treat tissue, deliver or deploy a shape memory stent or other shape memory device. The heating capabilities can be provided using one or more heating means, such as a thin film heating element, a resistive wire or strip (e.g., for resistive element beating), a conductive wire or strip (e.g., for ohmic tissue heating), or an ultrasonic transducer. The heating means can be positioned on the catheter, on or inside the balloon, or as a separate device positioned within or adjacent to the catheter. Many of these features and capabilities are described in Houser (U.S. Pat. No. 5,865,801).

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Finally, it is contemplated that any single feature or any combination of optional features of the inventive variations described herein may be specifically excluded from the claimed invention and be so described as a negative invention. Accordingly, it is not intended that the invention be limited, except as by the appended claims.

We claim:

1. A catheter configured to be inserted into a vessel within a mammalian body, the catheter comprising:
    a tubular body having an exterior surface, a first end and a second end, and defining a length between the first end and the second end;
    at least one channel extending longitudinally along the tubular body at least for a portion of the length of the tubular body, the channel passing between a first opening and a second opening, the channel having an outer surface extending outwardly beyond the circumference of the exterior surface of the tubular body and having a slot formed by a pair of edges of the outer surface of the channel such that a tubular member can be passed between the channel and the outer surface, wherein the slot extends from the first opening to the second opening;
    a central lumen extending along the tubular body at least for a portion of the length of the tubular body; and
    a balloon extending around the tubular body proximal of the second end of the tubular body, wherein the balloon extends at least partially over the slot in an inflated state and at least a portion of the balloon being in contact with the exterior surface of the tubular body.

2. The catheter of claim 1, wherein the balloon extends into the channel for at least a portion of the length of the channel.

3. The catheter of claim 2, wherein the balloon further includes a first surface extending from the channel and a second surface extending from the channel.

4. The catheter of claim 3, wherein each of the first surface and the second surface include a radially extending channel passing between the channel in the tubular body and an opening on an outer surface of the balloon.

5. The catheter of claim 1, wherein the pair of edges are aligned and spaced apart from one another.

6. The catheter of claim 1, further comprising a second channel extending longitudinally along the tubular body at least for a portion of the length of the tubular body.

7. The catheter of claim 1, wherein the catheter is intended to be used to carry a guide wire or lead in the channel.

8. The catheter of claim 1, wherein the tubular member comprises a guide wire or lead.

9. A catheter configured to be inserted into a vessel within a mammalian body, the catheter comprising:
    a tubular body having an exterior surface, a first end and a second end, and defining a length between the first end and the second end;
    at least one channel formed by a pair of longitudinal ridges extending along the outer surface of the tubular body at least for a portion of the length of the tubular body, the channel passing between a first opening and a second opening and having a slot between the channel and the exterior surface of the tubular body such that a tubular member can be passed between the channel and the exterior surface, wherein the slot extends from the first opening to the second opening and wherein the slot is formed by includes a pair of edges of the outer surface of the channel;

a central lumen extending along the tubular body at least for a portion of the length of the tubular body; and a balloon extending around the tubular body proximal of the second end of the tubular body, wherein the balloon extends at least partially over the slot in an inflated state and at least a portion of the balloon being in contact with the exterior surface of the tubular body, wherein the balloon comprises at least two discrete diameters.

10. The catheter of claim 2, wherein the balloon comprises a diameter that is tapered along a length of the balloon.

11. The catheter of claim 1, further comprising a band encircling at least a portion of a circumference of the tubular body proximal of the second end of the tubular body.

12. The catheter of claim 11, wherein the channel passes below the band.

* * * * *